United States Patent
Li et al.

(10) Patent No.: US 11,767,525 B2
(45) Date of Patent: Sep. 26, 2023

(54) SYSTEM AND METHOD FOR GENOME EDITING

(71) Applicant: INSTITUTE OF ZOOLOGY, CHINESE ACADEMY OF SCIENCES, Beijing (CN)

(72) Inventors: Wei Li, Beijing (CN); Qi Zhou, Beijing (CN); Fei Teng, Beijing (CN)

(73) Assignee: Institute of Zoology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/611,831

(22) PCT Filed: Dec. 27, 2017

(86) PCT No.: PCT/CN2017/118948
§ 371 (c)(1),
(2) Date: Nov. 7, 2019

(87) PCT Pub. No.: WO2019/127087
PCT Pub. Date: Jul. 4, 2019

(65) Prior Publication Data
US 2021/0095271 A1    Apr. 1, 2021

(51) Int. Cl.
| | | |
|---|---|---|
| *C12N 15/11* | (2006.01) | |
| *C12N 9/22* | (2006.01) | |
| *C12N 15/90* | (2006.01) | |
| *C12N 15/113* | (2010.01) | |
| *A61K 38/46* | (2006.01) | |
| *A61P 9/00* | (2006.01) | |
| *A61P 25/00* | (2006.01) | |
| *A61P 25/16* | (2006.01) | |
| *A61P 25/18* | (2006.01) | |
| *A61P 25/28* | (2006.01) | |
| *A61P 25/30* | (2006.01) | |
| *A61P 27/02* | (2006.01) | |

(52) U.S. Cl.
CPC ............. *C12N 15/11* (2013.01); *C12N 9/22* (2013.01); *C12N 15/907* (2013.01); *C12N 2310/20* (2017.05)

(58) Field of Classification Search
None
See application file for complete search history.

(56) References Cited

FOREIGN PATENT DOCUMENTS

WO    WO 2016/205749 A1    12/2016

OTHER PUBLICATIONS

Liu et al. (Molecular Cell, Jan. 2017. vol. 65:310-322.Epub Dec. 15, 2016).*
Shemesh, et al. "UniProtKB/SwissProt: T0D7A2.1," *Genbank*, Nov. 22, 2017.
International Search Report for PCT/CN2017/118948, dated Sep. 28, 2018 (4 pages).
Hosoyama et al., "Whole Genome Shotgun Sequence of Alicyclobacillus Acidiphilus NBRC 100859," *Genbank*, NCBI Reference Sequence: NZ_BCQI01000053.1, Apr. 2017.

* cited by examiner

*Primary Examiner* — Suzanne M Noakes
*Assistant Examiner* — Jae W Lee
(74) *Attorney, Agent, or Firm* — Klarquist Sparkman, LLP

(57) ABSTRACT

Provided are a genome editing system CRISPR-C2c1 for site-specific modification of target sequences in a cell genome and the use thereof, wherein the system comprises a C2c1 protein or variants thereof and a guide RNA. Also provided are a method for site-specific modification of target sequences in a cell genome using the genome editing system CRISPR-C2c1, and a pharmaceutical composition comprising the genome editing system CRISPR-C2c1.

14 Claims, 13 Drawing Sheets
Specification includes a Sequence Listing.

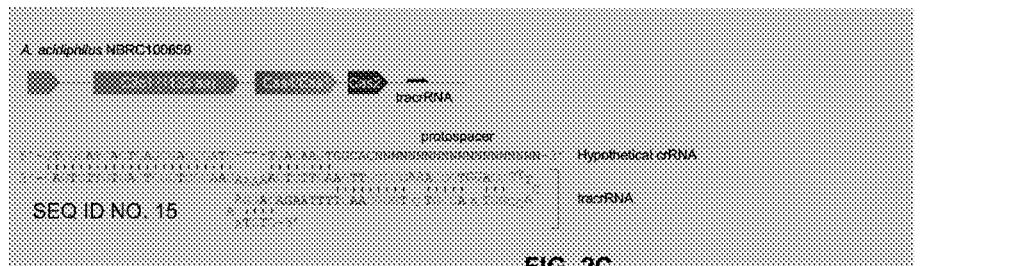
FIG. 2A
FIG. 2B
FIG. 2C
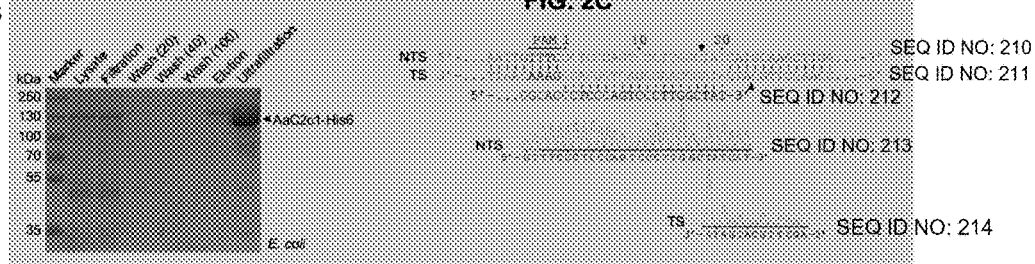
FIG. 2D
FIG. 2E

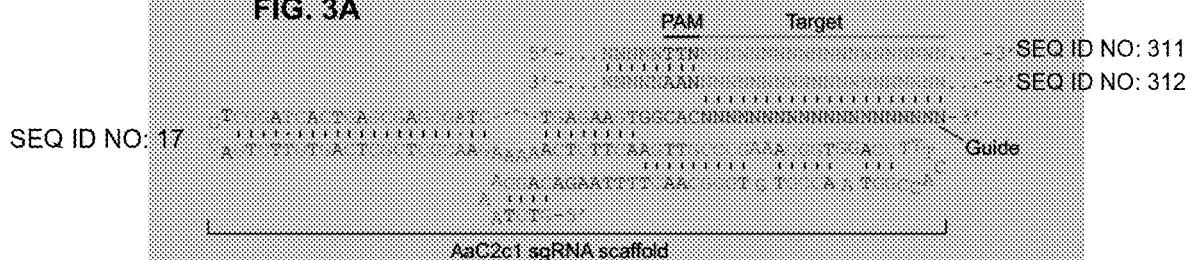
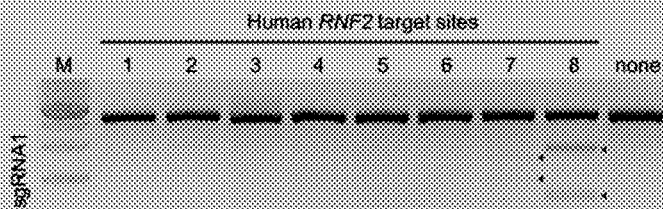

FIG. 4A

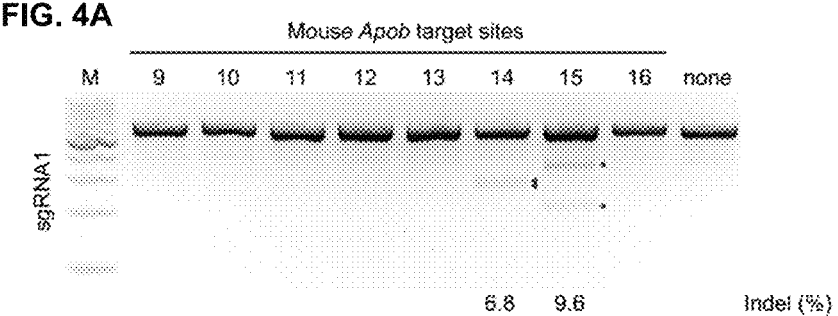

FIG. 4B

Mouse *Apob* target site 14
TTGGACACCAGCGTCTGGGCTCGTGAGTTAGGGTGGAAGCCTGGGAGAAAGCCAG   SEQ ID NO: 226
TTGGACACCAGCGTCTGGGCTC-------TTAGGGTGGAAGCCTGGGAGAAAGCCAG   SEQ ID NO: 227

Mouse *Apob* target site 15
GCTGTGCTACAGACTACCAGTTACATCCTGGGGTAGAAACTGGTGGCAGGCTGGC   SEQ ID NO: 228
GCTGTGCTACAGAC-----CAGTTACATCCTGGGGTAGAAACTGGTGGCAGGCTGGC   SEQ ID NO: 229

FIG. 4C

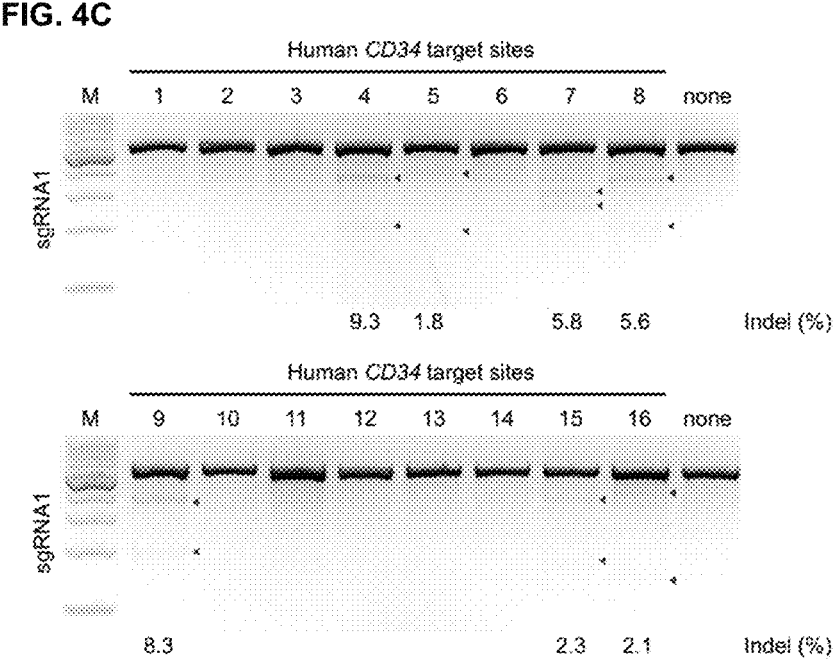

FIG. 4D

Human *CD34* target site 4
TTCAGACCTTTCAACCACTAGCACTAGCCTTGCAACATCTCCCACTAAACCCTAT   SEQ ID NO: 230
TTCAGACCTTTCAACCACTAGCACTAGC-----CAACATCTCCCACTAAACCCTAT   SEQ ID NO: 231

Human *CD34* target site 7
T--------------TGAAGC----------------CTAGCCTGTCACCTGGAAA   SEQ ID NO: 232
TggcggactgcggcctgaagcactgatgcgctgctCTAGCCTGTCACCTGGAAA   SEQ ID NO: 233

Human *CD34* target site 8
ACCTTTCAACCACTAGCACTAG-------CCTTGCAACATCTCCCACTAAACCCTAT   SEQ ID NO: 234
ACCTTTCAACCACTAGCACTAGactagCCTTGCAACATCTCCCACTAAACCCTAT   SEQ ID NO: 235
ACCTTTCAACCACTAGCACTA--------TTGCAACATCTCCCACTAAACCCTAT   SEQ ID NO: 236

FIG. 4E

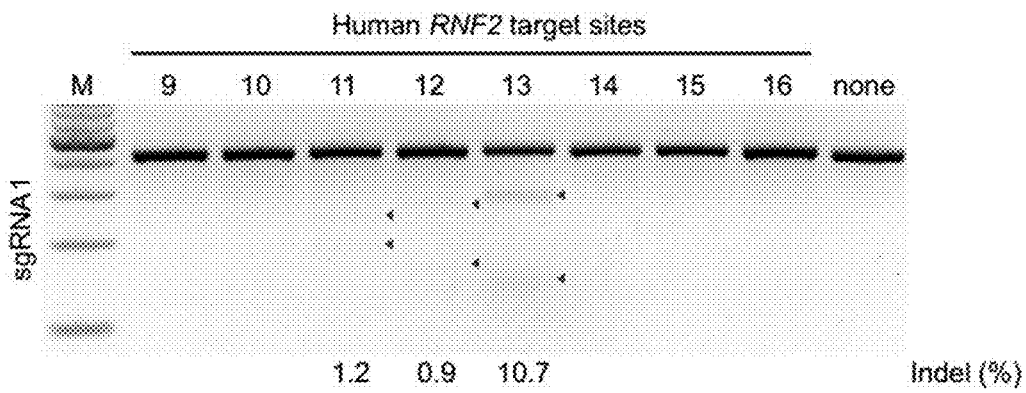

FIG. 4F

Human *RNF2* target site 13

```
TGCCCAATTTGTTTGGATATGTTGAAGAACACCATGACTACAAAGGAGTGTTTAC  SEQ ID NO: 237
TGCCCAATTTGTTTGGATATGTTGAA----------TGACTACAAAGGAGTGTTTAC  SEQ ID NO: 238
TGCCCAATTTGTTTGGATATGTTGAA-----------GACTACAAAGGAGTGTTTAC  SEQ ID NO: 239
TGCCCAATTTGT----------------------------AAGGAGTGTTTAC  SEQ ID NO: 240
```

FIG. 4G

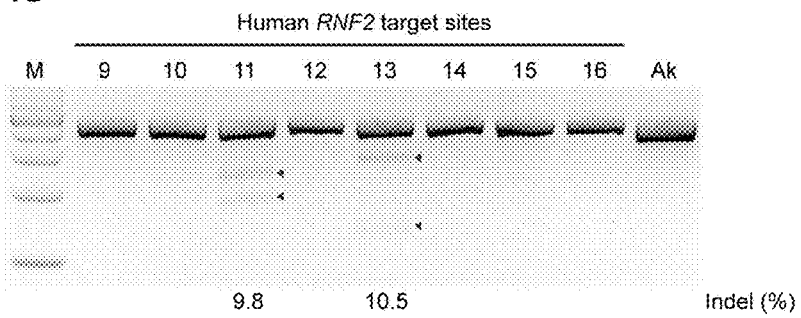

FIG. 4H

Human *RNF2* target site 13

```
TGCCCAATTTGTTTGGATATGTTGAAGAACA---CCATGACTACAAAGGAGTGTTT  SEQ ID NO: 241
TGCCCAATTTGTTTGGATATGTTGAAGAACAaCCATGACTACAAAGGAGTGTTT    SEQ ID NO: 242
TGCCCAATTTGTTTGGATATGTTGAAGAACA-----TGACTACAAAGGAGTGTTT   SEQ ID NO: 243
TGCCCAATTTGTTTGGATATGTTGAAGAACA-----TGACTACAAAGGAGTGTTT   SEQ ID NO: 244
TGCCCAATTTGTTTGGATATGTTGAAGAACA--C-----CTACAAAGGAGTGTTT   SEQ ID NO: 245
TGCCCAATTTGTTTGGATATGTTGAAGAAC--------tCTACAAAGGAGTGTTT   SEQ ID NO: 246
TGCCCAATTTGTaTGGA------------------------------GTGTTT    SEQ ID NO: 247
```

FIG. 6A

SEQ ID NO: 167
SEQ ID NO: 168
SEQ ID NO: 169
SEQ ID NO: 170
SEQ ID NO: 171

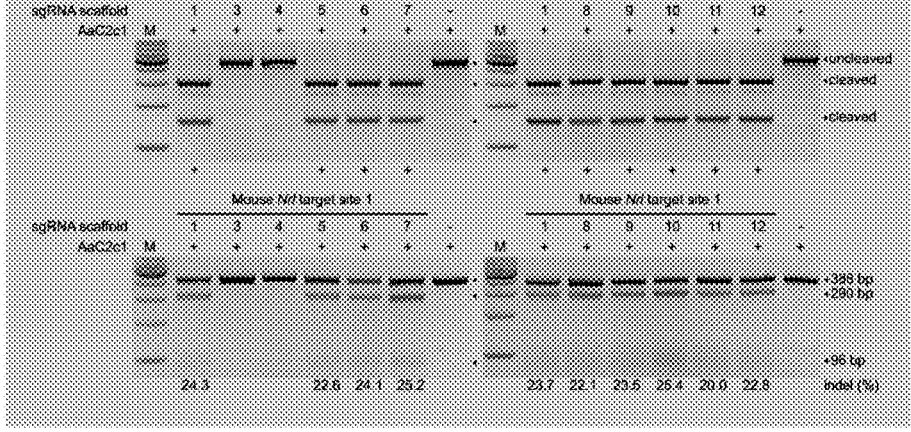

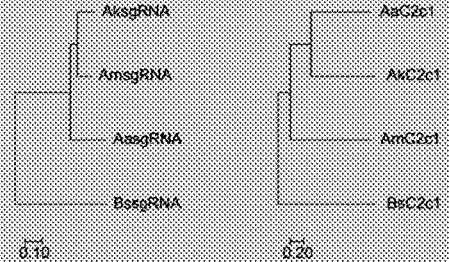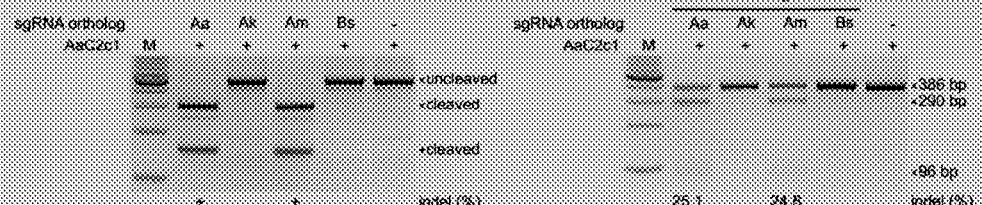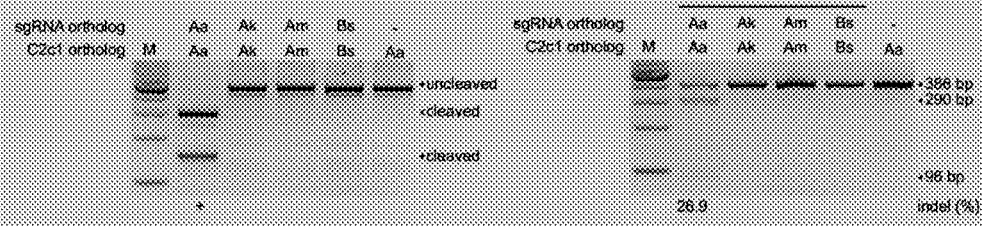

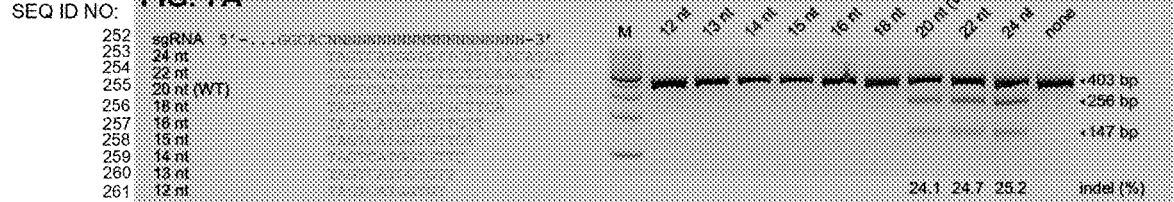
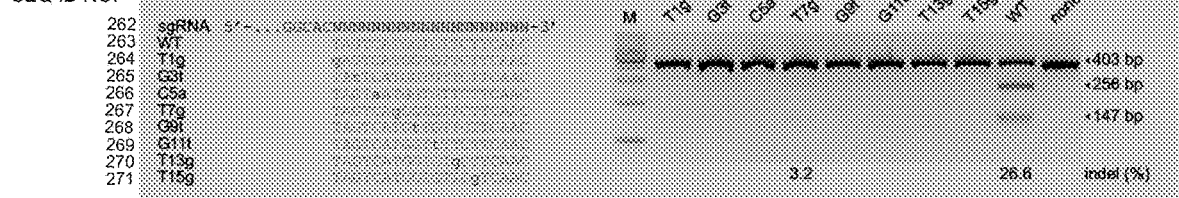
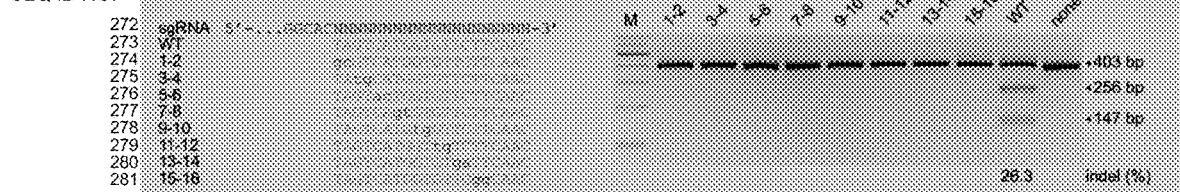
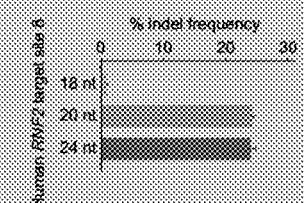
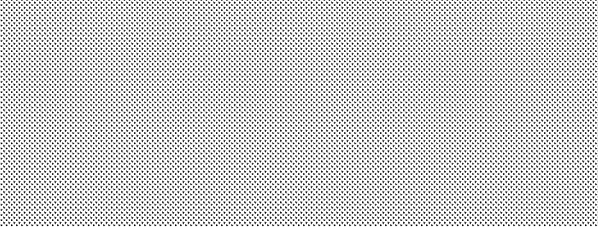

FIG. 9A
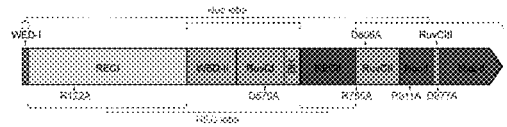
FIG. 9B
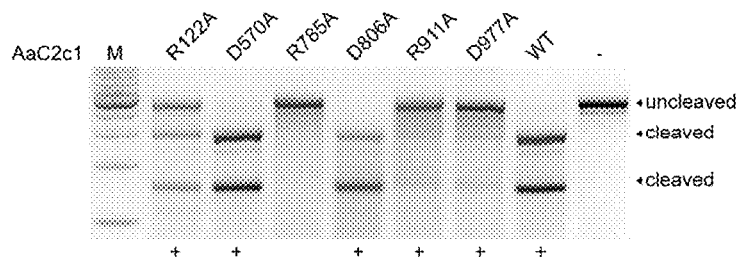
FIG. 9C
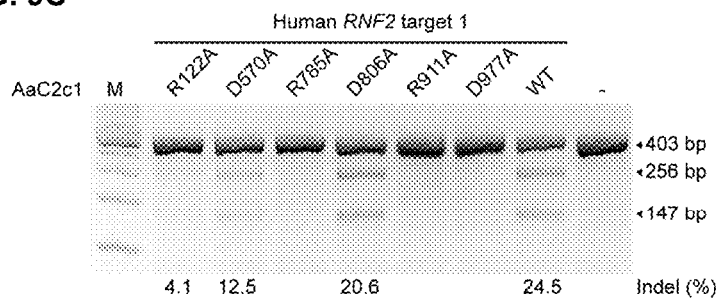
FIG. 9D
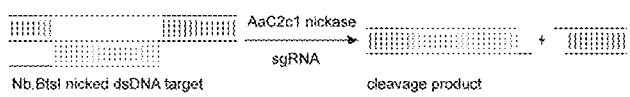
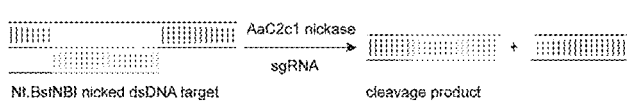
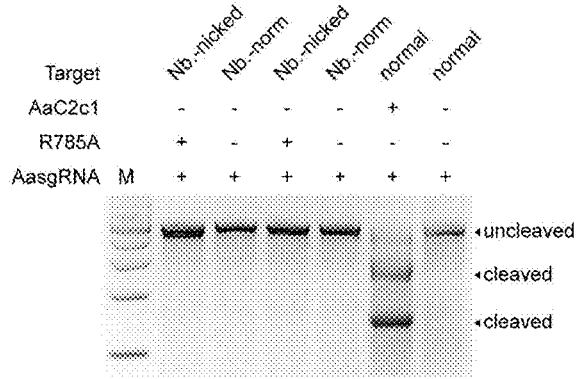

SEQUENCE LISTING

<160> NUMBER OF SEQ ID NOS: 317

<210> SEQ ID NO 1
<211> LENGTH: 1129
<212> TYPE: PRT
<213> ORGANISM: Alicyclobacillus acidiphilus

<400> SEQUENCE: 1

Met Ala Val Lys Ser Met Lys Val Lys Leu Arg Leu Asp Asn Met Pro
1               5                   10                  15

Glu Ile Arg Ala Gly Leu Trp Lys Leu His Thr Glu Val Asn Ala Gly
                20                  25                  30

Val Arg Tyr Tyr Thr Glu Trp Leu Ser Leu Leu Arg Gln Glu Asn Leu
            35                  40                  45

Tyr Arg Arg Ser Pro Asn Gly Asp Gly Glu Gln Glu Cys Tyr Lys Thr
        50                  55                  60

```
Ala Glu Glu Cys Lys Ala Glu Leu Leu Glu Arg Leu Arg Ala Arg Gln
 65                  70                  75                  80

Val Glu Asn Gly His Cys Gly Pro Ala Gly Ser Asp Asp Glu Leu Leu
                 85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
130                 135                 140

Lys Pro Arg Trp Val Arg Met Arg Glu Ala Gly Glu Pro Gly Trp Glu
145                 150                 155                 160

Glu Glu Lys Ala Lys Ala Glu Ala Arg Lys Ser Thr Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Asp Met Ser Ser Val Gln Trp Lys Pro Leu Arg
        195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Glu
225                 230                 235                 240

Ala Tyr Ala Lys Leu Val Glu Gln Lys Ser Arg Phe Glu Gln Lys Asn
                245                 250                 255

Phe Val Gly Gln Glu His Leu Val Gln Leu Val Asn Gln Leu Gln Gln
            260                 265                 270

Asp Met Lys Glu Ala Ser His Gly Leu Glu Ser Lys Glu Gln Thr Ala
        275                 280                 285

His Tyr Leu Thr Gly Arg Ala Leu Arg Gly Ser Asp Lys Val Phe Glu
290                 295                 300

Lys Trp Glu Lys Leu Asp Pro Asp Ala Pro Phe Asp Leu Tyr Asp Thr
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Lys Tyr Gln Ala Leu Trp Arg
            340                 345                 350

Glu Asp Ala Ser Phe Leu Thr Arg Tyr Ala Val Tyr Asn Ser Ile Val
        355                 360                 365

Arg Lys Leu Asn His Ala Lys Met Phe Ala Thr Phe Thr Leu Pro Asp
370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Gly Arg His
                405                 410                 415

Ala Ile Arg Phe Gln Lys Leu Leu Thr Val Glu Asp Gly Val Ala Lys
            420                 425                 430

Glu Val Asp Asp Val Thr Val Pro Ile Ser Met Ser Ala Gln Leu Asp
        435                 440                 445

Asp Leu Leu Pro Arg Asp Pro His Glu Leu Val Ala Leu Tyr Phe Gln
450                 455                 460

Asp Tyr Gly Ala Glu Gln His Leu Ala Gly Glu Phe Gly Gly Ala Lys
465                 470                 475                 480

Ile Gln Tyr Arg Arg Asp Gln Leu Asn His Leu His Ala Arg Arg Gly
```

```
                    485                 490                 495
Ala Arg Asp Val Tyr Leu Asn Leu Ser Val Arg Val Gln Ser Gln Ser
                500                 505                 510

Glu Ala Arg Gly Glu Arg Arg Pro Pro Tyr Ala Ala Val Phe Arg Leu
                515                 520                 525

Val Gly Asp Asn His Arg Ala Phe Val His Phe Asp Lys Leu Ser Asp
            530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Glu Gly Arg Val Pro Phe Cys Phe Pro Ile Glu Gly Asn Glu
                595                 600                 605

Asn Leu Val Ala Val His Glu Arg Ser Gln Leu Leu Lys Leu Pro Gly
            610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Glu Arg Ser Trp Ala Lys
            660                 665                 670

Leu Ile Glu Gln Pro Met Asp Ala Asn Gln Met Thr Pro Asp Trp Arg
                675                 680                 685

Glu Ala Phe Glu Asp Glu Leu Gln Lys Leu Lys Ser Leu Tyr Gly Ile
            690                 695                 700

Cys Gly Asp Arg Glu Trp Thr Glu Ala Val Tyr Glu Ser Val Arg Arg
705                 710                 715                 720

Val Trp Arg His Met Gly Lys Gln Val Arg Asp Trp Arg Lys Asp Val
                725                 730                 735

Arg Ser Gly Glu Arg Pro Lys Ile Arg Gly Tyr Gln Lys Asp Val Val
            740                 745                 750

Gly Gly Asn Ser Ile Glu Gln Ile Glu Tyr Leu Glu Arg Gln Tyr Lys
            755                 760                 765

Phe Leu Lys Ser Trp Ser Phe Phe Gly Lys Val Ser Gly Gln Val Ile
            770                 775                 780

Arg Ala Glu Lys Gly Ser Arg Phe Ala Ile Thr Leu Arg Glu His Ile
785                 790                 795                 800

Asp His Ala Lys Glu Asp Arg Leu Lys Lys Leu Ala Asp Arg Ile Ile
                805                 810                 815

Met Glu Ala Leu Gly Tyr Val Tyr Ala Leu Asp Asp Glu Arg Gly Lys
                820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
            850                 855                 860

Asn Gln Leu Met Gln Trp Ser His Arg Gly Val Phe Gln Glu Leu Leu
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910
```

Arg Arg Val Pro Ala Arg Cys Ala Arg Glu Gln Asn Pro Glu Pro Phe
            915                 920                 925

Pro Trp Trp Leu Asn Lys Phe Val Ala Glu His Lys Leu Asp Gly Cys
    930                 935                 940

Pro Leu Arg Ala Asp Asp Leu Ile Pro Thr Gly Glu Gly Glu Phe Phe
945                 950                 955                 960

Val Ser Pro Phe Ser Ala Glu Glu Gly Asp Phe His Gln Ile His Ala
            965                 970                 975

Asp Leu Asn Ala Ala Gln Asn Leu Gln Arg Arg Leu Trp Ser Asp Phe
        980                 985                 990

Asp Ile Ser Gln Ile Arg Leu Arg Cys Asp Trp Gly Glu Val Asp Gly
        995                 1000                1005

Glu Pro Val Leu Ile Pro Arg Thr Thr Gly Lys Arg Thr Ala Asp
    1010                1015                1020

Ser Tyr Gly Asn Lys Val Phe Tyr Thr Lys Thr Gly Val Thr Tyr
    1025                1030                1035

Tyr Glu Arg Glu Arg Gly Lys Lys Arg Lys Val Phe Ala Gln
    1040                1045                1050

Glu Glu Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asp Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Arg Leu Gln Glu Ser Ala Cys Glu Asn Thr Gly Asp
    1115                1120                1125

Ile

<210> SEQ ID NO 2
<211> LENGTH: 3387
<212> TYPE: DNA
<213> ORGANISM: Alicyclobacillus acidiphilus

<400> SEQUENCE: 2
atggccgtta atccatgaa agtgaaactt cgcctcgata tatgccgga gattcgggct      60 ggtttatgga aactccatac ggaggtcaac gcggggttc gatattacac ggaatggctg    120
agtcttctgc gtcaagagaa tttgtatcga gaagtccga atggggacgg agagcaagaa    180
tgttataaga ctgcagaaga atgcaaagcc gaattgttgg agcggctgcg cgcgcgtcaa    240
gtggagaatg acactgtggt tccggcggga tcggacgatg aattgctgca gttggctcgt    300
caactttatg aactgttggt tccgcaggcg ataggtgcga aggcgatgc gcagcaaatt    360 gcgcgcaagt ttttgagccc cttagccgac aaggatgcag tgggtgggct tggaatcgcg    420
aaggcgggga acaaaccgcg gtgggttcgc atgcgcgaag cgggagaacc tggctgggaa    480
gaggagaagg cgaaggctga ggcgaggaaa tctacggatc gaactgcgga tgttttgcgc    540
gcgctcgcgg atttgggtt aaagccactg atgcgcgtgt acaccgattc tgacatgtca    600
tctgttcagt ggaaaccgct tcggaagggc caagcggttc ggacgtggga cagggatatg    660
ttccaacagg ccatcgagcg gatgatgtcg tgggagtcgt ggaatcagcg cgttggcgaa    720
gcgtacgcga aactggtaga gcaaaaaagt cgatttgagc agaagaactt cgtcggccag    780

```
gaacatttgg ttcaactcgt caatcagttg caacaagata tgaaagaagc atcgcacggg    840
ctcgaatcga aagagcaaac cgcacattat ctgacgggac gggcattgcg cggatcggac    900
aaagtgtttg agaagtggga gaaactcgac cctgatgcgc cattcgattt gtacgacacc    960
gaaatcaaga acgtgcagag acgtaacacg aggcgattcg gctcacacga cttgttcgcg   1020
aaattggcgg aaccgaagta tcaggccctg tggcgcgaag atgcttcgtt tctcacgcgt   1080
tacgcggtgt acaacagcat cgttcgcaaa ctgaatcacg ccaaaatgtt cgcgacgttt   1140
actttaccgg atgcaactgc gcatccgatt tggactcgct ttgataaatt gggcgggaat   1200
ttgcaccagt acacctttt gttcaacgaa ttcggagaag caggcacgc gattcgtttt   1260 caaaagctgt tgaccgtcga agatggtgtc gcaaagaag ttgatgatgt aacggtgccc   1320
atttccatgt cagcgcaatt ggatgatctg ctgccaagag atccccatga actggttgca   1380
ctatattttc aagattatgg agccgaacag catttggcgg gtgaattcgg tggcgcgaag   1440
attcagtacc gtcgggatca actaaatcat ttgcacgcac gcagaggggc gagggatgtt   1500
tatctcaatc tcagcgtacg tgtgcagagc cagtctgagg cacggggaga acgccgcccg   1560
ccgtatgccg cagtattccg cctggtcggg acaaccatc gtgcgtttgt ccatttgat    1620 aaattatcgc attatcttgc ggaacatccg gatgatggga gcttggatc ggaggggctg   1680 ctttccgggc tacgggtgat gagtgtcgat ctcggccttc gcacatcggc atcgatttcc   1740
gtttttcgcg ttgcccggaa ggacgagttg aagccgaact cggaagggcg tgtcccattc   1800
tgttttccga ttgaagggaa tgaaaatctc gtcgcggttc atgaacgatc tcaactttg   1860 aagctgcctg gcgaaacaga gtcaaaggac ctgcgggcta tccgagaaga gcgccaacgg   1920
accctgcggc agctgcggac gcaactggcg tatttgcggc tgctcgtgcg gtgtgggtcg   1980
gaagatgtgg gacggcgtga acggagttgg gcaaagctta ttgagcagcc catggatgcc   2040
aatcagatga caccggattg gcgcgaagcc tttgaagacg aacttcagaa gcttaagtca   2100
ctctatggta tctgtggcga cagggaatgg acggaggctg tctacgagag cgttcgccgc   2160
gtgtggcgcc atatgggcaa acaggttcgc gattggcgaa aggacgtacg gagtggagag   2220
cggccgaaga ttcgcggcta tcaaaaagat gtggtcggcg gaaattcgat tgagcaaatt   2280
gagtatcttg aacggcagta caagtttctc aagagttgga gcttttttgg caaggtatcg   2340
ggacaagtga ttcgtgcgga aagggatcc cgatttgcga tcacgctgcg tgaacacatt   2400
gatcacgcga aggaagaccg gctgaagaaa ttggcggatc gcatcattat ggaggcgctc   2460
ggttatgtgt acgcgttgga tgatgagcgc ggcaaaggaa agtgggttgc gaagtatccg   2520
ccgtgccagc tcatcctgct ggaggaattg agcgagtacc agttcaataa cgacaggcct   2580
ccgagtgaaa acaatcagtt gatgcaatgg agccatcgcg gcgtgttcca ggagttgttg   2640
aatcaggccc aagtccacga tttactcgtt gggacgatgt atgcagcgtt ctcgtcgcga   2700
ttcgacgcgc gaaccggggc accgggtatc cgctgtcgca gggtaccggc gcgttgcgct   2760
cgggagcaga atccagaacc atttccttgg tggctgaaca agtttgtggc ggaacacaag   2820
ttggatggtt gtcccttacg ggcagacgac ctcatcccca cgggtgaagg agagttttt   2880 gtctcgccgt tcagtgcgga ggaagggac tttcatcaga ttcatgccga cctgaatgcg   2940
gcgcaaaacc tgcagcggcg actctggtct gattttgata tcagtcaaat tcggttgcgg   3000
tgtgattggg gtgaagtgga cggtgaaccc gttctgatcc caaggaccac aggaaagcga   3060
acggcggatt catatggcaa caaggtgttt tataccaaaa caggtgtcac ctattatgag   3120
cgagagcggg ggaagaagcg gagaaaggtt ttcgcgcaag aggaattgtc ggaggaagag   3180
```

```
gcggagttgc ttgtggaagc agacgaggca agggagaaat cggtcgtttt gatgcgtgat    3240
ccgtccggca ttatcaatcg tggcgactgg accaggcaaa aggagttttg gtcgatggtg    3300
aaccagcgga ttgaaggata cttggtcaag cagattcgct cgcgcgttcg cttacaagaa    3360
agtgcgtgtg aaaacacggg ggatatt                                        3387

<210> SEQ ID NO 3
<211> LENGTH: 3387
<212> TYPE: DNA
<213> ORGANISM: Artificial Sequence
<220> FEATURE:
<223> OTHER INFORMATION: Humanized AaC2c1 coding sequence;DNA;
      Artificial Sequence

<400> SEQUENCE: 3
atggccgtga agagcatgaa ggtgaagctg cgcctggaca catgcccga gatccgcgcc      60 ggcctgtgga agctgcacac cgaggtgaac gccggcgtgc gctactacac cgagtggctg    120
agcctgctgc gccaggagaa cctgtaccgc cgcagcccca cggcgacgg cgagcaggag     180 tgctacaaga ccgccgagga gtgcaaggcc gagctgctgg agcgcctgcg cgcccgccag    240
gtggagaacg ccactgcgg ccccgccggc agcgacgacg agctgctgca gctggcccgc    300
cagctgtacg agctgctggt gccccaggcc atcggcgcca agggcgacgc ccagcagatc    360
gcccgcaagt cctgagccc cctggccgac aaggacgccc tgggcggcct gggcatcgcc    420
aaggccggca acaagccccg ctgggtgcgc atgcgcgagg ccggcgagcc cggctgggag    480
gaggagaagg ccaaggccga ggcccgcaag agcaccgacc gcaccgccga cgtgctgcgc    540
gccctggccg acttcggcct gaagcccctg atgcgcgtgt acaccgacag cgacatgagc    600
agcgtgcagt ggaagcccct cgcaagggc caggccgtgc gcacctggga ccgcgacatg    660
ttccagcagg ccatcgagcg catgatgagc tgggagagct ggaaccagcg cgtgggcgag    720
gcctacgcca gctggtgga gcagaagagc cgcttcgagc agaagaactt cgtgggccag    780
gagcacctgg tgcagctggt gaaccagctg cagcaggaca tgaaggaggc cagccacggc    840
ctggagagca aggagcagac cgcccactac ctgaccggcc gcgccctgcg cggcagcgac    900
aaggtgttcg agaagtggga aagctggac cccgacgccc ccttcgacct gtacgacacc    960
gagatcaaga cgtgcagcg ccgcaacacc cgccgcttcg cagccacga cctgttcgcc    1020 aagctggccg agcccaagta ccaggccctg tggcgcgagg acgccagctt cctgacccgc    1080
tacgccgtgt acaacagcat cgtgcgcaag ctgaaccacg ccaagatgtt cgccaccttc    1140
accctgcccg acgccaccgc ccacccatc tggaccgct tcgacaagct gggcggcaac    1200
ctgcaccagt acaccttct gttcaacgag ttcggcgagg ccgccacgc catccgcttc    1260 cagaagctgc tgaccgtgga ggacggcgtg gccaaggagg tggacgacgt gaccgtgccc    1320
atcagcatga cgcccagct ggacgacctg ctgccccgcg accccacga gctggtggcc    1380 ctgtacttcc aggactacgg cgccgagcag caacctggccg cgagttcgg cggcgccaag    1440 atccagtacc gccgcgacca gctgaaccac ctgcacgccc gccgcggcgc ccgcgacgtg    1500
tacctgaacc tgagcgtgcg cgtgcagagc cagagcgagg cccgcggcga cgccgcccc    1560 ccctacgccg ccgtgttccg cctggtgggc gacaaccacc gcgccttcgt gcacttcgac    1620
aagctgagcg actacctggc cgagcacccc gacgacggca gctgggcag cgagggcctg    1680 ctgagcggc tgcgcgtgat gagcgtggac ctggccctgc gcaccagcgc cagcatcagc    1740
gtgttccgcg tggcccgcaa ggacgagctg aagcccaaca gcgagggccg cgtgcccttc    1800
```

-continued

```
tgcttcccca tcgagggcaa cgagaacctg gtggccgtgc acgagcgcag ccagctgctg    1860
aagctgcccg cgagaccga gagcaaggac ctgcgcgcca tccgcgagga gcgccagcgc    1920
accctgcgcc agctgcgcac ccagctggcc tacctgcgcc tgctggtgcg ctgcggcagc    1980
gaggacgtgg ccgccgcga gcgcagctgg gccaagctga tcgagcagcc catggacgcc    2040
aaccagatga cccccgactg gcgcgaggcc ttcgaggacg agctgcagaa gctgaagagc    2100
ctgtacggca tctgcggcga ccgcgagtgg accgaggccg tgtacgagag cgtgcgccgc    2160
gtgtggcgcc acatgggcaa gcaggtgcgc gactggcgca aggacgtgcg cagcggcgag    2220
cgccccaaga tccgcggcta ccagaaggac gtggtgggcg caacagcat cgagcagatc     2280 gagtacctgg agcgccagta caagttcctg aagagctgga gcttcttcgg caaggtgagc    2340
ggccaggtga tccgcgccga aagggcagc cgcttcgcca tcaccctgcg cgagcacatc     2400
gaccacgcca aggaggaccg cctgaagaag ctggccgacc gcatcatcat ggaggccctg    2460
ggctacgtgt acgccctgga cgacgagcgc ggcaagggca gtgggtggc caagtacccc    2520 ccctgccagc tgatcctgct ggaggagctg agcgagtacc agttcaacaa cgaccgcccc    2580
cccagcgaga caaccagct gatgcagtgg agccaccgcg cgtgttcca ggagctgctg      2640 aaccaggccc aggtgcacga cctgctggtg ggcaccatgt acgccgcctt cagcagccgc    2700
ttcgacgccc gcaccggcgc cccggcatc cgctgccgcc gcgtgcccgc ccgctgcgcc     2760
cgcgagcaga accccgagcc cttccctgg tggctgaaca agttcgtggc cgagcacaag     2820
ctggacggct gccccctgcg cgccgacgac ctgatcccca ccggcgaggg cgagttcttc    2880
gtgagcccct tcagcgccga ggagggcgac ttccaccaga tccacgccga cctgaacgcc    2940
gcccagaacc tgcagcgccg cctgtggagc gacttcgaca tcagccagat ccgcctgcgc    3000
tgcgactggg gcgaggtgga cggcgagccc gtgctgatcc cccgcaccac cggcaagcgc    3060
accgccgaca gctacggcaa caaggtgttc tacaccaaga ccggcgtgac ctactacgag    3120
cgcgagcgcg gcaagaagcg ccgcaaggtg ttcgcccagg aggagctgag cgaggaggag    3180
gccgagctgc tggtggaggc cgacgaggcc cgcgagaaga gcgtggtgct gatgcgcgac    3240
cccagcggca tcatcaaccg cggcgactgg acccgccaga aggagttctg gagcatggtg    3300
aaccagcgca tcgagggcta cctggtgaag cagatccgca gccgcgtgcg cctgcaggag    3360
agcgcctgcg agaacaccgg cgacatc                                       3387
```

<210> SEQ ID NO 4
<211> LENGTH: 1129
<212> TYPE: PRT
<213> ORGANISM: Artificial Sequence
<220> FEATURE:
<223> OTHER INFORMATION: dAaC2c1 protein sequence

<400> SEQUENCE: 4

```
Met Ala Val Lys Ser Met Lys Val Lys Leu Arg Leu Asp Asn Met Pro
1               5                   10                  15

Glu Ile Arg Ala Gly Leu Trp Lys Leu His Thr Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Tyr Lys Thr
    50                  55                  60

Ala Glu Glu Cys Lys Ala Glu Leu Leu Glu Arg Leu Arg Ala Arg Gln
65                  70                  75                  80
```

Val Glu Asn Gly His Cys Gly Pro Ala Gly Ser Asp Glu Leu Leu
                85                  90                  95

Gln Leu Ala Arg Gln Leu Tyr Glu Leu Leu Val Pro Gln Ala Ile Gly
                100                 105                 110

Ala Lys Gly Asp Ala Gln Gln Ile Ala Arg Lys Phe Leu Ser Pro Leu
            115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Ala Lys Ala Glu Ala Arg Lys Ser Thr Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Asp Met Ser Ser Val Gln Trp Lys Pro Leu Arg
        195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Glu
225                 230                 235                 240

Ala Tyr Ala Lys Leu Val Glu Gln Lys Ser Arg Phe Glu Gln Lys Asn
                245                 250                 255

Phe Val Gly Gln Glu His Leu Val Gln Leu Val Asn Gln Leu Gln Gln
            260                 265                 270

Asp Met Lys Glu Ala Ser His Gly Leu Glu Ser Lys Glu Gln Thr Ala
    275                 280                 285

His Tyr Leu Thr Gly Arg Ala Leu Arg Gly Ser Asp Lys Val Phe Glu
290                 295                 300

Lys Trp Glu Lys Leu Asp Pro Asp Ala Pro Phe Asp Leu Tyr Asp Thr
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Lys Tyr Gln Ala Leu Trp Arg
            340                 345                 350

Glu Asp Ala Ser Phe Leu Thr Arg Tyr Ala Val Tyr Asn Ser Ile Val
        355                 360                 365

Arg Lys Leu Asn His Ala Lys Met Phe Ala Thr Phe Thr Leu Pro Asp
370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Gly Arg His
                405                 410                 415

Ala Ile Arg Phe Gln Lys Leu Leu Thr Val Glu Asp Gly Val Ala Lys
            420                 425                 430

Glu Val Asp Asp Val Thr Val Pro Ile Ser Met Ser Ala Gln Leu Asp
        435                 440                 445

Asp Leu Leu Pro Arg Asp Pro His Glu Leu Val Ala Leu Tyr Phe Gln
450                 455                 460

Asp Tyr Gly Ala Glu Gln His Leu Ala Gly Glu Phe Gly Gly Ala Lys
465                 470                 475                 480

Ile Gln Tyr Arg Arg Asp Gln Leu Asn His Leu His Ala Arg Arg Gly
                485                 490                 495

-continued

Ala Arg Asp Val Tyr Leu Asn Leu Ser Val Arg Val Gln Ser Gln Ser
            500                 505                 510

Glu Ala Arg Gly Glu Arg Pro Pro Tyr Ala Ala Val Phe Arg Leu
            515                 520                 525

Val Gly Asp Asn His Arg Ala Phe Val His Phe Asp Lys Leu Ser Asp
            530                 535                 540

Tyr Leu Ala Glu His Pro Asp Gly Lys Leu Gly Ser Glu Gly Leu
545                 550                 555                 560

Leu Ser Gly Leu Arg Val Met Ser Val Asp Leu Gly Leu Arg Thr Ser
            565                 570                 575

Ala Ser Ile Ser Val Phe Arg Val Ala Arg Lys Asp Glu Leu Lys Pro
            580                 585                 590

Asn Ser Glu Gly Arg Val Pro Phe Cys Phe Pro Ile Glu Gly Asn Glu
            595                 600                 605

Asn Leu Val Ala Val His Glu Arg Ser Gln Leu Leu Lys Leu Pro Gly
            610                 615                 620

Glu Thr Glu Ser Lys Asp Leu Arg Ala Ile Arg Glu Gly Arg Gln Arg
625                 630                 635                 640

Thr Leu Arg Gln Leu Arg Thr Gln Leu Ala Tyr Leu Arg Leu Leu Val
            645                 650                 655

Arg Cys Gly Ser Glu Asp Val Gly Arg Arg Glu Arg Ser Trp Ala Lys
            660                 665                 670

Leu Ile Glu Gln Pro Met Asp Ala Asn Gln Met Thr Pro Asp Trp Arg
            675                 680                 685

Glu Ala Phe Glu Asp Glu Leu Gln Lys Leu Lys Ser Leu Tyr Gly Ile
            690                 695                 700

Cys Gly Asp Arg Glu Trp Thr Glu Ala Val Tyr Glu Ser Val Arg Arg
705                 710                 715                 720

Val Trp Arg His Met Gly Lys Gln Val Arg Asp Trp Arg Lys Asp Val
            725                 730                 735

Arg Ser Gly Glu Arg Pro Lys Ile Arg Gly Tyr Gln Lys Asp Val Val
            740                 745                 750

Gly Gly Asn Ser Ile Glu Gln Ile Glu Tyr Leu Glu Arg Gln Tyr Lys
            755                 760                 765

Phe Leu Lys Ser Trp Ser Phe Phe Gly Lys Val Ser Gly Gln Val Ile
            770                 775                 780

Ala Ala Glu Lys Gly Ser Arg Phe Ala Ile Thr Leu Arg Glu His Ile
785                 790                 795                 800

Asp His Ala Lys Glu Asp Arg Leu Lys Lys Leu Ala Asp Arg Ile Ile
            805                 810                 815

Met Glu Ala Leu Gly Tyr Val Tyr Ala Leu Asp Asp Glu Arg Gly Lys
            820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
            850                 855                 860

Asn Gln Leu Met Gln Trp Ser His Arg Gly Val Phe Gln Glu Leu Leu
865                 870                 875                 880

Asn Gln Ala Gln Val His Asp Leu Leu Val Gly Thr Met Tyr Ala Ala
            885                 890                 895

Phe Ser Ser Arg Phe Asp Ala Arg Thr Gly Ala Pro Gly Ile Arg Cys
            900                 905                 910

Arg Arg Val Pro Ala Arg Cys Ala Arg Glu Gln Asn Pro Glu Pro Phe

```
                915                 920                 925
Pro Trp Trp Leu Asn Lys Phe Val Ala Glu His Lys Leu Asp Gly Cys
    930                 935                 940

Pro Leu Arg Ala Asp Asp Leu Ile Pro Thr Gly Gly Glu Phe Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Arg Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Pro Val Leu Ile Pro Arg Thr Thr Gly Lys Arg Thr Ala Asp
    1010                1015                1020

Ser Tyr Gly Asn Lys Val Phe Tyr Thr Lys Thr Gly Val Thr Tyr
    1025                1030                1035

Tyr Glu Arg Glu Arg Gly Lys Lys Arg Arg Lys Val Phe Ala Gln
    1040                1045                1050

Glu Glu Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asp Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Arg Leu Gln Glu Ser Ala Cys Glu Asn Thr Gly Asp
    1115                1120                1125

Ile

<210> SEQ ID NO 5
<211> LENGTH: 1147
<212> TYPE: PRT
<213> ORGANISM: Alicyclobacillus kakegawensis

<400> SEQUENCE: 5

Met Ala Val Lys Ser Ile Lys Val Lys Leu Arg Leu Ser Glu Cys Pro
1               5                   10                  15

Asp Ile Leu Ala Gly Met Trp Gln Leu His Arg Ala Thr Asn Ala Gly
            20                  25                  30

Val Arg Tyr Tyr Thr Glu Trp Val Ser Leu Met Arg Gln Glu Ile Leu
        35                  40                  45

Tyr Ser Arg Gly Pro Asp Gly Gly Gln Gln Cys Tyr Met Thr Ala Glu
    50                  55                  60

Asp Cys Gln Arg Glu Leu Leu Arg Arg Leu Arg Asn Arg Gln Leu His
65                  70                  75                  80

Asn Gly Arg Gln Asp Gln Pro Gly Thr Asp Ala Asp Leu Leu Ala Ile
                85                  90                  95

Ser Arg Arg Leu Tyr Glu Ile Leu Val Leu Gln Ser Ile Gly Lys Arg
            100                 105                 110

Gly Asp Ala Gln Gln Ile Ala Ser Ser Phe Leu Ser Pro Leu Val Asp
        115                 120                 125

Pro Asn Ser Lys Gly Gly Arg Gly Glu Ala Lys Ser Gly Arg Lys Pro
    130                 135                 140

Ala Trp Gln Lys Met Arg Asp Gln Gly Asp Pro Arg Trp Val Ala Ala
```

```
                145                 150                 155                 160
Arg Glu Lys Tyr Glu Gln Arg Lys Ala Val Asp Pro Ser Lys Glu Ile
                    165                 170                 175

Leu Asn Ser Leu Asp Ala Leu Gly Leu Arg Pro Leu Phe Ala Val Phe
                    180                 185                 190

Thr Glu Thr Tyr Arg Ser Gly Val Asp Trp Lys Pro Leu Gly Lys Ser
                    195                 200                 205

Gln Gly Val Arg Thr Trp Asp Arg Asp Met Phe Gln Gln Ala Leu Glu
                    210                 215                 220

Arg Leu Met Ser Trp Glu Ser Trp Asn Arg Arg Val Gly Glu Glu Tyr
225                 230                 235                 240

Ala Arg Leu Phe Gln Gln Lys Met Lys Phe Glu Gln Glu His Phe Ala
                    245                 250                 255

Glu Gln Ser His Leu Val Lys Leu Ala Arg Ala Leu Glu Ala Asp Met
                    260                 265                 270

Arg Ala Ala Ser Gln Gly Phe Glu Ala Lys Arg Gly Thr Ala His Gln
                    275                 280                 285

Ile Thr Arg Arg Ala Leu Arg Gly Ala Asp Arg Val Phe Glu Ile Trp
                    290                 295                 300

Lys Ser Ile Pro Glu Glu Ala Leu Phe Ser Gln Tyr Asp Glu Val Ile
305                 310                 315                 320

Arg Gln Val Gln Ala Glu Lys Arg Arg Asp Phe Gly Ser His Asp Leu
                    325                 330                 335

Phe Ala Lys Leu Ala Glu Pro Lys Tyr Gln Pro Leu Trp Arg Ala Asp
                    340                 345                 350

Glu Thr Phe Leu Thr Arg Tyr Ala Leu Tyr Asn Gly Val Leu Arg Asp
                    355                 360                 365

Leu Glu Lys Ala Arg Gln Phe Ala Thr Phe Thr Leu Pro Asp Ala Cys
                    370                 375                 380

Val Asn Pro Ile Trp Thr Arg Phe Glu Ser Ser Gln Gly Ser Asn Leu
385                 390                 395                 400

His Lys Tyr Glu Phe Leu Phe Asp His Leu Gly Pro Gly Arg His Ala
                    405                 410                 415

Val Arg Phe Gln Arg Leu Leu Val Val Glu Ser Glu Gly Ala Lys Glu
                    420                 425                 430

Arg Asp Ser Val Val Pro Val Ala Pro Ser Gly Gln Leu Asp Lys
                    435                 440                 445

Leu Val Leu Arg Glu Glu Lys Ser Ser Val Ala Leu His Leu His
                    450                 455                 460

Asp Thr Ala Arg Pro Asp Gly Phe Met Ala Glu Trp Ala Gly Ala Lys
465                 470                 475                 480

Leu Gln Tyr Glu Arg Ser Thr Leu Ala Arg Ala Arg Arg Asp Lys
                    485                 490                 495

Gln Gly Met Arg Ser Trp Arg Arg Gln Pro Ser Met Leu Met Ser Ala
                    500                 505                 510

Ala Gln Met Leu Glu Asp Ala Lys Gln Ala Gly Asp Val Tyr Leu Asn
                    515                 520                 525

Ile Ser Val Arg Val Lys Ser Pro Ser Glu Val Arg Gly Gln Arg Arg
                    530                 535                 540

Pro Pro Tyr Ala Ala Leu Phe Arg Ile Asp Asp Lys Gln Arg Arg Val
545                 550                 555                 560

Thr Val Asn Tyr Asn Lys Leu Ser Ala Tyr Leu Glu Glu His Pro Asp
                    565                 570                 575
```

```
Lys Gln Ile Pro Gly Ala Pro Gly Leu Leu Ser Gly Leu Arg Val Met
            580                 585                 590

Ser Val Asp Leu Gly Leu Arg Thr Ser Ala Ser Ile Ser Val Phe Arg
        595                 600                 605

Val Ala Lys Lys Glu Glu Val Glu Ala Leu Gly Asp Gly Arg Pro Pro
610                 615                 620

His Tyr Tyr Pro Ile His Gly Thr Asp Asp Leu Val Ala Val His Glu
625                 630                 635                 640

Arg Ser His Leu Ile Gln Met Pro Gly Glu Thr Glu Thr Lys Gln Leu
                645                 650                 655

Arg Lys Leu Arg Glu Glu Arg Gln Ala Val Leu Arg Pro Leu Phe Ala
            660                 665                 670

Gln Leu Ala Leu Leu Arg Leu Leu Val Arg Cys Gly Ala Ala Asp Glu
        675                 680                 685

Arg Ile Arg Thr Arg Ser Trp Gln Arg Leu Thr Lys Gln Gly Arg Glu
    690                 695                 700

Phe Thr Lys Arg Leu Thr Pro Ser Trp Arg Glu Ala Leu Glu Leu Glu
705                 710                 715                 720

Leu Thr Arg Leu Glu Ala Tyr Cys Gly Arg Val Pro Asp Asp Glu Trp
                725                 730                 735

Ser Arg Ile Val Asp Arg Thr Val Ile Ala Leu Trp Arg Arg Met Gly
            740                 745                 750

Lys Gln Val Arg Asp Trp Arg Lys Gln Val Lys Ser Gly Ala Lys Val
        755                 760                 765

Lys Val Lys Gly Tyr Gln Leu Asp Val Val Gly Gly Asn Ser Leu Ala
    770                 775                 780

Gln Ile Asp Tyr Leu Glu Gln Gln Tyr Lys Phe Leu Arg Arg Trp Ser
785                 790                 795                 800

Phe Phe Ala Arg Ala Ser Gly Leu Val Val Arg Ala Asp Arg Glu Ser
                805                 810                 815

His Phe Ala Val Ala Leu Arg Gln His Ile Glu Asn Ala Lys Arg Asp
            820                 825                 830

Arg Leu Lys Lys Leu Ala Asp Arg Ile Leu Met Glu Ala Leu Gly Tyr
        835                 840                 845

Val Tyr Glu Ala Ser Gly Pro Arg Glu Gly Gln Trp Thr Ala Gln His
    850                 855                 860

Pro Pro Cys Gln Leu Ile Ile Leu Glu Glu Leu Ser Ala Tyr Arg Phe
865                 870                 875                 880

Ser Asp Asp Arg Pro Pro Ser Glu Asn Ser Lys Leu Met Ala Trp Gly
                885                 890                 895

His Arg Gly Ile Leu Glu Glu Leu Val Asn Gln Ala Gln Val His Asp
            900                 905                 910

Val Leu Val Gly Thr Val Tyr Ala Ala Phe Ser Ser Arg Phe Asp Ala
        915                 920                 925

Arg Thr Gly Ala Pro Gly Val Arg Cys Arg Arg Val Pro Ala Arg Phe
    930                 935                 940

Val Gly Ala Thr Val Asp Asp Ser Leu Pro Leu Trp Leu Thr Glu Phe
945                 950                 955                 960

Leu Asp Lys His Arg Leu Asp Lys Asn Leu Leu Arg Pro Asp Asp Val
                965                 970                 975

Ile Pro Thr Gly Glu Gly Glu Phe Leu Val Ser Pro Cys Gly Glu Glu
            980                 985                 990
```

```
Ala Ala Arg Val Arg Gln Val His Ala Asp Ile Asn Ala Ala Gln Asn
            995                1000                1005

Leu Gln Arg Arg Leu Trp Gln Asn Phe Asp Ile Thr Glu Leu Arg
    1010                1015                1020

Leu Arg Cys Asp Val Lys Met Gly Gly Glu Gly Thr Val Leu Val
    1025                1030                1035

Pro Arg Val Asn Asn Ala Arg Ala Lys Gln Leu Phe Gly Lys Lys
    1040                1045                1050

Val Leu Val Ser Gln Asp Gly Val Thr Phe Phe Glu Arg Ser Gln
    1055                1060                1065

Thr Gly Gly Lys Pro His Ser Glu Lys Gln Thr Asp Leu Thr Asp
    1070                1075                1080

Lys Glu Leu Glu Leu Ile Ala Glu Ala Asp Glu Ala Arg Ala Lys
    1085                1090                1095

Ser Val Val Leu Phe Arg Asp Pro Ser Gly His Ile Gly Lys Gly
    1100                1105                1110

His Trp Ile Arg Gln Arg Glu Phe Trp Ser Leu Val Lys Gln Arg
    1115                1120                1125

Ile Glu Ser His Thr Ala Glu Arg Ile Arg Val Arg Gly Val Gly
    1130                1135                1140

Ser Ser Leu Asp
    1145

<210> SEQ ID NO 6
<211> LENGTH: 3441
<212> TYPE: DNA
<213> ORGANISM: Alicyclobacillus kakegawensis

<400> SEQUENCE: 6
atggctgtaa aatctattaa ggtcaagttg cggttgtcag agtgcccaga catcctggct      60
ggcatgtggc agctccaccg ggcgacaaac gcggggttc gatactacac agaatgggtg     120
agcttgatgc gccaggagat cctctactcg cgcgggccgg acggcggtca gcagtgctac     180
atgaccgcgg aggattgcca acgcgagctg ctgcggcggc tgcgcaatcg ccagctccat     240
aatggccgcc aggaccagcc cggtacagat gcagacctac tggcaatcag taggagactc     300
tatgaaattc tggtcctgca atccatcggc aagagggggg acgcccagca gatagcgagc     360
agcttcctca gccctctggt cgatccgaac tccaaggtg ggcggggtga agccaagtcc     420
ggtcgaaagc ctgcgtggca gaagatgcgc gatcaaggtg atcctcgttg ggttgcggca     480
agggaaaagt acgagcaacg caaggcggtt gatccatcta agaaaatcct gaattcattg     540
gacgccctgg gtctcaggcc gctatttgcg gtcttcacgg agacctacag gtcgggagtc     600
gattggaagc cgctcggcaa agccaaggt gtgcgcacat gggaccgtga catgttccag     660
caggccctcg agcgcctgat gtcctgggag tcttggaacc gccgcgtggg cgaggagtac     720
gcccgtcttt tccaacagaa gatgaagttc gagcaggaac acttcgcgga acagtctcat     780
ctggttaaac tggcgcgcgc gttggaggcg acatgcgcg ccgcttcaca gggcttcgaa     840
gccaaacgcg gcactgcgca ccagatcaca agacgggcgc tgcgcggggc ggatcgggta     900
tttgagatat ggaagagtat tccagaggaa gctttgttct cccaatatga tgaagtgatt     960
cgacaggtcc aggcggagaa aagacgggac tttgggtccc atgatctgtt cgccaagttg    1020
gcggaaccga gtatcagcc cctgtggcgc gccgacgaga ccttttttgac gcgctacgcc    1080 ctgtacaatg gagtcttgcg ggatttagag aaagcgagac agttcgccac gttcacgctg    1140
```

-continued

```
ccggatgcct gcgtcaatcc aatttggacg cgttttgaaa gcagccaggg gagcaatctg      1200
cataaatatg aatttctctt tgaccacctg ggacccggac ggcacgcggt gcgttttcag      1260
aggctgctgg tggtagagag cgaaggtgcg aaggagaggg actcggtggt ggtgccagtc      1320
gcgccatccg ggcaactgga caagcttgtc ctgcgtgaag aagagaaatc aagcgttgcc      1380
ttacaccttc atgacacagc ccggccggac ggtttcatgg cagaatgggc gggggcgaag      1440
ctgcaatatg aacgcagtac cttggcacgc aaggcgcgcc gtgataagca agggatgcgg      1500
tcgtggcgta ggcagccgtc tatgctgatg tctgcggcac agatgttgga agacgcaaag      1560
caagccggag acgtgtatct gaacatcagt gtgcgtgtga agagcccag tgaagtccgc       1620 ggccagaggc ggcctcctta cgcggccctg tttcggatag acgataaaca gcggcgtgtg      1680
accgtaaatt acaacaaact gtcggcttac ctagaggaac atccggataa acagattcca      1740
ggcgcacctg ggctcctttc cggtcttcgg gtaatgagcg tcgaccttgg gttgcgcacc      1800
tccgcttcca tcagtgtgtt ccgtgtggca aagaaggaag aggtggaagc gctgggcgac      1860
ggtcgtcccc ctcattatta tcccatccat ggcactgacg acctggtggc ggtgcacgag      1920
cgctcacatt tgattcaaat gccaggcgaa accgaaacga aacagctgcg caagttgcgt      1980
gaggaacggc aggctgtctt gcgtccactg ttcgctcaac tggccctgct acggttgctg      2040
gtccggtgtg gtgcagccga cgagcggatt cgtacacgca gttggcagcg cttgacgaag      2100
caggggcgtg agtttacgaa gcgattgacg ccgtcctggc gggaggcgtt ggaattggag      2160
ttaactcgct tggaggcgta ttgcggtagg gttccagacg acgaatggag ccgcatcgtt      2220
gatagaacgg taatcgcttt gtggcgtcgc atgggaaaac aggtgcgcga ttggcgtaaa      2280
caggtgaaat ccggtgcgaa agtcaaggtc aaggggtacc agctggatgt agtcggcggc      2340
aactcgctgg cgcaaatcga ttatctcgaa cagcagtaca agtttctgcg gcgctggagc      2400
ttctttgcgc gggccagcgg tctggttgtg cgggcggatc gcgaatcgca tttcgcagtc      2460
gctttacgcc agcacattga aaatgccaag cgggatcggc tgaaaaagtt ggcggaccgc      2520
atcctgatgg aggcgctggg ctacgtgtat gaagcttccg ggccgcgcga aggacagtgg      2580
acggcgcagc atccgccgtg ccagttgatt atcttggagg aattaagcgc gtaccggttc      2640
agtgacgacc gtccgccgag cgagaacagt aaattgatgg cttgggggca tcgggaatt      2700 ttggaggagt tggtcaacca agcacaggtt cacgacgtgt tagtggggac ggtgtacgcc      2760 gcttttttcgt cccgcttcga tgcccgcaca ggcgcccctg gagtgcgctg ccgccgggta      2820
cccgcacgtt ttgtcggcgc gacggtggat gattcactgc cgctttggct cacagagttt      2880
ctggacaagc acaggctgga taaaaacctc ctgcggcctg acgatgtgat tccgaccgga      2940
gagggtgagt ttttggtttc tccgtgtggc gaggaagcgg ctcgggttcg gcaggtgcac      3000
gccgacatca acgcggcgca aaacctgcag cggaggctgt ggcagaattt tgacattaca      3060
gagctgcgtc tgcgctgcga tgtgaagatg ggtggcgaag aacggtgct ggtaccaagg       3120 gtcaacaacg cccgcgccaa acaactgttt ggaaagaagg tgttggtttc gcaagatggc      3180
gtgacgttct ttgaacgcag tcaaacaggt gggaaaccgc acagcgagaa gcagacggat      3240
ttgaccgaca aggaactaga actaattgcg gaggcggacg aggcgcgcgc caagtcggtc      3300
gtcctctttc gcgatccgtc cggcacatc ggcaagggcc actggattcg ccaaagggag       3360
ttttggtcgt tggtgaagca aaggattgaa tcgcacacgg cggaaaggat acgggttcgc      3420
ggcgtcggta gctcgctgga t                                                3441
```

-continued

<210> SEQ ID NO 7
<211> LENGTH: 3441
<212> TYPE: DNA
<213> ORGANISM: Artificial Sequence
<220> FEATURE:
<223> OTHER INFORMATION: Humanized AkC2c1 coding sequence

<400> SEQUENCE: 7

| | |
|---|---|
| atggccgtga agagcatcaa ggtgaagctg cgcctgagcg agtgccccga catcctggcc | 60 |
| ggcatgtggc agctgcaccg cgccaccaac gccggcgtgc gctactacac cgagtgggtg | 120 |
| agcctgatgc cgcaggagat cctgtacagc cgcggccccg acggcggcca gcagtgctac | 180 |
| atgaccgccg aggactgcca gcgcgagctg ctgcgccgcc tgcgcaaccg ccagctgcac | 240 |
| aacggccgcc aggaccagcc cggcaccgac gccgacctgc tggccatcag ccgccgcctg | 300 |
| tacgagatcc tggtgctgca gagcatcggc aagcgcggcg acgcccagca gatcgccagc | 360 |
| agcttcctga ccccctggt ggaccccaac agcaagggcg ccgcggcga ggccaagagc | 420 |
| ggccgcaagc ccgcctggca gaagatgcgc gaccagggcg accccgctg ggtggccgcc | 480 |
| cgcgagaagt acgagcagcg caaggccgtg gacccccagca aggagatcct gaacagcctg | 540 |
| gacgccctgg gcctgcgccc cctgttcgcc gtgttcaccg agacctaccg cagcggcgtg | 600 |
| gactggaagc ccctgggcaa gagccagggc gtgcgcacct gggaccgcga catgttccag | 660 |
| caggccctgg agcgcctgat gagctgggag agctggaacc gccgcgtggg cgaggagtac | 720 |
| gcccgcctgt tccagcagaa gatgaagttc gagcaggagc acttcgccga gcagagccac | 780 |
| ctggtgaagc tggcccgcgc cctggaggcc gacatgcgcg ccgccagcca gggcttcgag | 840 |
| gccaagcgcg gcaccgccca ccagatcacc cgccgcgccc tgcgcggcgc cgaccgcgtg | 900 |
| ttcgagatct ggaagagcat ccccgaggag gccctgttca gccagtacga cgaggtgatc | 960 |
| cgccaggtgc aggccgagaa cgccgcgac ttcggcagca cgacctgtt cgccaagctg | 1020 |
| gccgagccca gtaccagcc cctgtggcgc ccgacgaga ccttcctgac ccgctacgcc | 1080 |
| ctgtacaacg gcgtgctgcg cgacctggag aaggcccgcc agttcgccac cttcaccctg | 1140 |
| cccgacgcct gcgtgaaccc catctggacc cgcttcgaga gcagccaggg cagcaacctg | 1200 |
| cacaagtacg agttcctgtt cgaccacctg ggccccggcc gcacgccgt cgcttccag | 1260 |
| cgcctgctgg tggtggagag cgagggcgcc aaggagcgcg acagcgtggt ggtgcccgtg | 1320 |
| gccccagcg ccagctgga caagctggtg ctgcgcgagg aggagaagag cagcgtggcc | 1380 |
| ctgcacctgc acgacaccgc cgccccgac ggcttcatgg ccgagtgggc cggcgccaag | 1440 |
| ctgcagtacg agcgcagcac cctggcccgc aaggcccgcc gcgacaagca gggcatgcgc | 1500 |
| agctggcgcc gccagcccag catgctgatg agccgcgccc agatgctgga ggacgccaag | 1560 |
| caggccggcg acgtgtacct gaacatcagc gtgcgcgtga agagcccag cgaggtgcgc | 1620 |
| ggccagcgcc gcccccccta cgccgccctg ttccgcatcg acgacaagca gccgcgtg | 1680 |
| accgtgaact acaacaagct gagcgcctac ctggaggagc ccccgacaa gcagatcccc | 1740 |
| ggcgcccccg gctgctgag cggcctgcgc gtgatgagcg tggacctggg cctgcgcacc | 1800 |
| agcgccagca tcagcgtgtt ccgcgtggcc aagaaggagg aggtggaggc cctgggcgac | 1860 |
| ggccgccccc cccactacta ccccatccac ggcaccgacg acctggtggc cgtgcacgag | 1920 |
| cgcagccacc tgatccagat gccggcgag accgagacca gcagctgcg caagctgcgc | 1980 |
| gaggagcgcc aggccgtgct cgccccctg ttcgcccagc tggccctgct cgcctgctg | 2040 |
| gtgcgctgcg cgccgccga cgagcgcatc cgcacccgca gctggcagcg cctgaccaag | 2100 |

```
cagggccgcg agttcaccaa gcgcctgacc cccagctggc gcgaggccct ggagctggag   2160
ctgacccgcc tggaggccta ctgcggccgc gtgcccgacg acgagtggag ccgcatcgtg   2220
gaccgcaccg tgatcgccct gtggcgccgc atgggcaagc aggtgcgcga ctggcgcaag   2280
caggtgaaga gcggcgccaa ggtgaaggtg aagggctacc agctggacgt ggtgggcggc   2340
aacagcctgg cccagatcga ctacctggag cagcagtaca agttcctgcg ccgctggagc   2400
ttcttcgccc gcgccagcgg cctggtggtg cgcgccgacc gcgagagcca cttcgccgtg   2460

gccctgcgcc agcacatcga gaacgccaag cgcgaccgcc tgaagaagct ggccgaccgc   2520
atcctgatgg aggccctggg ctacgtgtac gaggccagcg gcccccgcga gggccagtgg   2580
accgcccagc acccccctg ccagctgatc atcctggagg agctgagcgc ctaccgcttc   2640
agcgacgacc gcccccccag cgagaacagc aagctgatgg cctggggcca ccgcggcatc   2700
ctggaggagc tggtgaacca ggcccaggtg cacgacgtgc tggtgggcac cgtgtacgcc   2760
gccttcagca gccgcttcga cgcccgcacc ggcgcccccg gcgtgcgctg ccgccgcgtg   2820
cccgcccgct tcgtgggcgc caccgtggac gacagcctgc ccctgtggct gaccgagttc   2880
ctggacaagc accgcctgga caagaacctg ctgcgccccg acgacgtgat ccccaccggc   2940
gagggcgagt tcctggtgag cccctgcggc gaggaggccg cccgcgtgcg ccaggtgcac   3000
gccgacatca acgccgccca gaacctgcag cgccgcctgt ggcagaactt cgacatcacc   3060
gagctgcgcc tgcgctgcga cgtgaagatg ggcggcgagg gcaccgtgct ggtgccccgc   3120
gtgaacaacg cccgcgccaa gcagctgttc ggcaagaagg tgctggtgag ccaggacggc   3180
gtgaccttct tcgagcgcag ccagaccggc ggcaagcccc acagcgagaa gcagaccgac   3240
ctgaccgaca aggagctgga gctgatcgcc gaggccgacg aggcccgcgc caagagcgtg   3300
gtgctgttcc gcgaccccag cggccacatc ggcaagggcc actggatccg ccagcgcgag   3360
ttctggagcc tggtgaagca gcgcatcgag agccacaccg ccgagcgcat ccgcgtgcgc   3420
ggcgtgggca gcagcctgga c                                              3441
```

<210> SEQ ID NO 8
<211> LENGTH: 2870
<212> TYPE: DNA
<213> ORGANISM: Artificial Sequence
<220> FEATURE:
<223> OTHER INFORMATION: pCAG-2AeGFP partial sequence

<400> SEQUENCE: 8

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg ggtcgaggtg agccccacgt tctgcttcac tctccccatc    420
tcccccccct ccccaccccc aattttgtat ttatttattt tttaattatt ttgtgcagcg    480
atgggggcgg gggggggggg ggcgcgcgcc aggcggggcg gggcggggcg aggggcgggg    540
cggggcgagg cggagaggtg cggcggcagc caatcagagc ggcgcgctcc gaaagtttcc    600
ttttatggcg aggcggcggc ggcggcggcc ctataaaaag cgaagcgcgc ggcgggcggg    660
agtcgctgcg ttgccttcgc cccgtgcccc gctccgcgcc gcctcgcgcc gcccgccccg    720
```

```
gctctgactg accgcgttac tcccacaggt gagcgggcgg gacgcccttc ctcctccggg      780
ctgtaattag cgcttggttt aatgacggct cgtttctttt ctgtggctgc gtgaaagcct      840
taaagggctc cgggagggcc ctttgtgcgg gggggagcgg ctcgggggg t gcgtgcgtgt     900 gtgtgtgcgt ggggagcgcc gcgtgcggcc cgcgctgccc ggcggctgtg agcgctgcgg      960
gcgcggcgcg gggctttgtg cgctccgcgt gtgcgcgagg ggagcgcggc cggggcggt     1020 gccccgcggt gcgggggggc tgcgagggga acaaaggctg cgtgcggggt gtgtgcgtgg     1080
gggggtgagc aggggg tgtg ggcgcggcgg tcggg ctgta accccccct gcacccccct    1140 ccccgagttg ctgagcacgg cccggcttcg ggtgcgggc tccgtacggg gcgtggcgcg     1200
gggctcgccg tgccgggcgg ggggtggcgg caggtgggg g tgccgggcgg ggcggggccg    1260
cctcgggccg gggagggctc gggggagggg cgcggcggcc cccggagcgc cggcggctgt     1320
cgaggcgcgg cgagccgcag ccattgcctt ttatggtaat cgtgcgagag ggcgcaggga     1380
cttcctttgt cccaaatctg tgcggagccg aaatctggga ggcgccgccg cacccctct     1440 agcgggcgcg gggcgaagcg gtgcggcgcc ggcaggaagg aaatgggcgg ggagggcctt    1500
cgtgcgtcgc cgcgccgccg tcccctttctc catctccagc ctcggggctg tccgcaggg g   1560 gacggctgcc ttcggggggg acgggcagg gcggggttcg gcttctggcg tgtgaccggc     1620
ggctctagcg cctctgctaa ccatgttcat gccttcttct ttttcctaca gctcctgggc     1680
aacgtgctgg ttattgtgct gtctcatcat tttggcaaag ctagtgaatt ctaatacgac     1740
tcactatagg ccgccaccat gcccaagaag aagaggaagg ttcccgggg c tagcccaaag    1800 aagaagagga aagtctctag ataccctttat gatgttccag attatgccgg atacccatac    1860
gatgtccctg actatgcagg ctcctaccct tatgacgtcc cagactacgc cggatccagg    1920
tccggcggcg gagagggcag aggaagtctt ctaacatgcg gtgacgtgga ggagaatccc    1980 ggccca atgg tgagcaaggg cgaggagctg ttcaccgggg tggtgcccat cctggtcgag    2040
ctggacggcg acgtaaacgg ccacaagttc agcgtgtccg gcgagggcga gggcgatgcc    2100
acctacggca agctgaccct gaagttcatc tgcaccaccg gcaagctgcc cgtgccctgg    2160
cccaccctcg tgaccaccct gacctacggc gtgcagtgct tcagccgcta ccccgaccac    2220
atgaagcagc acgacttctt caagtccgcc atgcccgaag gctacgtcca ggagcgcacc    2280
atcttcttca aggacgacgg caactacaag acccgcgccg aggtgaagtt cgagggcgac    2340
accctggtga accgcatcga gctgaagggc atcgacttca aggaggacgg caacatcctg    2400
gggcacaagc tggagtacaa ctacaacagc cacaacgtct atatcatggc cgacaagcag    2460
aagaacggca tcaaggtgaa cttcaagatc cgccacaaca tcgaggacgg cagcgtgcag    2520
ctcgccgacc actaccagca gaacaccccc atcggcgacg gccccgtgct gctgcccgac    2580
aaccactacc tgagcaccca gtccgccctg agcaaagacc ccaacgagaa gcgcgatcac    2640
atggtcctgc tggagttcgt gaccgccgcc gggatcactc tcggcatgga cgagctgtac    2700
aagtaactgc agcgcgggga tctcatgctg gagttcttcg cccaccccaa cttgtttatt    2760
gcagcttata atggttacaa ataaagcaat agcatcacaa atttcacaaa taaagcattt    2820
ttttcactgc attctagttg tggtttgtcc aaactcatca atgtatctta               2870
```

<210> SEQ ID NO 9
<211> LENGTH: 1533
<212> TYPE: DNA
<213> ORGANISM: Artificial Sequence
<220> FEATURE:

<223> OTHER INFORMATION: BPK2104-ccdB partial sequence

<400> SEQUENCE: 9

```
tcactgcccg ctttccagtc gggaaacctg tcgtgccagc tgcattaatg aatcggccaa     60
cgcgcgggga gaggcggttt gcgtattggg cgccagggtg ttttttcttt tcaccagtga    120
gacgggcaac agctgattgc ccttcaccgc ctggccctga gagagttgca gcaagcggtc    180
cacgctggtt tgccccagca ggcgaaaatc ctgtttgatg gtggttaacg gcgggatata    240
acatgagctg tcttcggtat cgtcgtatcc cactaccgag atgtccgcac caacgcgcag    300
cccggactcg gtaatggcgc gcattgcgcc cagcgccatc tgatcgttgg caaccagcat    360
cgcagtggga acgatgccct cattcagcat ttgcatggtt tgttgaaaac cggacatggc    420
actccagtcg ccttcccgtt ccgctatcgg ctgaatttga ttgcgagtga gatatttatg    480
ccagccagcc agacgcagac gcgccgagac agaacttaat gggcccgcta acagcgcgat    540
ttgctggtga cccaatgcga ccagatgctc cacgcccagt cgcgtaccgt cttcatggga    600
gaaaataata ctgttgatgg tgtctggtc agagacatca agaaataacg ccggaacatt    660
agtgcaggca gcttccacag caatggcatc ctggtcatcc agcggatagt taatgatcag    720
cccactgacg cgttgcgcga agattgtg caccgccgct ttacaggctt cgacgccgct    780
tcgttctacc atcgacacca ccacgctggc acccagttga tcggcgcgag atttaatcgc    840
cgcgacaatt tgcgacggcg cgtgcaggc cagactggag gtggcaacgc caatcagcaa    900
cgactgtttg cccgccagtt gttgtgccac gcggttggga atgtaattca gctccgccat    960
cgccgcttcc acttttttccc gcgttttcgc agaaacgtgg ctggcctggt tcaccacgcg   1020
ggaaacggtc tgataagaga caccggcata ctctgcgaca tcgtataacg ttactggttt   1080
cacattcacc accctgaatt gactctcttc cgggcgctat catgccatac cgcgaaaggt   1140
tttgcgccat tcgatggtgt ccgggatctc gacgctctcc cttatgcgac tcctgcatta   1200
ggaaattaat acgactcact ataggggaat tgtgagcgga taacaattcc cctgtagaaa   1260
taattttgtt tactttaat aaggagatat catatgccca agaagaagag gaaggttccc   1320
ggggctagtc atcaccatca ccaccatcat caccatcact aggcggccgc ataatgctta   1380
agtcgaacag aaagtaatcg tattgtacac ggccgcataa tcgaaattaa tacgactcac   1440
tatagggaat tcgtacctg agaataacta gcataacccc ttggggcctc taaacgggtc   1500
ttgaggggtt ttttgctgaa acctcaggca ttt                                1533
```

<210> SEQ ID NO 10
<211> LENGTH: 410
<212> TYPE: DNA
<213> ORGANISM: Artificial Sequence
<220> FEATURE:
<223> OTHER INFORMATION: pUC19-U6 partial sequence
<220> FEATURE:
<221> NAME/KEY: misc_feature
<222> LOCATION: (283)..(289)
<223> OTHER INFORMATION: n is a, c, g, or t
<220> FEATURE:
<221> NAME/KEY: misc_feature
<222> LOCATION: (297)..(375)
<223> OTHER INFORMATION: n is a, c, g, or t

<400> SEQUENCE: 10

```
tgtaaaacga cggccagtga attcgagggc ctatttccca tgattccttc atatttgcat     60
atacgataca aggctgttag agagataatt ggaattaatt tgactgtaaa cacaaagata    120
ttagtacaaa atacgtgacg tagaaagtaa aatttcttg ggtagtttgc agttttaaaa    180
```

```
ttatgtttta aaatggacta tcatatgctt accgtaactt gaaagtattt cgatttcttg      240
gctttatata tcttgtggaa aggacgaaac accggagaga ccnnnnnnng gtctcannnn      300
nnnnnnnnnn nnnnnnnnnn nnnnnnnnnn nnnnnnnnnn nnnnnnnnnn nnnnnnnnnn      360
nnnnnnnnnn nnnnnaagct tggcgtaatc atggtcatag ctgtttcctg                 410
```

<210> SEQ ID NO 11
<211> LENGTH: 476
<212> TYPE: DNA
<213> ORGANISM: Artificial Sequence
<220> FEATURE:
<223> OTHER INFORMATION: pUC19-U6-AasgRNA1 partial sequence

<400> SEQUENCE: 11

```
tgtaaaacga cggccagtga attcgagggc ctatttccca tgattccttc atatttgcat       60
atacgataca aggctgttag agagataatt ggaattaatt tgactgtaaa cacaaagata      120
ttagtacaaa atacgtgacg tagaaagtaa taatttcttg ggtagtttgc agttttaaaa      180
ttatgtttta aaatggacta tcatatgctt accgtaactt gaaagtattt cgatttcttg      240
gctttatata tcttgtggaa aggacgaaac accgggtcta aaggacagaa ttttcaacg      300 ggtgtgccaa tggccacttt ccaggtggca agcccgttg aacttctcaa aaagaacgct      360
cgctcagtgt tctgacgtcg gatcactgag cgagcgatct gagaagtggc acagagaccg      420
agagagggtc tcatttttt taagcttggc gtaatcatgg tcatagctgt ttcctg          476
```

<210> SEQ ID NO 12
<211> LENGTH: 476
<212> TYPE: DNA
<213> ORGANISM: Artificial Sequence
<220> FEATURE:
<223> OTHER INFORMATION: pUC19-U6-AksgRNA partial sequence

<400> SEQUENCE: 12

```
tgtaaaacga cggccagtga attcgagggc ctatttccca tgattccttc atatttgcat       60
atacgataca aggctgttag agagataatt ggaattaatt tgactgtaaa cacaaagata      120
ttagtacaaa atacgtgacg tagaaagtaa taatttcttg ggtagtttgc agttttaaaa      180
ttatgtttta aaatggacta tcatatgctt accgtaactt gaaagtattt cgatttcttg      240
gctttatata tcttgtggaa aggacgaaac accggtcgtc tataggacgg cgaggacaac      300
gggaagtgcc aatgtgctct ttccaagagc aaacaccccg ttggcttcaa gatgaccgct      360
cgctcagcga tctgacaacg gatcgctgag cgagcggtct gagaagtggc acagagaccg      420
agagagggtc tcatttttt taagcttggc gtaatcatgg tcatagctgt ttcctg          476
```

<210> SEQ ID NO 13
<211> LENGTH: 484
<212> TYPE: DNA
<213> ORGANISM: Artificial Sequence
<220> FEATURE:
<223> OTHER INFORMATION: pUC19-U6-AmsgRNA partial sequence

<400> SEQUENCE: 13

```
tgtaaaacga cggccagtga attcgagggc ctatttccca tgattccttc atatttgcat       60
atacgataca aggctgttag agagataatt ggaattaatt tgactgtaaa cacaaagata      120
ttagtacaaa atacgtgacg tagaaagtaa taatttcttg ggtagtttgc agttttaaaa      180
ttatgtttta aaatggacta tcatatgctt accgtaactt gaaagtattt cgatttcttg      240
```

```
gctttatata tcttgtggaa aggacgaaac accggggaat tgccgatcta taggacggca    300
gattcaacgg gatgtgccaa tgcactcttt ccaggagtga acaccccgtt ggcttcaaca    360
tgatcgcccg ctcaacggtc cgatgtcgga tcgttgagcg ggcgatctga aagtggcac    420 agagaccgag agagggtctc atttttttta agcttggcgt aatcatggtc atagctgttt    480
cctg                                                                484
```

```
<210> SEQ ID NO 14
<211> LENGTH: 471
<212> TYPE: DNA
<213> ORGANISM: Artificial Sequence
<220> FEATURE:
<223> OTHER INFORMATION: pUC19-U6-BssgRNA partial sequence

<400> SEQUENCE: 14
tgtaaaacga cggccagtga attcgagggc ctatttccca tgattccttc atatttgcat     60
atacgataca aggctgttag agagataatt ggaattaatt tgactgtaaa cacaaagata    120
ttagtacaaa atacgtgacg tagaaagtaa taatttcttg ggtagtttgc agttttaaaa    180
ttatgtttta aaatggacta tcatatgctt accgtaactt gaaagtattt cgatttcttg    240
gctttatata tcttgtggaa aggacgaaac accggccata agtcgactta catatccgtg    300
cgtgtgcatt atgggcccat ccacaggtct attcccacgg ataatcacga ctttccacta    360
agctttcgaa tgttcgaaag cttagtggaa agcttcgtgg ttagcacaga gaccgagaga    420
gggtctcatt tttttaagc ttggcgtaat catggtcata gctgtttcct g              471
```

```
<210> SEQ ID NO 15
<211> LENGTH: 101
<212> TYPE: DNA
<213> ORGANISM: Artificial Sequence
<220> FEATURE:
<223> OTHER INFORMATION: tracrRNA

<400> SEQUENCE: 15
gtctaaagga cagaattttt caacgggtgt gccaatggcc actttccagg tggcaaagcc     60
cgttgaactt ctcaaaaaga acgctcgctc agtgttctga c                        101
```

```
<210> SEQ ID NO 16
<211> LENGTH: 71
<212> TYPE: DNA
<213> ORGANISM: Artificial Sequence
<220> FEATURE:
<223> OTHER INFORMATION: crRNA
<220> FEATURE:
<221> NAME/KEY: misc_feature
<222> LOCATION: (37)..(54)
<223> OTHER INFORMATION: n is a, c, g, or t
<220> FEATURE:
<221> NAME/KEY: misc_feature
<222> LOCATION: (55)..(71)
<223> OTHER INFORMATION: n is optionally not present
<220> FEATURE:
<221> NAME/KEY: misc_feature
<222> LOCATION: (160)..(176)
<223> OTHER INFORMATION: n is optionally not present

<400> SEQUENCE: 16
gtcggatcac tgagcgagcg atctgagaag tggcacnnnn nnnnnnnnnn nnnnnnnnnn     60
nnnnnnnnnn n                                                          71
```

```
<210> SEQ ID NO 17
<211> LENGTH: 172
```

```
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (138)..(154)
<223> OTHER INFORMATION: n is a, c, g, or t
<220> FEATURE:
<221> NAME/KEY: misc_feature
<222> LOCATION: (155)..(172)
<223> OTHER INFORMATION: n is optionally not present

<400> SEQUENCE: 17
gtctaaagga cagaattttt caacgggtgt gccaatggcc actttccagg tggcaaagcc      60
cgttgaactt ctcaaaaaga acgctcgctc agtgttctga cgtcggatca ctgagcgagc     120
gatctgagaa gtggcacnnn nnnnnnnnnn nnnnnnnnnn nnnnnnnnnn nn             172

<210> SEQ ID NO 18
<211> LENGTH: 176
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (142)..(159)
<223> OTHER INFORMATION: n is a, c, g, or t
<220> FEATURE:
<221> NAME/KEY: misc_feature
<222> LOCATION: (160)..(176)
<223> OTHER INFORMATION: n is optionally not present

<400> SEQUENCE: 18
aactgtctaa aggacagaat ttttcaacgg gtgtgccaat ggccactttc caggtggcaa      60
agcccgttga acttctcaaa agaacgctc gctcagtgtt ctgacgtcgg atcactgagc     120
gagcgatctg agaagtggca cnnnnnnnnn nnnnnnnnnn nnnnnnnnnn nnnnn          176

<210> SEQ ID NO 19
<211> LENGTH: 174
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (140)..(157)
<223> OTHER INFORMATION: n is a, c, g, or t
<220> FEATURE:
<221> NAME/KEY: misc_feature
<222> LOCATION: (158)..(174)
<223> OTHER INFORMATION: n is optionally not present

<400> SEQUENCE: 19
ctgtctaaag gacagaattt ttcaacgggt gtgccaatgg ccactttcca ggtggcaaag      60
cccgttgaac ttctcaaaaa gaacgctcgc tcagtgttct gacgtcggat cactgagcga    120
gcgatctgag aagtggcacn nnnnnnnnnn nnnnnnnnnn nnnnnnnnnn nnnn           174

<210> SEQ ID NO 20
<211> LENGTH: 162
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (128)..(144)
```

<223> OTHER INFORMATION: n is a, c, g, or t
<220> FEATURE:
<221> NAME/KEY: misc_feature
<222> LOCATION: (145)..(162)
<223> OTHER INFORMATION: n is optionally not present

<400> SEQUENCE: 20
gtctaaagga cagaattttt caacgggtgt gccaatggcc actttccagg tggcaaagcc    60
cgttgaactt ctcaaaaaga acgctcgctc agtgttatca ctgagcgagc gatctgagaa   120
gtggcacnnn nnnnnnnnnn nnnnnnnnnn nnnnnnnnnn nn                      162

<210> SEQ ID NO 21
<211> LENGTH: 134
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (100)..(116)
<223> OTHER INFORMATION: n is a, c, g, or t
<220> FEATURE:
<221> NAME/KEY: misc_feature
<222> LOCATION: (117)..(134)
<223> OTHER INFORMATION: n is optionally not present

<400> SEQUENCE: 21
gtctaaagga cagaattttt caacgggtgt gccaatggcc actttccagg tggcaaagcc    60
cgttgaactt ctcaaaaaga acgatctgag aagtggcacn nnnnnnnnnn nnnnnnnnn    120 nnnnnnnnnn nnnn                                                     134

<210> SEQ ID NO 22
<211> LENGTH: 128
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (94)..(111)
<223> OTHER INFORMATION: n is a, c, g, or t
<220> FEATURE:
<221> NAME/KEY: misc_feature
<222> LOCATION: (112)..(128)
<223> OTHER INFORMATION: n is optionally not present

<400> SEQUENCE: 22
gtctaaagga cagaattttt caacgggtgt gccaatggcc actttccagg tggcaaagcc    60
cgttgaactt ctcaaaaagc tgagaagtgg cacnnnnnnn nnnnnnnnnn nnnnnnnnn    120 nnnnnnnn                                                            128

<210> SEQ ID NO 23
<211> LENGTH: 126
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (92)..(109)
<223> OTHER INFORMATION: n is a, c, g, or t
<220> FEATURE:
<221> NAME/KEY: misc_feature
<222> LOCATION: (110)..(126)
<223> OTHER INFORMATION: n is optionally not present

<400> SEQUENCE: 23

```
gtctaaagga cagaattttt caacgggtgt gccaatggcc actttccagg tggcaaagcc    60
cgttgaactt ctcaaagctg agaagtggca cnnnnnnnnn nnnnnnnnnn nnnnnnnnnn   120 nnnnnn                                                             126
```

<210> SEQ ID NO 24
<211> LENGTH: 126
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (92)..(109)
<223> OTHER INFORMATION: n is a, c, g, or t
<220> FEATURE:
<221> NAME/KEY: misc_feature
<222> LOCATION: (110)..(126)
<223> OTHER INFORMATION: n is optionally not present

<400> SEQUENCE: 24

```
gtctaaagga cagaattttt caacgggtgt gccaatggcc actttccagg tggcaaagcc    60
cgttgaactt ctcaaaactg agaagtggca cnnnnnnnnn nnnnnnnnnn nnnnnnnnnn   120 nnnnnn                                                             126
```

<210> SEQ ID NO 25
<211> LENGTH: 124
<212> TYPE: DNA
<213> ORGANISM: Artificial Sequence
<220> FEATURE:
<223> OTHER INFORMATION: sgRNA
<220> FEATURE:
<221> NAME/KEY: misc_feature
<222> LOCATION: (90)..(107)
<223> OTHER INFORMATION: n is a, c, g, or t
<220> FEATURE:
<221> NAME/KEY: misc_feature
<222> LOCATION: (108)..(124)
<223> OTHER INFORMATION: n is optionally not present

<400> SEQUENCE: 25

```
gtctaaagga cagaattttt caacgggtgt gccaatggcc actttccagg tggcaaagcc    60
cgttgaactt ctcaagcgag aagtggcacn nnnnnnnnn nnnnnnnnnn nnnnnnnnnn    120 nnnn                                                               124
```

<210> SEQ ID NO 26
<211> LENGTH: 87
<212> TYPE: DNA
<213> ORGANISM: Artificial Sequence
<220> FEATURE:
<223> OTHER INFORMATION: sgRNA

<400> SEQUENCE: 26

```
gtctaaagga cagaattttt caacgggtgt gccaatggcc actttccagg tggcaaagcc    60
cgttgaactt ctaagcagaa gtggcac                                       87
```

<210> SEQ ID NO 27
<211> LENGTH: 85
<212> TYPE: DNA
<213> ORGANISM: Artificial Sequence
<220> FEATURE:
<223> OTHER INFORMATION: sgRNA

<400> SEQUENCE: 27
gtctaaagga cagaattttt caacgggtgt gccaatggcc actttccagg tggcaaagcc      60
cgttgaactt caagcgaagt ggcac                                            85

<210> SEQ ID NO 28
<211> LENGTH: 60
<212> TYPE: DNA
<213> ORGANISM: Mus musculus

<400> SEQUENCE: 28
aattagtttc cctcccagtc ccttggctat catgatagcc aagggactgg gagggaaact      60

<210> SEQ ID NO 29
<211> LENGTH: 4
<212> TYPE: DNA
<213> ORGANISM: Mus musculus

<400> SEQUENCE: 29 tttc                                                                    4

<210> SEQ ID NO 30
<211> LENGTH: 58
<212> TYPE: DNA
<213> ORGANISM: Mus musculus

<400> SEQUENCE: 30
aattaattcc ctcccagtcc cttggctatc atgatagcca agggactggg agggaatt        58

<210> SEQ ID NO 31
<211> LENGTH: 4
<212> TYPE: DNA
<213> ORGANISM: Mus musculus

<400> SEQUENCE: 31 attc                                                                    4

<210> SEQ ID NO 32
<211> LENGTH: 58
<212> TYPE: DNA
<213> ORGANISM: Mus musculus

<400> SEQUENCE: 32
aattagttcc ctcccagtcc cttggctatc atgatagcca agggactggg agggaact        58

<210> SEQ ID NO 33
<211> LENGTH: 4
<212> TYPE: DNA
<213> ORGANISM: Mus musculus

<400> SEQUENCE: 33 gttc                                                                    4

<210> SEQ ID NO 34
<211> LENGTH: 58
<212> TYPE: DNA
<213> ORGANISM: Mus musculus

<400> SEQUENCE: 34
aattacttcc ctcccagtcc cttggctatc atgatagcca agggactggg agggaagt        58

<210> SEQ ID NO 35
<211> LENGTH: 4
<212> TYPE: DNA
<213> ORGANISM: Mus musculus

```
<400> SEQUENCE: 35 cttc                                                                    4

<210> SEQ ID NO 36
<211> LENGTH: 56
<212> TYPE: DNA
<213> ORGANISM: Mus musculus

<400> SEQUENCE: 36
aattgttccc tcccagtccc ttggctatca tgatagccaa gggactggga gggaac         56

<210> SEQ ID NO 37
<211> LENGTH: 3
<212> TYPE: DNA
<213> ORGANISM: Mus musculus

<400> SEQUENCE: 37 ttc                                                                     3

<210> SEQ ID NO 38
<211> LENGTH: 56
<212> TYPE: DNA
<213> ORGANISM: Mus musculus

<400> SEQUENCE: 38
aattataccc tcccagtccc ttggctatca tgatagccaa gggactggga gggtat         56

<210> SEQ ID NO 39
<211> LENGTH: 3
<212> TYPE: DNA
<213> ORGANISM: Mus musculus

<400> SEQUENCE: 39 tac                                                                     3

<210> SEQ ID NO 40
<211> LENGTH: 56
<212> TYPE: DNA
<213> ORGANISM: Mus musculus

<400> SEQUENCE: 40
aattatgccc tcccagtccc ttggctatca tgatagccaa gggactggga gggcat         56

<210> SEQ ID NO 41
<211> LENGTH: 3
<212> TYPE: DNA
<213> ORGANISM: Mus musculus

<400> SEQUENCE: 41 tgc                                                                     3

<210> SEQ ID NO 42
<211> LENGTH: 56
<212> TYPE: DNA
<213> ORGANISM: Mus musculus

<400> SEQUENCE: 42
aattatcccc tcccagtccc ttggctatca tgatagccaa gggactggga gggat          56

<210> SEQ ID NO 43
<211> LENGTH: 3
<212> TYPE: DNA
```

```
<213> ORGANISM: Mus musculus

<400> SEQUENCE: 43 tcc                                                                    3

<210> SEQ ID NO 44
<211> LENGTH: 56
<212> TYPE: DNA
<213> ORGANISM: Mus musculus

<400> SEQUENCE: 44
aattaatccc tcccagtccc ttggctatca tgatagccaa gggactggga gggatt        56

<210> SEQ ID NO 45
<211> LENGTH: 3
<212> TYPE: DNA
<213> ORGANISM: Mus musculus

<400> SEQUENCE: 45 atc                                                                    3

<210> SEQ ID NO 46
<211> LENGTH: 56
<212> TYPE: DNA
<213> ORGANISM: Mus musculus

<400> SEQUENCE: 46
aattagtccc tcccagtccc ttggctatca tgatagccaa gggactggga gggact        56

<210> SEQ ID NO 47
<211> LENGTH: 3
<212> TYPE: DNA
<213> ORGANISM: Mus musculus

<400> SEQUENCE: 47 gtc                                                                    3

<210> SEQ ID NO 48
<211> LENGTH: 56
<212> TYPE: DNA
<213> ORGANISM: Mus musculus

<400> SEQUENCE: 48
aattactccc tcccagtccc ttggctatca tgatagccaa gggactggga gggagt        56

<210> SEQ ID NO 49
<211> LENGTH: 3
<212> TYPE: DNA
<213> ORGANISM: Mus musculus

<400> SEQUENCE: 49 ctc                                                                    3

<210> SEQ ID NO 50
<211> LENGTH: 56
<212> TYPE: DNA
<213> ORGANISM: Mus musculus

<400> SEQUENCE: 50
aattaaaccc tcccagtccc ttggctatca tgatagccaa gggactggga gggttt        56

<210> SEQ ID NO 51
<211> LENGTH: 3
```

```
<212> TYPE: DNA
<213> ORGANISM: Mus musculus

<400> SEQUENCE: 51 aac                                                                        3

<210> SEQ ID NO 52
<211> LENGTH: 56
<212> TYPE: DNA
<213> ORGANISM: Mus musculus

<400> SEQUENCE: 52
aattaggccc tcccagtccc ttggctatca tgatagccaa gggactggga gggcct            56

<210> SEQ ID NO 53
<211> LENGTH: 3
<212> TYPE: DNA
<213> ORGANISM: Mus musculus

<400> SEQUENCE: 53 ggc                                                                        3

<210> SEQ ID NO 54
<211> LENGTH: 56
<212> TYPE: DNA
<213> ORGANISM: Mus musculus

<400> SEQUENCE: 54
aattaccccc tcccagtccc ttggctatca tgatagccaa gggactggga gggggt            56

<210> SEQ ID NO 55
<211> LENGTH: 3
<212> TYPE: DNA
<213> ORGANISM: Mus musculus

<400> SEQUENCE: 55 ccc                                                                        3

<210> SEQ ID NO 56
<211> LENGTH: 56
<212> TYPE: DNA
<213> ORGANISM: Mus musculus

<400> SEQUENCE: 56
aattattgcc tcccagtccc ttggctatca tgatagccaa gggactggga ggcaat            56

<210> SEQ ID NO 57
<211> LENGTH: 3
<212> TYPE: DNA
<213> ORGANISM: Mus musculus

<400> SEQUENCE: 57 ttg                                                                        3

<210> SEQ ID NO 58
<211> LENGTH: 56
<212> TYPE: DNA
<213> ORGANISM: Mus musculus

<400> SEQUENCE: 58
aattattacc tcccagtccc ttggctatca tgatagccaa gggactggga ggtaat            56

<210> SEQ ID NO 59
```

```
<211> LENGTH: 3
<212> TYPE: DNA
<213> ORGANISM: Mus musculus

<400> SEQUENCE: 59 tta                                                                        3

<210> SEQ ID NO 60
<211> LENGTH: 56
<212> TYPE: DNA
<213> ORGANISM: Mus musculus

<400> SEQUENCE: 60
aattatttcc tcccagtccc ttggctatca tgatagccaa gggactggga ggaaat          56

<210> SEQ ID NO 61
<211> LENGTH: 3
<212> TYPE: DNA
<213> ORGANISM: Mus musculus

<400> SEQUENCE: 61 ttt                                                                        3

<210> SEQ ID NO 62
<211> LENGTH: 25
<212> TYPE: DNA
<213> ORGANISM: artificial sequence
<220> FEATURE:
<223> OTHER INFORMATION: RNF2-F

<400> SEQUENCE: 62
ggagctgtag gcgattatag ttgaa                                               25

<210> SEQ ID NO 63
<211> LENGTH: 24
<212> TYPE: DNA
<213> ORGANISM: artificial sequence
<220> FEATURE:
<223> OTHER INFORMATION: RNF2-R

<400> SEQUENCE: 63
ttctcaaacc ctggaaagca cttt                                                24

<210> SEQ ID NO 64
<211> LENGTH: 25
<212> TYPE: DNA
<213> ORGANISM: artificial sequence
<220> FEATURE:
<223> OTHER INFORMATION: CD34-F

<400> SEQUENCE: 64
ttgaaatgag tttggtcagg gatgg                                               25

<210> SEQ ID NO 65
<211> LENGTH: 25
<212> TYPE: DNA
<213> ORGANISM: artificial sequence
<220> FEATURE:
<223> OTHER INFORMATION: CD34-R

<400> SEQUENCE: 65
aactgtgtat ttccgtgctg attcc                                               25

<210> SEQ ID NO 66
<211> LENGTH: 24
```

```
<212> TYPE: DNA
<213> ORGANISM: artificial sequence
<220> FEATURE:
<223> OTHER INFORMATION: Nrl-F

<400> SEQUENCE: 66
gcctctcagt gttctacacc ttcc                                          24

<210> SEQ ID NO 67
<211> LENGTH: 24
<212> TYPE: DNA
<213> ORGANISM: artificial sequence
<220> FEATURE:
<223> OTHER INFORMATION: Nrl-R

<400> SEQUENCE: 67
ccatagagac aggaccctgg ttct                                          24

<210> SEQ ID NO 68
<211> LENGTH: 20
<212> TYPE: DNA
<213> ORGANISM: artificial sequence
<220> FEATURE:
<223> OTHER INFORMATION: Apob-F

<400> SEQUENCE: 68
cgtgcccttt ggacctttgg                                               20

<210> SEQ ID NO 69
<211> LENGTH: 25
<212> TYPE: DNA
<213> ORGANISM: artificial sequence
<220> FEATURE:
<223> OTHER INFORMATION: Apob-R

<400> SEQUENCE: 69
ggagccctca caacctaaat tatct                                         25

<210> SEQ ID NO 70
<211> LENGTH: 20
<212> TYPE: DNA
<213> ORGANISM: Homo sapiens

<400> SEQUENCE: 70
tggaaacaca aactcttctg                                               20

<210> SEQ ID NO 71
<211> LENGTH: 4
<212> TYPE: DNA
<213> ORGANISM: Homo sapiens

<400> SEQUENCE: 71 ttta                                                                 4

<210> SEQ ID NO 72
<211> LENGTH: 20
<212> TYPE: DNA
<213> ORGANISM: Homo sapiens

<400> SEQUENCE: 72
agacctttca accactagca                                               20

<210> SEQ ID NO 73
<211> LENGTH: 4
<212> TYPE: DNA
```

```
<213> ORGANISM: Homo sapiens

<400> SEQUENCE: 73 tttc                                                              4

<210> SEQ ID NO 74
<211> LENGTH: 20
<212> TYPE: DNA
<213> ORGANISM: Homo sapiens

<400> SEQUENCE: 74
aactccagag acaaccttga                                             20

<210> SEQ ID NO 75
<211> LENGTH: 4
<212> TYPE: DNA
<213> ORGANISM: Homo sapiens

<400> SEQUENCE: 75 tttc                                                              4

<210> SEQ ID NO 76
<211> LENGTH: 20
<212> TYPE: DNA
<213> ORGANISM: Homo sapiens

<400> SEQUENCE: 76
aaccactagc actagccttg                                             20

<210> SEQ ID NO 77
<211> LENGTH: 4
<212> TYPE: DNA
<213> ORGANISM: Homo sapiens

<400> SEQUENCE: 77 tttc                                                              4

<210> SEQ ID NO 78
<211> LENGTH: 20
<212> TYPE: DNA
<213> ORGANISM: Homo sapiens

<400> SEQUENCE: 78
cataaactga ggttatcaca                                             20

<210> SEQ ID NO 79
<211> LENGTH: 4
<212> TYPE: DNA
<213> ORGANISM: Homo sapiens

<400> SEQUENCE: 79 tttc                                                              4

<210> SEQ ID NO 80
<211> LENGTH: 20
<212> TYPE: DNA
<213> ORGANISM: Homo sapiens

<400> SEQUENCE: 80
tgtttccata aactgaggtt                                             20

<210> SEQ ID NO 81
<211> LENGTH: 4
```

```
<212> TYPE: DNA
<213> ORGANISM: Homo sapiens

<400> SEQUENCE: 81 tttg                                                                4

<210> SEQ ID NO 82
<211> LENGTH: 20
<212> TYPE: DNA
<213> ORGANISM: Homo sapiens

<400> SEQUENCE: 82
caggtgacag gctaggcttc                                              20

<210> SEQ ID NO 83
<211> LENGTH: 4
<212> TYPE: DNA
<213> ORGANISM: Homo sapiens

<400> SEQUENCE: 83 tttc                                                                4

<210> SEQ ID NO 84
<211> LENGTH: 20
<212> TYPE: DNA
<213> ORGANISM: Homo sapiens

<400> SEQUENCE: 84
gtgggagatg ttgcaaggct                                              20

<210> SEQ ID NO 85
<211> LENGTH: 4
<212> TYPE: DNA
<213> ORGANISM: Homo sapiens

<400> SEQUENCE: 85 ttta                                                                4

<210> SEQ ID NO 86
<211> LENGTH: 20
<212> TYPE: DNA
<213> ORGANISM: Homo sapiens

<400> SEQUENCE: 86
acatctacct ctgtgataac                                              20

<210> SEQ ID NO 87
<211> LENGTH: 3
<212> TYPE: DNA
<213> ORGANISM: Homo sapiens

<400> SEQUENCE: 87 ttc                                                                 3

<210> SEQ ID NO 88
<211> LENGTH: 20
<212> TYPE: DNA
<213> ORGANISM: Homo sapiens

<400> SEQUENCE: 88
atggaaacac aaactcttct                                              20

<210> SEQ ID NO 89
```

```
<211> LENGTH: 3
<212> TYPE: DNA
<213> ORGANISM: Homo sapiens

<400> SEQUENCE: 89 ttt                                                                        3

<210> SEQ ID NO 90
<211> LENGTH: 20
<212> TYPE: DNA
<213> ORGANISM: Homo sapiens

<400> SEQUENCE: 90
tgtccagtca cagacctctg                                                     20

<210> SEQ ID NO 91
<211> LENGTH: 3
<212> TYPE: DNA
<213> ORGANISM: Homo sapiens

<400> SEQUENCE: 91 ttc                                                                        3

<210> SEQ ID NO 92
<211> LENGTH: 20
<212> TYPE: DNA
<213> ORGANISM: Homo sapiens

<400> SEQUENCE: 92
accaccccag ccaacgtttc                                                     20

<210> SEQ ID NO 93
<211> LENGTH: 3
<212> TYPE: DNA
<213> ORGANISM: Homo sapiens

<400> SEQUENCE: 93 ttc                                                                        3

<210> SEQ ID NO 94
<211> LENGTH: 20
<212> TYPE: DNA
<213> ORGANISM: Homo sapiens

<400> SEQUENCE: 94
aagcctagcc tgtcacctgg                                                     20

<210> SEQ ID NO 95
<211> LENGTH: 3
<212> TYPE: DNA
<213> ORGANISM: Homo sapiens

<400> SEQUENCE: 95 ttg                                                                        3

<210> SEQ ID NO 96
<211> LENGTH: 20
<212> TYPE: DNA
<213> ORGANISM: Homo sapiens

<400> SEQUENCE: 96
cagacctttc aaccactagc                                                     20
```

```
<210> SEQ ID NO 97
<211> LENGTH: 3
<212> TYPE: DNA
<213> ORGANISM: Homo sapiens

<400> SEQUENCE: 97 ttt                                                                     3

<210> SEQ ID NO 98
<211> LENGTH: 20
<212> TYPE: DNA
<213> ORGANISM: Homo sapiens

<400> SEQUENCE: 98
caacatctcc cactaaaccc                                                  20

<210> SEQ ID NO 99
<211> LENGTH: 3
<212> TYPE: DNA
<213> ORGANISM: Homo sapiens

<400> SEQUENCE: 99 ttg                                                                     3

<210> SEQ ID NO 100
<211> LENGTH: 20
<212> TYPE: DNA
<213> ORGANISM: Homo sapiens

<400> SEQUENCE: 100
tcctatccta agtgacatca                                                  20

<210> SEQ ID NO 101
<211> LENGTH: 3
<212> TYPE: DNA
<213> ORGANISM: Homo sapiens

<400> SEQUENCE: 101 ttc                                                                     3

<210> SEQ ID NO 102
<211> LENGTH: 20
<212> TYPE: DNA
<213> ORGANISM: Homo sapiens

<400> SEQUENCE: 102
acctcgaagt ctacacagtg                                                  20

<210> SEQ ID NO 103
<211> LENGTH: 4
<212> TYPE: DNA
<213> ORGANISM: Homo sapiens

<400> SEQUENCE: 103 tttc                                                                    4

<210> SEQ ID NO 104
<211> LENGTH: 20
<212> TYPE: DNA
<213> ORGANISM: Homo sapiens

<400> SEQUENCE: 104
tttggatatg ttgaagaaca                                                  20
```

```
<210> SEQ ID NO 105
<211> LENGTH: 4
<212> TYPE: DNA
<213> ORGANISM: Homo sapiens

<400> SEQUENCE: 105 tttg                                                                     4

<210> SEQ ID NO 106
<211> LENGTH: 20
<212> TYPE: DNA
<213> ORGANISM: Homo sapiens

<400> SEQUENCE: 106
gatatgttga agaacaccat                                                   20

<210> SEQ ID NO 107
<211> LENGTH: 4
<212> TYPE: DNA
<213> ORGANISM: Homo sapiens

<400> SEQUENCE: 107 tttg                                                                     4

<210> SEQ ID NO 108
<211> LENGTH: 20
<212> TYPE: DNA
<213> ORGANISM: Homo sapiens

<400> SEQUENCE: 108
catcgttttt gtgcagactg                                                   20

<210> SEQ ID NO 109
<211> LENGTH: 4
<212> TYPE: DNA
<213> ORGANISM: Homo sapiens

<400> SEQUENCE: 109 ttta                                                                     4

<210> SEQ ID NO 110
<211> LENGTH: 20
<212> TYPE: DNA
<213> ORGANISM: Homo sapiens

<400> SEQUENCE: 110
gtgcagactg catcatcaca                                                   20

<210> SEQ ID NO 111
<211> LENGTH: 4
<212> TYPE: DNA
<213> ORGANISM: Homo sapiens

<400> SEQUENCE: 111 tttt                                                                     4

<210> SEQ ID NO 112
<211> LENGTH: 20
<212> TYPE: DNA
<213> ORGANISM: Homo sapiens

<400> SEQUENCE: 112
tgcagactgc atcatcacag                                                   20
```

```
<210> SEQ ID NO 113
<211> LENGTH: 4
<212> TYPE: DNA
<213> ORGANISM: Homo sapiens

<400> SEQUENCE: 113 tttg                                                                    4

<210> SEQ ID NO 114
<211> LENGTH: 20
<212> TYPE: DNA
<213> ORGANISM: Homo sapiens

<400> SEQUENCE: 114
aggcaataac agatggctta                                                  20

<210> SEQ ID NO 115
<211> LENGTH: 4
<212> TYPE: DNA
<213> ORGANISM: Homo sapiens

<400> SEQUENCE: 115 tttc                                                                    4

<210> SEQ ID NO 116
<211> LENGTH: 20
<212> TYPE: DNA
<213> ORGANISM: Homo sapiens

<400> SEQUENCE: 116
gttgaagaac accatgacta                                                  20

<210> SEQ ID NO 117
<211> LENGTH: 4
<212> TYPE: DNA
<213> ORGANISM: Homo sapiens

<400> SEQUENCE: 117 tttg                                                                    4

<210> SEQ ID NO 118
<211> LENGTH: 20
<212> TYPE: DNA
<213> ORGANISM: Homo sapiens

<400> SEQUENCE: 118
gaaattgtgg tttcacctcg                                                  20

<210> SEQ ID NO 119
<211> LENGTH: 3
<212> TYPE: DNA
<213> ORGANISM: Homo sapiens

<400> SEQUENCE: 119 tta                                                                     3

<210> SEQ ID NO 120
<211> LENGTH: 20
<212> TYPE: DNA
<213> ORGANISM: Homo sapiens

<400> SEQUENCE: 120
```

```
tggtttcacc tcgaagtcta                                            20

<210> SEQ ID NO 121
<211> LENGTH: 3
<212> TYPE: DNA
<213> ORGANISM: Homo sapiens

<400> SEQUENCE: 121 ttg                                                               3

<210> SEQ ID NO 122
<211> LENGTH: 20
<212> TYPE: DNA
<213> ORGANISM: Homo sapiens

<400> SEQUENCE: 122
cacctcgaag tctacacagt                                            20

<210> SEQ ID NO 123
<211> LENGTH: 3
<212> TYPE: DNA
<213> ORGANISM: Homo sapiens

<400> SEQUENCE: 123 ttt                                                               3

<210> SEQ ID NO 124
<211> LENGTH: 20
<212> TYPE: DNA
<213> ORGANISM: Homo sapiens

<400> SEQUENCE: 124
atgtgcccaa tttgtttgga                                            20

<210> SEQ ID NO 125
<211> LENGTH: 3
<212> TYPE: DNA
<213> ORGANISM: Homo sapiens

<400> SEQUENCE: 125 tta                                                               3

<210> SEQ ID NO 126
<211> LENGTH: 20
<212> TYPE: DNA
<213> ORGANISM: Homo sapiens

<400> SEQUENCE: 126
ggatatgttg aagaacacca                                            20

<210> SEQ ID NO 127
<211> LENGTH: 3
<212> TYPE: DNA
<213> ORGANISM: Homo sapiens

<400> SEQUENCE: 127 ttt                                                               3

<210> SEQ ID NO 128
<211> LENGTH: 20
<212> TYPE: DNA
<213> ORGANISM: Homo sapiens

<400> SEQUENCE: 128
```
ttgtgcagac tgcatcatca                                          20

<210> SEQ ID NO 129
<211> LENGTH: 3
<212> TYPE: DNA
<213> ORGANISM: Homo sapiens

<400> SEQUENCE: 129 ttt                                                             3

<210> SEQ ID NO 130
<211> LENGTH: 20
<212> TYPE: DNA
<213> ORGANISM: Homo sapiens

<400> SEQUENCE: 130
aagaacacca tgactacaaa                                          20

<210> SEQ ID NO 131
<211> LENGTH: 3
<212> TYPE: DNA
<213> ORGANISM: Homo sapiens

<400> SEQUENCE: 131 ttg                                                             3

<210> SEQ ID NO 132
<211> LENGTH: 20
<212> TYPE: DNA
<213> ORGANISM: Homo sapiens

<400> SEQUENCE: 132
gaagtgggta tgttgaaaag                                          20

<210> SEQ ID NO 133
<211> LENGTH: 3
<212> TYPE: DNA
<213> ORGANISM: Homo sapiens

<400> SEQUENCE: 133 tta                                                             3

<210> SEQ ID NO 134
<211> LENGTH: 20
<212> TYPE: DNA
<213> ORGANISM: Mus musculus

<400> SEQUENCE: 134
cctcccagtc ccttggctat                                          20

<210> SEQ ID NO 135
<211> LENGTH: 4
<212> TYPE: DNA
<213> ORGANISM: Mus musculus

<400> SEQUENCE: 135 tttc                                                            4

<210> SEQ ID NO 136
<211> LENGTH: 20
<212> TYPE: DNA
<213> ORGANISM: Mus musculus

```
<400> SEQUENCE: 136
atttgatgaa gttcgaaata                                               20

<210> SEQ ID NO 137
<211> LENGTH: 4
<212> TYPE: DNA
<213> ORGANISM: Mus musculus

<400> SEQUENCE: 137 tttg                                                                 4

<210> SEQ ID NO 138
<211> LENGTH: 20
<212> TYPE: DNA
<213> ORGANISM: Mus musculus

<400> SEQUENCE: 138
atgaagttcg aaataaagcg                                               20

<210> SEQ ID NO 139
<211> LENGTH: 4
<212> TYPE: DNA
<213> ORGANISM: Mus musculus

<400> SEQUENCE: 139 tttg                                                                 4

<210> SEQ ID NO 140
<211> LENGTH: 20
<212> TYPE: DNA
<213> ORGANISM: Mus musculus

<400> SEQUENCE: 140
gaacttcatc aaatcaaagt                                               20

<210> SEQ ID NO 141
<211> LENGTH: 4
<212> TYPE: DNA
<213> ORGANISM: Mus musculus

<400> SEQUENCE: 141 tttc                                                                 4

<210> SEQ ID NO 142
<211> LENGTH: 20
<212> TYPE: DNA
<213> ORGANISM: Mus musculus

<400> SEQUENCE: 142
tttcgaactt catcaaatca                                               20

<210> SEQ ID NO 143
<211> LENGTH: 4
<212> TYPE: DNA
<213> ORGANISM: Mus musculus

<400> SEQUENCE: 143 ttta                                                                 4

<210> SEQ ID NO 144
<211> LENGTH: 20
<212> TYPE: DNA
<213> ORGANISM: Mus musculus
```

```
<400> SEQUENCE: 144
tgagggccga tctggagtcc                                        20

<210> SEQ ID NO 145
<211> LENGTH: 3
<212> TYPE: DNA
<213> ORGANISM: Mus musculus

<400> SEQUENCE: 145 ttc                                                           3

<210> SEQ ID NO 146
<211> LENGTH: 20
<212> TYPE: DNA
<213> ORGANISM: Mus musculus

<400> SEQUENCE: 146
ggctccacac catacagctc                                        20

<210> SEQ ID NO 147
<211> LENGTH: 3
<212> TYPE: DNA
<213> ORGANISM: Mus musculus

<400> SEQUENCE: 147 ttg                                                           3

<210> SEQ ID NO 148
<211> LENGTH: 20
<212> TYPE: DNA
<213> ORGANISM: Mus musculus

<400> SEQUENCE: 148
atcaaatcaa agtcattaac                                        20

<210> SEQ ID NO 149
<211> LENGTH: 3
<212> TYPE: DNA
<213> ORGANISM: Mus musculus

<400> SEQUENCE: 149 ttc                                                           3

<210> SEQ ID NO 150
<211> LENGTH: 20
<212> TYPE: DNA
<213> ORGANISM: Mus musculus

<400> SEQUENCE: 150
taggaggagc tggcttaagg                                        20

<210> SEQ ID NO 151
<211> LENGTH: 4
<212> TYPE: DNA
<213> ORGANISM: Mus musculus

<400> SEQUENCE: 151 ttta                                                          4

<210> SEQ ID NO 152
<211> LENGTH: 20
<212> TYPE: DNA
```

<213> ORGANISM: Mus musculus

<400> SEQUENCE: 152
aaaagtgctc catttatagg                                                  20

<210> SEQ ID NO 153
<211> LENGTH: 4
<212> TYPE: DNA
<213> ORGANISM: Mus musculus

<400> SEQUENCE: 153 tttg                                                                    4

<210> SEQ ID NO 154
<211> LENGTH: 20
<212> TYPE: DNA
<213> ORGANISM: Mus musculus

<400> SEQUENCE: 154
ctggctgtgg cctggccacg                                                  20

<210> SEQ ID NO 155
<211> LENGTH: 3
<212> TYPE: DNA
<213> ORGANISM: Mus musculus

<400> SEQUENCE: 155 ttc                                                                     3

<210> SEQ ID NO 156
<211> LENGTH: 20
<212> TYPE: DNA
<213> ORGANISM: Mus musculus

<400> SEQUENCE: 156
gtgggcccat ggcggatgga                                                  20

<210> SEQ ID NO 157
<211> LENGTH: 4
<212> TYPE: DNA
<213> ORGANISM: Mus musculus

<400> SEQUENCE: 157 tttc                                                                    4

<210> SEQ ID NO 158
<211> LENGTH: 20
<212> TYPE: DNA
<213> ORGANISM: Mus musculus

<400> SEQUENCE: 158
caccctaact cacgagccca                                                  20

<210> SEQ ID NO 159
<211> LENGTH: 3
<212> TYPE: DNA
<213> ORGANISM: Mus musculus

<400> SEQUENCE: 159 ttc                                                                     3

<210> SEQ ID NO 160
<211> LENGTH: 20

```
<212> TYPE: DNA
<213> ORGANISM: Mus musculus

<400> SEQUENCE: 160
tcccaggctt ccaccctaac                                              20

<210> SEQ ID NO 161
<211> LENGTH: 4
<212> TYPE: DNA
<213> ORGANISM: Mus musculus

<400> SEQUENCE: 161 tttc                                                               4

<210> SEQ ID NO 162
<211> LENGTH: 20
<212> TYPE: DNA
<213> ORGANISM: Mus musculus

<400> SEQUENCE: 162
taccccagga tgtaactggt                                              20

<210> SEQ ID NO 163
<211> LENGTH: 4
<212> TYPE: DNA
<213> ORGANISM: Mus musculus

<400> SEQUENCE: 163 tttc                                                               4

<210> SEQ ID NO 164
<211> LENGTH: 20
<212> TYPE: DNA
<213> ORGANISM: Mus musculus

<400> SEQUENCE: 164 atcaccccccc gccccctccc                                             20

<210> SEQ ID NO 165
<211> LENGTH: 4
<212> TYPE: DNA
<213> ORGANISM: Mus musculus

<400> SEQUENCE: 165 tttc                                                               4

<210> SEQ ID NO 166
<211> LENGTH: 157
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (138)..(157)
<223> OTHER INFORMATION: n is a, c, g, or t

<400> SEQUENCE: 166
gtctaaagga cagaattttt caacgggtgt gccaatggcc actttccagg tggcaaagcc     60
cgttgaactt ctcaaaaaga acgctcgctc agtgttctga cgtcggatca ctgagcgagc    120
gatctgagaa gtggcacnnn nnnnnnnnn nnnnnn                              157

<210> SEQ ID NO 167
```

```
<211> LENGTH: 161
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (142)..(161)
<223> OTHER INFORMATION: n is a, c, g, or t

<400> SEQUENCE: 167
aactgtctaa aggacagaat ttttcaacgg gtgtgccaat ggccactttc caggtggcaa      60
agcccgttga acttctcaaa aagaacgctc gctcagtgtt ctgacgtcgg atcactgagc     120
gagcgatctg agaagtggca cnnnnnnnnn nnnnnnnnnn n                          161

<210> SEQ ID NO 168
<211> LENGTH: 159
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (140)..(159)
<223> OTHER INFORMATION: n is a, c, g, or t

<400> SEQUENCE: 168
ctgtctaaag gacagaattt ttcaacgggt gtgccaatgg ccactttcca ggtggcaaag      60
cccgttgaac ttctcaaaaa gaacgctcgc tcagtgttct gacgtcggat cactgagcga    120
gcgatctgag aagtggcacn nnnnnnnnnn nnnnnnnn                              159

<210> SEQ ID NO 169
<211> LENGTH: 155
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (136)..(155)
<223> OTHER INFORMATION: n is a, c, g, or t

<400> SEQUENCE: 169
ctaaaggaca gaattttca acgggtgtgc caatggccac tttccaggtg caaagcccg        60 ttgaacttct caaaagaac gctcgctcag tgttctgacg tcggatcact gagcgagcga    120
tctgagaagt ggcacnnnnn nnnnnnnnnn nnnnn                                 155

<210> SEQ ID NO 170
<211> LENGTH: 151
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (132)..(151)
<223> OTHER INFORMATION: n is a, c, g, or t

<400> SEQUENCE: 170
aggacagaat ttttcaacgg gtgtgccaat ggccactttc caggtggcaa agcccgttga      60
acttctcaaa aagaacgctc gctcagtgtt ctgacgtcgg atcactgagc gagcgatctg    120
agaagtggca cnnnnnnnnn nnnnnnnnnn n                                     151
```

```
<210> SEQ ID NO 171
<211> LENGTH: 147
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (128)..(147)
<223> OTHER INFORMATION: n is a, c, g, or t

<400> SEQUENCE: 171 cagaatttttt caacgggtgt gccaatggcc actttccagg tggcaaagcc cgttgaactt      60
ctcaaaaaga acgctcgctc agtgttctga cgtcggatca ctgagcgagc gatctgagaa     120
gtggcacnnn nnnnnnnnn nnnnnn                                           147

<210> SEQ ID NO 172
<211> LENGTH: 146
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (127)..(146)
<223> OTHER INFORMATION: n is a, c, g, or t

<400> SEQUENCE: 172
gtctaaagga cagaatttttt caacgggtgt gccaataggt ggcaaagccc gttgaacttc     60
tcaaaaagaa cgctcgctca gtgttctgac gtcggatcac tgagcgagcg atctgagaag    120
tggcacnnnn nnnnnnnnnn nnnnnn                                           146

<210> SEQ ID NO 173
<211> LENGTH: 133
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (114)..(133)
<223> OTHER INFORMATION: n is a, c, g, or t

<400> SEQUENCE: 173
gtctaaagga cagaatttttt caacgggtgt aaagcccgtt gaacttctca aaagaacgc     60 tcgctcagtg ttctgacgtc ggatcactga gcgagcgatc tgagaagtgg cacnnnnnnn    120
nnnnnnnnnn nnn                                                         133

<210> SEQ ID NO 174
<211> LENGTH: 147
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (128)..(147)
<223> OTHER INFORMATION: n is a, c, g, or t

<400> SEQUENCE: 174
gtctaaagga cagaatttttt caacgggtgt gccaatggcc actttccagg tggcaaagcc     60
cgttgaactt ctcaaaaaga acgctcgctc agtgttatca ctgagcgagc gatctgagaa    120
gtggcacnnn nnnnnnnnn nnnnnn                                           147
```

<210> SEQ ID NO 175
<211> LENGTH: 119
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (100)..(119)
<223> OTHER INFORMATION: n is a, c, g, or t

<400> SEQUENCE: 175
gtctaaagga cagaattttt caacgggtgt gccaatggcc actttccagg tggcaaagcc      60
cgttgaactt ctcaaaaaga acgatctgag aagtggcacn nnnnnnnnn nnnnnnnnn      119

<210> SEQ ID NO 176
<211> LENGTH: 113
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (94)..(113)
<223> OTHER INFORMATION: n is a, c, g, or t

<400> SEQUENCE: 176
gtctaaagga cagaattttt caacgggtgt gccaatggcc actttccagg tggcaaagcc      60
cgttgaactt ctcaaaaagc tgagaagtgg cacnnnnnnn nnnnnnnnnn nnn      113

<210> SEQ ID NO 177
<211> LENGTH: 111
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (92)..(111)
<223> OTHER INFORMATION: n is a, c, g, or t

<400> SEQUENCE: 177
gtctaaagga cagaattttt caacgggtgt gccaatggcc actttccagg tggcaaagcc      60
cgttgaactt ctcaaagctg agaagtggca cnnnnnnnnn nnnnnnnnnn n      111

<210> SEQ ID NO 178
<211> LENGTH: 111
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (92)..(111)
<223> OTHER INFORMATION: n is a, c, g, or t

<400> SEQUENCE: 178
gtctaaagga cagaattttt caacgggtgt gccaatggcc actttccagg tggcaaagcc      60
cgttgaactt ctcaaaactg agaagtggca cnnnnnnnnn nnnnnnnnnn n      111

<210> SEQ ID NO 179
<211> LENGTH: 109
<212> TYPE: DNA
<213> ORGANISM: artificial sequence
<220> FEATURE:
<223> OTHER INFORMATION: artificial sequence

```
<220> FEATURE:
<221> NAME/KEY: misc_feature
<222> LOCATION: (90)..(109)
<223> OTHER INFORMATION: n is a, c, g, or t

<400> SEQUENCE: 179
gtctaaagga cagaattttt caacgggtgt gccaatggcc actttccagg tggcaaagcc    60
cgttgaactt ctcaagcgag aagtggcacn nnnnnnnnnn nnnnnnnnn                 109

<210> SEQ ID NO 180
<211> LENGTH: 107
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (88)..(107)
<223> OTHER INFORMATION: n is a, c, g, or t

<400> SEQUENCE: 180
gtctaaagga cagaattttt caacgggtgt gccaatggcc actttccagg tggcaaagcc    60
cgttgaactt ctaagcagaa gtggcacnnn nnnnnnnnn nnnnnn                     107

<210> SEQ ID NO 181
<211> LENGTH: 105
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (86)..(105)
<223> OTHER INFORMATION: n is a, c, g, or t

<400> SEQUENCE: 181
gtctaaagga cagaattttt caacgggtgt gccaatggcc actttccagg tggcaaagcc    60
cgttgaactt caagcgaagt ggcacnnnnn nnnnnnnnn nnnnn                      105

<210> SEQ ID NO 182
<211> LENGTH: 23
<212> TYPE: DNA
<213> ORGANISM: Homo sapiens

<400> SEQUENCE: 182
ttgtagtcat ggtgttcttc aac                                             23

<210> SEQ ID NO 183
<211> LENGTH: 23
<212> TYPE: DNA
<213> ORGANISM: Homo sapiens

<400> SEQUENCE: 183
ttgttgtcat ggtgttccta ggg                                             23

<210> SEQ ID NO 184
<211> LENGTH: 23
<212> TYPE: DNA
<213> ORGANISM: Homo sapiens

<400> SEQUENCE: 184
ttttagtcat tgtattcttc agc                                             23

<210> SEQ ID NO 185
```

```
<211> LENGTH: 23
<212> TYPE: DNA
<213> ORGANISM: Homo sapiens

<400> SEQUENCE: 185
ttttagtcat ggttttctta ttc                                               23

<210> SEQ ID NO 186
<211> LENGTH: 23
<212> TYPE: DNA
<213> ORGANISM: Homo sapiens

<400> SEQUENCE: 186
ttttagtctt ggtgttttc aca                                                23

<210> SEQ ID NO 187
<211> LENGTH: 23
<212> TYPE: DNA
<213> ORGANISM: Homo sapiens

<400> SEQUENCE: 187
ttttagtcat gatgttctgt aaa                                               23

<210> SEQ ID NO 188
<211> LENGTH: 23
<212> TYPE: DNA
<213> ORGANISM: Homo sapiens

<400> SEQUENCE: 188
ttttattcat tgtgttcttc agc                                               23

<210> SEQ ID NO 189
<211> LENGTH: 23
<212> TYPE: DNA
<213> ORGANISM: Homo sapiens

<400> SEQUENCE: 189
ttttagtcaa ggtgttcagc ccc                                               23

<210> SEQ ID NO 190
<211> LENGTH: 23
<212> TYPE: DNA
<213> ORGANISM: Homo sapiens

<400> SEQUENCE: 190
ttttattcat tgtgttcttc agc                                               23

<210> SEQ ID NO 191
<211> LENGTH: 23
<212> TYPE: DNA
<213> ORGANISM: Homo sapiens

<400> SEQUENCE: 191
ttatagtcat ggtcttctat gtg                                               23

<210> SEQ ID NO 192
<211> LENGTH: 23
<212> TYPE: DNA
<213> ORGANISM: Homo sapiens

<400> SEQUENCE: 192
ttatagtcat gctgttcagt gtc                                               23
```

```
<210> SEQ ID NO 193
<211> LENGTH: 23
<212> TYPE: DNA
<213> ORGANISM: Homo sapiens

<400> SEQUENCE: 193
ttatagtcat tgtgttcctt cct                                              23

<210> SEQ ID NO 194
<211> LENGTH: 23
<212> TYPE: DNA
<213> ORGANISM: Homo sapiens

<400> SEQUENCE: 194
ttatagtaat ggtgttctta tta                                              23

<210> SEQ ID NO 195
<211> LENGTH: 23
<212> TYPE: DNA
<213> ORGANISM: Homo sapiens

<400> SEQUENCE: 195
ttataatcat ggtgctcttc aca                                              23

<210> SEQ ID NO 196
<211> LENGTH: 23
<212> TYPE: DNA
<213> ORGANISM: Homo sapiens

<400> SEQUENCE: 196
ttatagtaat ggtgttctca aaa                                              23

<210> SEQ ID NO 197
<211> LENGTH: 23
<212> TYPE: DNA
<213> ORGANISM: Homo sapiens

<400> SEQUENCE: 197
ttatagtcat tgtattcttc aat                                              23

<210> SEQ ID NO 198
<211> LENGTH: 23
<212> TYPE: DNA
<213> ORGANISM: Homo sapiens

<400> SEQUENCE: 198
ttatagtcat ggtattctta cat                                              23

<210> SEQ ID NO 199
<211> LENGTH: 23
<212> TYPE: DNA
<213> ORGANISM: Homo sapiens

<400> SEQUENCE: 199
ttatagtcat tgtgttcaaa aaa                                              23

<210> SEQ ID NO 200
<211> LENGTH: 23
<212> TYPE: DNA
<213> ORGANISM: Homo sapiens

<400> SEQUENCE: 200
ttatagtcat ggtcttctat gtg                                              23
```

```
<210> SEQ ID NO 201
<211> LENGTH: 23
<212> TYPE: DNA
<213> ORGANISM: Homo sapiens

<400> SEQUENCE: 201
ttctagtcat tgtgttcaga gga                                              23

<210> SEQ ID NO 202
<211> LENGTH: 23
<212> TYPE: DNA
<213> ORGANISM: Homo sapiens

<400> SEQUENCE: 202
ttctagtcct ggtgttctct cta                                              23

<210> SEQ ID NO 203
<211> LENGTH: 23
<212> TYPE: DNA
<213> ORGANISM: Homo sapiens

<400> SEQUENCE: 203
ttctagtcat ggagctcttc aca                                              23

<210> SEQ ID NO 204
<211> LENGTH: 23
<212> TYPE: DNA
<213> ORGANISM: Homo sapiens

<400> SEQUENCE: 204
ttctaatcat ggtgttctag aat                                              23

<210> SEQ ID NO 205
<211> LENGTH: 23
<212> TYPE: DNA
<213> ORGANISM: Homo sapiens

<400> SEQUENCE: 205
ttctagtcaa ggtgttctat ggc                                              23

<210> SEQ ID NO 206
<211> LENGTH: 23
<212> TYPE: DNA
<213> ORGANISM: Homo sapiens

<400> SEQUENCE: 206
ttctagtcat ggagttctaa cta                                              23

<210> SEQ ID NO 207
<211> LENGTH: 23
<212> TYPE: DNA
<213> ORGANISM: Homo sapiens

<400> SEQUENCE: 207
ttctattcat ggtgttcctt aag                                              23

<210> SEQ ID NO 208
<211> LENGTH: 23
<212> TYPE: DNA
<213> ORGANISM: Homo sapiens

<400> SEQUENCE: 208
ttctagacat ggtgttccat ttg                                              23
```

<210> SEQ ID NO 209
<211> LENGTH: 23
<212> TYPE: DNA
<213> ORGANISM: Homo sapiens

<400> SEQUENCE: 209
ttctagtcat tgtgttttc agt                                    23

<210> SEQ ID NO 210
<211> LENGTH: 42
<212> TYPE: DNA
<213> ORGANISM: artificial sequence
<220> FEATURE:
<223> OTHER INFORMATION: artificial sequence

<400> SEQUENCE: 210
aattgtttcc ctcccagtcc cttggctatc atgcaagctt gg              42

<210> SEQ ID NO 211
<211> LENGTH: 42
<212> TYPE: DNA
<213> ORGANISM: artificial sequence
<220> FEATURE:
<223> OTHER INFORMATION: artificial sequence

<400> SEQUENCE: 211
ttaacaaagg gagggtcagg gaaccgatag tacgttcgaa cc              42

<210> SEQ ID NO 212
<211> LENGTH: 25
<212> TYPE: DNA
<213> ORGANISM: artificial sequence
<220> FEATURE:
<223> OTHER INFORMATION: artificial sequence

<400> SEQUENCE: 212
ggcaccctcc cagtcccttg gctat                                 25

<210> SEQ ID NO 213
<211> LENGTH: 28
<212> TYPE: DNA
<213> ORGANISM: artificial sequence
<220> FEATURE:
<223> OTHER INFORMATION: artificial sequence

<400> SEQUENCE: 213
gtttccctcc cagtcccttg gctatcat                              28

<210> SEQ ID NO 214
<211> LENGTH: 13
<212> TYPE: DNA
<213> ORGANISM: artificial sequence
<220> FEATURE:
<223> OTHER INFORMATION: artificial sequence

<400> SEQUENCE: 214
agcttgcatg ata                                              13

<210> SEQ ID NO 215
<211> LENGTH: 55
<212> TYPE: DNA
<213> ORGANISM: Homo sapiens

<400> SEQUENCE: 215

-continued taaagtgact cttttacagg aggcaataac agatggctta gaaattgtgg tttca    55

<210> SEQ ID NO 216
<211> LENGTH: 49
<212> TYPE: DNA
<213> ORGANISM: Homo sapiens

<400> SEQUENCE: 216
taaagtgact cttttacaaa taacagatgg cttagaaatt gtggtttca    49

<210> SEQ ID NO 217
<211> LENGTH: 55
<212> TYPE: DNA
<213> ORGANISM: Homo sapiens

<400> SEQUENCE: 217
tgcccaattt gtttggatat gttgaagaac accatgacta caaaggagtg tttac    55

<210> SEQ ID NO 218
<211> LENGTH: 50
<212> TYPE: DNA
<213> ORGANISM: Homo sapiens

<400> SEQUENCE: 218
tgcccaattt gtttggatat gtaacaccat gactacaaag gagtgtttac    50

<210> SEQ ID NO 219
<211> LENGTH: 54
<212> TYPE: DNA
<213> ORGANISM: Mus musculus

<400> SEQUENCE: 219
ggctttccct cccagtccct tggctatgga atatgttaat gactttgatt tgat    54

<210> SEQ ID NO 220
<211> LENGTH: 55
<212> TYPE: DNA
<213> ORGANISM: Mus musculus

<400> SEQUENCE: 220
ggctttccct cccagtccct tgcgctatgg aatatgttaa tgactttgat ttgat    55

<210> SEQ ID NO 221
<211> LENGTH: 52
<212> TYPE: DNA
<213> ORGANISM: Mus musculus

<400> SEQUENCE: 221
ggctttccct cccagtccct tggctggaat atgttaatga ctttgatttg at    52

<210> SEQ ID NO 222
<211> LENGTH: 48
<212> TYPE: DNA
<213> ORGANISM: Mus musculus

<400> SEQUENCE: 222
ggctttccct cccagtccct tggaatatgt taatgacttt gatttgat    48

<210> SEQ ID NO 223
<211> LENGTH: 42
<212> TYPE: DNA
<213> ORGANISM: Mus musculus

<400> SEQUENCE: 223

-continued ggctttccct cccagtccct tgttaatga ctttgatttg at          42

<210> SEQ ID NO 224
<211> LENGTH: 41
<212> TYPE: DNA
<213> ORGANISM: Mus musculus

<400> SEQUENCE: 224
ggctttccct cccagtccct tgttaatgac tttgatttga t          41

<210> SEQ ID NO 225
<211> LENGTH: 25
<212> TYPE: DNA
<213> ORGANISM: Mus musculus

<400> SEQUENCE: 225
ggctttccct cccagtccct ttgat                            25

<210> SEQ ID NO 226
<211> LENGTH: 55
<212> TYPE: DNA
<213> ORGANISM: Mus musculus

<400> SEQUENCE: 226
ttggacacca gcgtctgggc tcgtgagtta gggtggaagc ctgggagaaa gccag    55

<210> SEQ ID NO 227
<211> LENGTH: 50
<212> TYPE: DNA
<213> ORGANISM: Mus musculus

<400> SEQUENCE: 227
ttggacacca gcgtctgggc tcttagggtg gaagcctggg agaaagccag    50

<210> SEQ ID NO 228
<211> LENGTH: 55
<212> TYPE: DNA
<213> ORGANISM: Homo sapiens

<400> SEQUENCE: 228
gctgtgctac agaccaccag ttacatcctg gggtagaaac tggtggcagg ctggc    55

<210> SEQ ID NO 229
<211> LENGTH: 52
<212> TYPE: DNA
<213> ORGANISM: Homo sapiens

<400> SEQUENCE: 229
gctgtgctac agaccagtta catcctgggg tagaaactgg tggcaggctg gc    52

<210> SEQ ID NO 230
<211> LENGTH: 55
<212> TYPE: DNA
<213> ORGANISM: Homo sapiens

<400> SEQUENCE: 230
ttcagacctt tcaaccacta gcactagcct tgcaacatct cccactaaac cctat    55

<210> SEQ ID NO 231
<211> LENGTH: 51
<212> TYPE: DNA
<213> ORGANISM: Homo sapiens

<400> SEQUENCE: 231
ttcagacctt tcaaccacta gcactagcca acatctccca ctaaaccta t          51

<210> SEQ ID NO 232
<211> LENGTH: 26
<212> TYPE: DNA
<213> ORGANISM: Homo sapiens

<400> SEQUENCE: 232
ttgaagccta gcctgtcacc tggaaa                                     26

<210> SEQ ID NO 233
<211> LENGTH: 55
<212> TYPE: DNA
<213> ORGANISM: Homo sapiens

<400> SEQUENCE: 233
tggccgactt cggcctgaag ccctgatgc gctgctctag cctgtcacct ggaaa       55

<210> SEQ ID NO 234
<211> LENGTH: 49
<212> TYPE: DNA
<213> ORGANISM: Homo sapiens

<400> SEQUENCE: 234
acctttcaac cactagcact agccttgcaa catctcccac taaacctat             49

<210> SEQ ID NO 235
<211> LENGTH: 54
<212> TYPE: DNA
<213> ORGANISM: Homo sapiens

<400> SEQUENCE: 235
acctttcaac cactagcact agactagcct tgcaacatct cccactaaac ctat       54

<210> SEQ ID NO 236
<211> LENGTH: 46
<212> TYPE: DNA
<213> ORGANISM: Homo sapiens

<400> SEQUENCE: 236
acctttcaac cactagcact attgcaacat ctcccactaa acctat                46

<210> SEQ ID NO 237
<211> LENGTH: 55
<212> TYPE: DNA
<213> ORGANISM: Homo sapiens

<400> SEQUENCE: 237
tgcccaattt gtttggatat gttgaagaac accatgacta caaaggagtg tttac      55

<210> SEQ ID NO 238
<211> LENGTH: 47
<212> TYPE: DNA
<213> ORGANISM: Homo sapiens

<400> SEQUENCE: 238
tgcccaattt gtttggatat gttgaatgac tacaaaggag tgtttac                47

<210> SEQ ID NO 239
<211> LENGTH: 46
<212> TYPE: DNA
<213> ORGANISM: Homo sapiens

<400> SEQUENCE: 239
tgcccaattt gtttggatat gttgaagact acaaggagt gtttac           46

<210> SEQ ID NO 240
<211> LENGTH: 25
<212> TYPE: DNA
<213> ORGANISM: Homo sapiens

<400> SEQUENCE: 240
tgcccaattt gtaaggagtg tttac                                 25

<210> SEQ ID NO 241
<211> LENGTH: 53
<212> TYPE: DNA
<213> ORGANISM: Homo sapiens

<400> SEQUENCE: 241
tgcccaattt gtttggatat gttgaagaac accatgacta caaaggagtg ttt  53

<210> SEQ ID NO 242
<211> LENGTH: 55
<212> TYPE: DNA
<213> ORGANISM: Homo sapiens

<400> SEQUENCE: 242
tgcccaattt gtttggatat gttgaagaac aacccatgac tacaaaggag tgttt  55

<210> SEQ ID NO 243
<211> LENGTH: 50
<212> TYPE: DNA
<213> ORGANISM: Homo sapiens

<400> SEQUENCE: 243
tgcccaattt gtttggatat gttgaagaac atgactacaa aggagtgttt      50

<210> SEQ ID NO 244
<211> LENGTH: 50
<212> TYPE: DNA
<213> ORGANISM: Homo sapiens

<400> SEQUENCE: 244
tgcccaattt gtttggatat gttgaagaac atgactacaa aggagtgttt      50

<210> SEQ ID NO 245
<211> LENGTH: 48
<212> TYPE: DNA
<213> ORGANISM: Homo sapiens

<400> SEQUENCE: 245
tgcccaattt gtttggatat gttgaagaac acctacaaag gagtgttt        48

<210> SEQ ID NO 246
<211> LENGTH: 47
<212> TYPE: DNA
<213> ORGANISM: Homo sapiens

<400> SEQUENCE: 246
tgcccaattt gtttggatat gttgaagaac tctacaaagg agtgttt         47

<210> SEQ ID NO 247
<211> LENGTH: 23
<212> TYPE: DNA

<213> ORGANISM: Homo sapiens

<400> SEQUENCE: 247
tgcccaattt gtttggagtg ttt                                              23

<210> SEQ ID NO 248
<211> LENGTH: 156
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (137)..(156)
<223> OTHER INFORMATION: n is a, c, g, or t

<400> SEQUENCE: 248
gtctaaagga cagaattttc aacgggtgtg ccaatggcca ctttccaggt ggcaaagccc       60
gttgaacttc tcaaaaagaa cgctcgctca gtgttctgac gtcggatcac tgagcgagcg     120
atcgtagaag tggcacnnnn nnnnnnnnnn nnnnnn                               156

<210> SEQ ID NO 249
<211> LENGTH: 158
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (139)..(158)
<223> OTHER INFORMATION: n is a, c, g, or t

<400> SEQUENCE: 249
gtcgtctata ggacggcgag gacaacggga agtgccaatg tgctctttcc aagagcaaac      60
accccgttgg cttcaagatg accgctcgct cagcgatctg acaacggatc gctgagcgag     120
cggtctgaga agtggcacnn nnnnnnnnnn nnnnnnn                              158

<210> SEQ ID NO 250
<211> LENGTH: 165
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (146)..(165)
<223> OTHER INFORMATION: n is a, c, g, or t

<400> SEQUENCE: 250
ggaattgccg atctatagga cggcagattc aacgggatgt gccaatgcac tctttccagg      60
agtgaacacc ccgttggctt caacatgatc gcccgctcaa cggtccgatg tcggatcgtt     120
gagcgggcga tctgagaagt ggcacnnnnn nnnnnnnnnn nnnnn                     165

<210> SEQ ID NO 251
<211> LENGTH: 154
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (135)..(154)
<223> OTHER INFORMATION: n is a, c, g, or t

<400> SEQUENCE: 251

```
ggccataagt cgacttacat atccgtgcgt gtgcattatg ggccactcca caggtctatt    60
cccacggata atcacgactt tccactaagc tttcgaaagt tcgaaagctt agtggaaagc   120
ttcgtggtta gcacnnnnnn nnnnnnnnnn nnnn                               154
```

<210> SEQ ID NO 252
<211> LENGTH: 25
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (6)..(25)
<223> OTHER INFORMATION: n is a, c, g, or t

<400> SEQUENCE: 252

```
ggcacnnnnn nnnnnnnnnn nnnnn                                          25
```

<210> SEQ ID NO 253
<211> LENGTH: 24
<212> TYPE: DNA
<213> ORGANISM: artificial sequence
<220> FEATURE:
<223> OTHER INFORMATION: artificial sequence

<400> SEQUENCE: 253

```
tagtcatggt gttcttcaac atat                                           24
```

<210> SEQ ID NO 254
<211> LENGTH: 22
<212> TYPE: DNA
<213> ORGANISM: artificial sequence
<220> FEATURE:
<223> OTHER INFORMATION: artificial sequence

<400> SEQUENCE: 254

```
tagtcatggt gttcttcaac at                                             22
```

<210> SEQ ID NO 255
<211> LENGTH: 20
<212> TYPE: DNA
<213> ORGANISM: Alicyclobacillus acidiphilus

<400> SEQUENCE: 255

```
tagtcatggt gttcttcaac                                                20
```

<210> SEQ ID NO 256
<211> LENGTH: 18
<212> TYPE: DNA
<213> ORGANISM: artificial sequence
<220> FEATURE:
<223> OTHER INFORMATION: artificial sequence

<400> SEQUENCE: 256

```
tagtcatggt gttcttca                                                  18
```

<210> SEQ ID NO 257
<211> LENGTH: 16
<212> TYPE: DNA
<213> ORGANISM: artificial sequence
<220> FEATURE:
<223> OTHER INFORMATION: artificial sequence

<400> SEQUENCE: 257

```
tagtcatggt gttctt                                                    16

<210> SEQ ID NO 258
<211> LENGTH: 15
<212> TYPE: DNA
<213> ORGANISM: artificial sequence
<220> FEATURE:
<223> OTHER INFORMATION: artificial sequence

<400> SEQUENCE: 258
tagtcatggt gttct                                                     15

<210> SEQ ID NO 259
<211> LENGTH: 14
<212> TYPE: DNA
<213> ORGANISM: artificial sequence
<220> FEATURE:
<223> OTHER INFORMATION: artificial sequence

<400> SEQUENCE: 259
tagtcatggt gttc                                                      14

<210> SEQ ID NO 260
<211> LENGTH: 13
<212> TYPE: DNA
<213> ORGANISM: artificial sequence
<220> FEATURE:
<223> OTHER INFORMATION: artificial sequence

<400> SEQUENCE: 260
tagtcatggt gtt                                                       13

<210> SEQ ID NO 261
<211> LENGTH: 12
<212> TYPE: DNA
<213> ORGANISM: artificial sequence
<220> FEATURE:
<223> OTHER INFORMATION: artificial sequence

<400> SEQUENCE: 261
tagtcatggt gt                                                        12

<210> SEQ ID NO 262
<211> LENGTH: 25
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (6)..(25)
<223> OTHER INFORMATION: n is a, c, g, or t

<400> SEQUENCE: 262
ggcacnnnnn nnnnnnnnnn nnnnn                                          25

<210> SEQ ID NO 263
<211> LENGTH: 20
<212> TYPE: DNA
<213> ORGANISM: Alicyclobacillus acidiphilus

<400> SEQUENCE: 263
tagtcatggt gttcttcaac                                                20

<210> SEQ ID NO 264
<211> LENGTH: 20
```

```
<212> TYPE: DNA
<213> ORGANISM: artificial sequence
<220> FEATURE:
<223> OTHER INFORMATION: artificial sequence

<400> SEQUENCE: 264
gagtcatggt gttcttcaac                                              20

<210> SEQ ID NO 265
<211> LENGTH: 20
<212> TYPE: DNA
<213> ORGANISM: artificial sequence
<220> FEATURE:
<223> OTHER INFORMATION: artificial sequence

<400> SEQUENCE: 265
tattcatggt gttcttcaac                                              20

<210> SEQ ID NO 266
<211> LENGTH: 20
<212> TYPE: DNA
<213> ORGANISM: artificial sequence
<220> FEATURE:
<223> OTHER INFORMATION: artificial sequence

<400> SEQUENCE: 266
tagtaatggt gttcttcaac                                              20

<210> SEQ ID NO 267
<211> LENGTH: 20
<212> TYPE: DNA
<213> ORGANISM: artificial sequence
<220> FEATURE:
<223> OTHER INFORMATION: artificial sequence

<400> SEQUENCE: 267
tagtcagggt gttcttcaac                                              20

<210> SEQ ID NO 268
<211> LENGTH: 20
<212> TYPE: DNA
<213> ORGANISM: artificial sequence
<220> FEATURE:
<223> OTHER INFORMATION: artificial sequence

<400> SEQUENCE: 268
tagtcatgtt gttcttcaac                                              20

<210> SEQ ID NO 269
<211> LENGTH: 20
<212> TYPE: DNA
<213> ORGANISM: artificial sequence
<220> FEATURE:
<223> OTHER INFORMATION: artificial sequence

<400> SEQUENCE: 269
tagtcatggt tttcttcaac                                              20

<210> SEQ ID NO 270
<211> LENGTH: 20
<212> TYPE: DNA
<213> ORGANISM: artificial sequence
<220> FEATURE:
<223> OTHER INFORMATION: artificial sequence

<400> SEQUENCE: 270
```

```
tagtcatggt gtgcttcaac                                              20
```

<210> SEQ ID NO 271
<211> LENGTH: 20
<212> TYPE: DNA
<213> ORGANISM: artificial sequence
<220> FEATURE:
<223> OTHER INFORMATION: artificial sequence

<400> SEQUENCE: 271

```
tagtcatggt gttcgtcaac                                              20
```

<210> SEQ ID NO 272
<211> LENGTH: 25
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (6)..(25)
<223> OTHER INFORMATION: n is a, c, g, or t

<400> SEQUENCE: 272

```
ggcacnnnnn nnnnnnnnnn nnnnn                                        25
```

<210> SEQ ID NO 273
<211> LENGTH: 20
<212> TYPE: DNA
<213> ORGANISM: Alicyclobacillus acidiphilus

<400> SEQUENCE: 273

```
tagtcatggt gttcttcaac                                              20
```

<210> SEQ ID NO 274
<211> LENGTH: 20
<212> TYPE: DNA
<213> ORGANISM: artificial sequence
<220> FEATURE:
<223> OTHER INFORMATION: artificial sequence

<400> SEQUENCE: 274

```
gcgtcatggt gttcttcaac                                              20
```

<210> SEQ ID NO 275
<211> LENGTH: 20
<212> TYPE: DNA
<213> ORGANISM: artificial sequence
<220> FEATURE:
<223> OTHER INFORMATION: artificial sequence

<400> SEQUENCE: 275

```
tatgcatggt gttcttcaac                                              20
```

<210> SEQ ID NO 276
<211> LENGTH: 20
<212> TYPE: DNA
<213> ORGANISM: artificial sequence
<220> FEATURE:
<223> OTHER INFORMATION: artificial sequence

<400> SEQUENCE: 276

```
tagtactggt gttcttcaac                                              20
```

<210> SEQ ID NO 277
<211> LENGTH: 20

-continued

```
<212> TYPE: DNA
<213> ORGANISM: artificial sequence
<220> FEATURE:
<223> OTHER INFORMATION: artificial sequence

<400> SEQUENCE: 277
tagtcagtgt gttcttcaac                                            20

<210> SEQ ID NO 278
<211> LENGTH: 20
<212> TYPE: DNA
<213> ORGANISM: artificial sequence
<220> FEATURE:
<223> OTHER INFORMATION: artificial sequence

<400> SEQUENCE: 278
tagtcatgtg gttcttcaac                                            20

<210> SEQ ID NO 279
<211> LENGTH: 20
<212> TYPE: DNA
<213> ORGANISM: artificial sequence
<220> FEATURE:
<223> OTHER INFORMATION: artificial sequence

<400> SEQUENCE: 279
tagtcatggt tgtcttcaac                                            20

<210> SEQ ID NO 280
<211> LENGTH: 20
<212> TYPE: DNA
<213> ORGANISM: artificial sequence
<220> FEATURE:
<223> OTHER INFORMATION: artificial sequence

<400> SEQUENCE: 280
tagtcatggt gtgattcaac                                            20

<210> SEQ ID NO 281
<211> LENGTH: 20
<212> TYPE: DNA
<213> ORGANISM: artificial sequence
<220> FEATURE:
<223> OTHER INFORMATION: artificial sequence

<400> SEQUENCE: 281
tagtcatggt gttcggcaac                                            20

<210> SEQ ID NO 282
<211> LENGTH: 55
<212> TYPE: DNA
<213> ORGANISM: Homo sapiens

<400> SEQUENCE: 282
gactcctttg tagtcatggt gttcttcaac atatccaaac aaattgggca catta     55

<210> SEQ ID NO 283
<211> LENGTH: 50
<212> TYPE: DNA
<213> ORGANISM: Homo sapiens

<400> SEQUENCE: 283
gactcctttg tagtcatggt gttcttcatc caaacaaatt gggcacatta           50

<210> SEQ ID NO 284
```

```
<211> LENGTH: 46
<212> TYPE: DNA
<213> ORGANISM: Homo sapiens

<400> SEQUENCE: 284
gactcctttg tagtcatggt gttctccaaa caaattgggc acatta            46

<210> SEQ ID NO 285
<211> LENGTH: 43
<212> TYPE: DNA
<213> ORGANISM: Homo sapiens

<400> SEQUENCE: 285
gactcctttg tagtcatggt gtccaaacaa attgggcaca tta               43

<210> SEQ ID NO 286
<211> LENGTH: 46
<212> TYPE: DNA
<213> ORGANISM: Homo sapiens

<400> SEQUENCE: 286
tcattttttt tgaacacaat gactataatg ctatatatat atgaaa            46

<210> SEQ ID NO 287
<211> LENGTH: 44
<212> TYPE: DNA
<213> ORGANISM: Homo sapiens

<400> SEQUENCE: 287
tcattttttt tgaacacaat gactataatg ctatatatat gaaa              44

<210> SEQ ID NO 288
<211> LENGTH: 42
<212> TYPE: DNA
<213> ORGANISM: Homo sapiens

<400> SEQUENCE: 288
tcattttttt tgaacacaat gactataatg ctatatatga aa                42

<210> SEQ ID NO 289
<211> LENGTH: 44
<212> TYPE: DNA
<213> ORGANISM: Homo sapiens

<400> SEQUENCE: 289
tatcccttct agacatggtg ttccatttgt attttttttt cttt              44

<210> SEQ ID NO 290
<211> LENGTH: 45
<212> TYPE: DNA
<213> ORGANISM: Homo sapiens

<400> SEQUENCE: 290
tatcccttct agacatggtg ttccatttgt attttttttt tcttt             45

<210> SEQ ID NO 291
<211> LENGTH: 43
<212> TYPE: DNA
<213> ORGANISM: Homo sapiens

<400> SEQUENCE: 291
tatcccttct agacatggtg ttccatttgt atttttttc ttt                43
```

<210> SEQ ID NO 292
<211> LENGTH: 1129
<212> TYPE: PRT
<213> ORGANISM: Alicyclobacillus acidoterrestris

<400> SEQUENCE: 292

```
Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
        290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
        355                 360                 365

Arg Lys Leu Asn His Ala Lys Met Phe Ala Thr Phe Thr Leu Pro Asp
    370                 375                 380
```

```
Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
            405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
            435                 440                 445

Asn Leu Leu Pro Arg Asp Pro Asn Glu Pro Ile Ala Leu Tyr Phe Arg
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
            515                 520                 525

Val Gly Asp Asn His Arg Ala Phe Val His Phe Asp Lys Leu Ser Asp
530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
    595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
            755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
```

```
            805                 810                 815
Ile Met Glu Ala Leu Gly Tyr Val Tyr Ala Leu Asp Glu Arg Gly Lys
                820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
        850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg  Cys Asp Trp Gly Glu  Val Asp Gly
        995                 1000                1005

Glu Leu  Val Leu Ile Pro Arg  Leu Thr Gly Lys Arg  Thr Ala Asp
    1010                1015                1020

Ser Tyr  Ser Asn Lys Val Phe  Tyr Thr Asn Thr Gly  Val Thr Tyr
    1025                1030                1035

Tyr Glu  Arg Glu Arg Gly Lys  Lys Arg Arg Lys Val  Phe Ala Gln
    1040                1045                1050

Glu Lys  Leu Ser Glu Glu Glu  Ala Glu Leu Leu Val  Glu Ala Asp
    1055                1060                1065

Glu Ala  Arg Glu Lys Ser Val  Val Leu Met Arg Asp  Pro Ser Gly
    1070                1075                1080

Ile Ile  Asn Arg Gly Asn Trp  Thr Arg Gln Lys Glu  Phe Trp Ser
    1085                1090                1095

Met Val  Asn Gln Arg Ile Glu  Gly Tyr Leu Val Lys  Gln Ile Arg
    1100                1105                1110

Ser Arg  Val Pro Leu Gln Asp  Ser Ala Cys Glu Asn  Thr Gly Asp
    1115                1120                1125

Ile

<210> SEQ ID NO 293
<211> LENGTH: 1147
<212> TYPE: PRT
<213> ORGANISM: Alicyclobacillus kakegawensis

<400> SEQUENCE: 293

Met Ala Val Lys Ser Ile Lys Val Lys Leu Arg Leu Ser Glu Cys Pro
1               5                   10                  15

Asp Ile Leu Ala Gly Met Trp Gln Leu His Arg Ala Thr Asn Ala Gly
            20                  25                  30

Val Arg Tyr Tyr Thr Glu Trp Val Ser Leu Met Arg Gln Glu Ile Leu
```

```
               35                  40                  45
Tyr Ser Arg Gly Pro Asp Gly Gln Gln Cys Tyr Met Thr Ala Glu
 50                  55                  60

Asp Cys Gln Arg Glu Leu Leu Arg Arg Leu Arg Asn Arg Gln Leu His
 65                  70                  75                  80

Asn Gly Arg Gln Asp Gln Pro Gly Thr Asp Ala Asp Leu Leu Ala Ile
                 85                  90                  95

Ser Arg Arg Leu Tyr Glu Ile Leu Val Leu Gln Ser Ile Gly Lys Arg
                100                 105                 110

Gly Asp Ala Gln Gln Ile Ala Ser Ser Phe Leu Ser Pro Leu Val Asp
                115                 120                 125

Pro Asn Ser Lys Gly Gly Arg Gly Glu Ala Lys Ser Gly Arg Lys Pro
130                 135                 140

Ala Trp Gln Lys Met Arg Asp Gln Gly Asp Pro Arg Trp Val Ala Ala
145                 150                 155                 160

Arg Glu Lys Tyr Glu Gln Arg Lys Ala Val Asp Pro Ser Lys Glu Ile
                165                 170                 175

Leu Asn Ser Leu Asp Ala Leu Gly Leu Arg Pro Leu Phe Ala Val Phe
                180                 185                 190

Thr Glu Thr Tyr Arg Ser Gly Val Asp Trp Lys Pro Leu Gly Lys Ser
                195                 200                 205

Gln Gly Val Arg Thr Trp Asp Arg Asp Met Phe Gln Gln Ala Leu Glu
210                 215                 220

Arg Leu Met Ser Trp Glu Ser Trp Asn Arg Arg Val Gly Glu Glu Tyr
225                 230                 235                 240

Ala Arg Leu Phe Gln Gln Lys Met Lys Phe Glu Gln Glu His Phe Ala
                245                 250                 255

Glu Gln Ser His Leu Val Lys Leu Ala Arg Ala Leu Glu Ala Asp Met
                260                 265                 270

Arg Ala Ala Ser Gln Gly Phe Glu Ala Lys Arg Gly Thr Ala His Gln
                275                 280                 285

Ile Thr Arg Arg Ala Leu Arg Gly Ala Asp Arg Val Phe Glu Ile Trp
290                 295                 300

Lys Ser Ile Pro Glu Glu Ala Leu Phe Ser Gln Tyr Asp Glu Val Ile
305                 310                 315                 320

Arg Gln Val Gln Ala Glu Lys Arg Arg Asp Phe Gly Ser His Asp Leu
                325                 330                 335

Phe Ala Lys Leu Ala Glu Pro Lys Tyr Gln Pro Leu Trp Arg Ala Asp
                340                 345                 350

Glu Thr Phe Leu Thr Arg Tyr Ala Leu Tyr Asn Gly Val Leu Arg Asp
                355                 360                 365

Leu Glu Lys Ala Arg Gln Phe Ala Thr Phe Thr Leu Pro Asp Ala Cys
                370                 375                 380

Val Asn Pro Ile Trp Thr Arg Phe Glu Ser Ser Gln Gly Ser Asn Leu
385                 390                 395                 400

His Lys Tyr Glu Phe Leu Phe Asp His Leu Gly Pro Gly Arg His Ala
                405                 410                 415

Val Arg Phe Gln Arg Leu Leu Val Val Glu Ser Glu Gly Ala Lys Glu
                420                 425                 430

Arg Asp Ser Val Val Val Pro Val Ala Pro Ser Gly Gln Leu Asp Lys
                435                 440                 445

Leu Val Leu Arg Glu Glu Glu Lys Ser Ser Val Ala Leu His Leu His
                450                 455                 460
```

-continued

```
Asp Thr Ala Arg Pro Asp Gly Phe Met Ala Glu Trp Ala Gly Ala Lys
465                 470                 475                 480

Leu Gln Tyr Glu Arg Ser Thr Leu Ala Arg Lys Ala Arg Arg Asp Lys
                485                 490                 495

Gln Gly Met Arg Ser Trp Arg Arg Gln Pro Ser Met Leu Met Ser Ala
            500                 505                 510

Ala Gln Met Leu Glu Asp Ala Lys Gln Ala Gly Asp Val Tyr Leu Asn
        515                 520                 525

Ile Ser Val Arg Val Lys Ser Pro Ser Glu Val Arg Gly Gln Arg Arg
530                 535                 540

Pro Pro Tyr Ala Ala Leu Phe Arg Ile Asp Asp Lys Gln Arg Arg Val
545                 550                 555                 560

Thr Val Asn Tyr Asn Lys Leu Ser Ala Tyr Leu Glu Glu His Pro Asp
                565                 570                 575

Lys Gln Ile Pro Gly Ala Pro Gly Leu Leu Ser Gly Leu Arg Val Met
            580                 585                 590

Ser Val Asp Leu Gly Leu Arg Thr Ser Ala Ser Ile Ser Val Phe Arg
        595                 600                 605

Val Ala Lys Lys Glu Glu Val Glu Ala Leu Gly Asp Gly Arg Pro Pro
610                 615                 620

His Tyr Tyr Pro Ile His Gly Thr Asp Asp Leu Val Ala Val His Glu
625                 630                 635                 640

Arg Ser His Leu Ile Gln Met Pro Gly Glu Thr Glu Thr Lys Gln Leu
                645                 650                 655

Arg Lys Leu Arg Glu Glu Arg Gln Ala Val Leu Arg Pro Leu Phe Ala
            660                 665                 670

Gln Leu Ala Leu Leu Arg Leu Leu Val Arg Cys Gly Ala Ala Asp Glu
        675                 680                 685

Arg Ile Arg Thr Arg Ser Trp Gln Arg Leu Thr Lys Gln Gly Arg Glu
690                 695                 700

Phe Thr Lys Arg Leu Thr Pro Ser Trp Arg Glu Ala Leu Glu Leu Glu
705                 710                 715                 720

Leu Thr Arg Leu Glu Ala Tyr Cys Gly Arg Val Pro Asp Asp Glu Trp
                725                 730                 735

Ser Arg Ile Val Asp Arg Thr Val Ile Ala Leu Trp Arg Arg Met Gly
            740                 745                 750

Lys Gln Val Arg Asp Trp Arg Lys Gln Val Lys Ser Gly Ala Lys Val
        755                 760                 765

Lys Val Lys Gly Tyr Gln Leu Asp Val Val Gly Gly Asn Ser Leu Ala
770                 775                 780

Gln Ile Asp Tyr Leu Glu Gln Gln Tyr Lys Phe Leu Arg Arg Trp Ser
785                 790                 795                 800

Phe Phe Ala Arg Ala Ser Gly Leu Val Val Arg Ala Asp Arg Glu Ser
                805                 810                 815

His Phe Ala Val Ala Leu Arg Gln His Ile Glu Asn Ala Lys Arg Asp
            820                 825                 830

Arg Leu Lys Lys Leu Ala Asp Arg Ile Leu Met Glu Ala Leu Gly Tyr
        835                 840                 845

Val Tyr Glu Ala Ser Gly Pro Arg Glu Gly Gln Trp Thr Ala Gln His
850                 855                 860

Pro Pro Cys Gln Leu Ile Ile Leu Glu Glu Leu Ser Ala Tyr Arg Phe
865                 870                 875                 880
```

-continued

```
Ser Asp Asp Arg Pro Pro Ser Glu Asn Ser Lys Leu Met Ala Trp Gly
            885                 890                 895

His Arg Gly Ile Leu Glu Glu Leu Val Asn Gln Ala Gln Val His Asp
        900                 905                 910

Val Leu Val Gly Thr Val Tyr Ala Ala Phe Ser Ser Arg Phe Asp Ala
    915                 920                 925

Arg Thr Gly Ala Pro Gly Val Arg Cys Arg Arg Val Pro Ala Arg Phe
930                 935                 940

Val Gly Ala Thr Val Asp Asp Ser Leu Pro Leu Trp Leu Thr Glu Phe
945                 950                 955                 960

Leu Asp Lys His Arg Leu Asp Lys Asn Leu Leu Arg Pro Asp Asp Val
                965                 970                 975

Ile Pro Thr Gly Glu Gly Glu Phe Leu Val Ser Pro Cys Gly Glu Glu
            980                 985                 990

Ala Ala Arg Val Arg Gln Val His Ala Asp Ile Asn Ala Ala Gln Asn
        995                 1000                1005

Leu Gln Arg Arg Leu Trp Gln Asn Phe Asp Ile Thr Glu Leu Arg
    1010                1015                1020

Leu Arg Cys Asp Val Lys Met Gly Gly Glu Gly Thr Val Leu Val
    1025                1030                1035

Pro Arg Val Asn Asn Ala Arg Ala Lys Gln Leu Phe Gly Lys Lys
    1040                1045                1050

Val Leu Val Ser Gln Asp Gly Val Thr Phe Phe Glu Arg Ser Gln
    1055                1060                1065

Thr Gly Gly Lys Pro His Ser Glu Lys Gln Thr Asp Leu Thr Asp
    1070                1075                1080

Lys Glu Leu Glu Leu Ile Ala Glu Ala Asp Glu Ala Arg Ala Lys
    1085                1090                1095

Ser Val Val Leu Phe Arg Asp Pro Ser Gly His Ile Gly Lys Gly
    1100                1105                1110

His Trp Ile Arg Gln Arg Glu Phe Trp Ser Leu Val Lys Gln Arg
    1115                1120                1125

Ile Glu Ser His Thr Ala Glu Arg Ile Arg Val Arg Gly Val Gly
    1130                1135                1140

Ser Ser Leu Asp
    1145

<210> SEQ ID NO 294
<211> LENGTH: 1146
<212> TYPE: PRT
<213> ORGANISM: Alicyclobacillus macrosporangiidus

<400> SEQUENCE: 294

Met Asn Val Ala Val Lys Ser Ile Lys Val Lys Leu Met Leu Gly His
1               5                   10                  15

Leu Pro Glu Ile Arg Glu Gly Leu Trp His Leu His Glu Ala Val Asn
            20                  25                  30

Leu Gly Val Arg Tyr Tyr Thr Glu Trp Leu Ala Leu Leu Arg Gln Gly
        35                  40                  45

Asn Leu Tyr Arg Arg Gly Lys Asp Gly Ala Gln Glu Cys Tyr Met Thr
    50                  55                  60

Ala Glu Gln Cys Arg Gln Glu Leu Leu Val Arg Leu Arg Asp Arg Gln
65                  70                  75                  80

Lys Arg Asn Gly His Thr Gly Asp Pro Gly Thr Asp Glu Glu Leu Leu
                85                  90                  95
```

```
Gly Val Ala Arg Arg Leu Tyr Glu Leu Leu Pro Gln Ser Val Gly
                100                 105                 110

Lys Lys Gly Gln Ala Gln Met Leu Ala Ser Gly Phe Leu Ser Pro Leu
    115                 120                 125

Ala Asp Pro Lys Ser Glu Gly Lys Gly Thr Ser Lys Ser Gly Arg
    130                 135                 140

Lys Pro Ala Trp Met Gly Met Lys Glu Ala Gly Asp Ser Arg Trp Val
145                 150                 155                 160

Glu Ala Lys Ala Arg Tyr Glu Ala Asn Lys Ala Lys Asp Pro Thr Lys
                165                 170                 175

Gln Val Ile Ala Ser Leu Glu Met Tyr Gly Leu Arg Pro Leu Phe Asp
                180                 185                 190

Val Phe Thr Glu Thr Tyr Lys Thr Ile Arg Trp Met Pro Leu Gly Lys
                195                 200                 205

His Gln Gly Val Arg Ala Trp Asp Arg Asp Met Phe Gln Gln Ser Leu
                210                 215                 220

Glu Arg Leu Met Ser Trp Glu Ser Trp Asn Glu Arg Val Gly Ala Glu
225                 230                 235                 240

Phe Ala Arg Leu Val Asp Arg Arg Asp Arg Phe Arg Glu Lys His Phe
                245                 250                 255

Thr Gly Gln Glu His Leu Val Ala Leu Ala Gln Arg Leu Glu Gln Glu
                260                 265                 270

Met Lys Glu Ala Ser Pro Gly Phe Glu Ser Lys Ser Ser Gln Ala His
                275                 280                 285

Arg Ile Thr Lys Arg Ala Leu Arg Gly Ala Asp Gly Ile Ile Asp Asp
                290                 295                 300

Trp Leu Lys Leu Ser Glu Gly Glu Pro Val Asp Arg Phe Asp Glu Ile
305                 310                 315                 320

Leu Arg Lys Arg Gln Ala Gln Asn Pro Arg Arg Phe Gly Ser His Asp
                325                 330                 335

Leu Phe Leu Lys Leu Ala Glu Pro Val Phe Gln Pro Leu Trp Arg Glu
                340                 345                 350

Asp Pro Ser Phe Leu Ser Arg Trp Ala Ser Tyr Asn Glu Val Leu Asn
                355                 360                 365

Lys Leu Glu Asp Ala Lys Gln Phe Ala Thr Phe Thr Leu Pro Ser Pro
                370                 375                 380

Cys Ser Asn Pro Val Trp Ala Arg Phe Glu Asn Ala Glu Gly Thr Asn
385                 390                 395                 400

Ile Phe Lys Tyr Asp Phe Leu Phe Asp His Phe Gly Lys Gly Arg His
                405                 410                 415

Gly Val Arg Phe Gln Arg Met Ile Val Met Arg Asp Gly Val Pro Thr
                420                 425                 430

Glu Val Glu Gly Ile Val Val Pro Ile Ala Pro Ser Arg Gln Leu Asp
                435                 440                 445

Ala Leu Ala Pro Asn Asp Ala Ala Ser Pro Ile Asp Val Phe Val Gly
                450                 455                 460

Asp Pro Ala Ala Pro Gly Ala Phe Arg Gly Gln Phe Gly Gly Ala Lys
465                 470                 475                 480

Ile Gln Tyr Arg Arg Ser Ala Leu Val Arg Lys Gly Arg Arg Glu Glu
                485                 490                 495

Lys Ala Tyr Leu Cys Gly Phe Arg Leu Pro Ser Gln Arg Arg Thr Gly
                500                 505                 510
```

```
Thr Pro Ala Asp Asp Ala Gly Glu Val Phe Leu Asn Leu Ser Leu Arg
            515                 520                 525

Val Glu Ser Gln Ser Glu Gln Ala Gly Arg Arg Asn Pro Pro Tyr Ala
530                 535                 540

Ala Val Phe His Ile Ser Asp Gln Thr Arg Arg Val Ile Val Arg Tyr
545                 550                 555                 560

Gly Glu Ile Glu Arg Tyr Leu Ala Glu His Pro Asp Thr Gly Ile Pro
                565                 570                 575

Gly Ser Arg Gly Leu Thr Ser Gly Leu Arg Val Met Ser Val Asp Leu
            580                 585                 590

Gly Leu Arg Thr Ser Ala Ala Ile Ser Val Phe Arg Val Ala His Arg
            595                 600                 605

Asp Glu Leu Thr Pro Asp Ala His Gly Arg Gln Pro Phe Phe Phe Pro
610                 615                 620

Ile His Gly Met Asp His Leu Val Ala Leu His Glu Arg Ser His Leu
625                 630                 635                 640

Ile Arg Leu Pro Gly Glu Thr Glu Ser Lys Lys Val Arg Ser Ile Arg
                645                 650                 655

Glu Gln Arg Leu Asp Arg Leu Asn Arg Leu Arg Ser Gln Met Ala Ser
            660                 665                 670

Leu Arg Leu Leu Val Arg Thr Gly Val Leu Asp Glu Gln Lys Arg Asp
            675                 680                 685

Arg Asn Trp Glu Arg Leu Gln Ser Ser Met Glu Arg Gly Gly Glu Arg
690                 695                 700

Met Pro Ser Asp Trp Trp Asp Leu Phe Gln Ala Gln Val Arg Tyr Leu
705                 710                 715                 720

Ala Gln His Arg Asp Ala Ser Gly Glu Ala Trp Gly Arg Met Val Gln
                725                 730                 735

Ala Ala Val Arg Thr Leu Trp Arg Gln Leu Ala Lys Gln Val Arg Asp
            740                 745                 750

Trp Arg Lys Glu Val Arg Arg Asn Ala Asp Lys Val Lys Ile Arg Gly
            755                 760                 765

Ile Ala Arg Asp Val Pro Gly Gly His Ser Leu Ala Gln Leu Asp Tyr
770                 775                 780

Leu Glu Arg Gln Tyr Arg Phe Leu Arg Ser Trp Ser Ala Phe Ser Val
785                 790                 795                 800

Gln Ala Gly Gln Val Val Arg Ala Glu Arg Asp Ser Arg Phe Ala Val
                805                 810                 815

Ala Leu Arg Glu His Ile Asp Asn Gly Lys Lys Asp Arg Leu Lys Lys
            820                 825                 830

Leu Ala Asp Arg Ile Leu Met Glu Ala Leu Gly Tyr Val Tyr Val Thr
            835                 840                 845

Asp Gly Arg Arg Ala Gly Gln Trp Gln Ala Val Tyr Pro Pro Cys Gln
850                 855                 860

Leu Val Leu Leu Glu Glu Leu Ser Glu Tyr Arg Phe Ser Asn Asp Arg
865                 870                 875                 880

Pro Pro Ser Glu Asn Ser Gln Leu Met Val Trp Ser His Arg Gly Val
                885                 890                 895

Leu Glu Glu Leu Ile His Gln Ala Gln Val His Asp Val Leu Val Gly
            900                 905                 910

Thr Ile Pro Ala Ala Phe Ser Ser Arg Phe Asp Ala Arg Thr Gly Ala
            915                 920                 925

Pro Gly Ile Arg Cys Arg Arg Val Pro Ser Ile Pro Leu Lys Asp Ala
```

```
                930               935               940
Pro Ser Ile Pro Ile Trp Leu Ser His Tyr Leu Lys Gln Thr Glu Arg
945                 950               955               960

Asp Ala Ala Leu Arg Pro Gly Glu Leu Ile Pro Thr Gly Asp Gly
                965               970               975

Glu Phe Leu Val Thr Pro Ala Gly Arg Gly Ala Ser Gly Val Arg Val
                980               985               990

Val His Ala Asp Ile Asn Ala Ala His Asn Leu Gln Arg Arg Leu Trp
            995               1000              1005

Glu Asn Phe Asp Leu Ser Asp Ile Arg Val Arg Cys Asp Arg Arg
        1010              1015              1020

Glu Gly Lys Asp Gly Thr Val Val Leu Ile Pro Arg Leu Thr Asn
        1025              1030              1035

Gln Arg Val Lys Glu Arg Tyr Ser Gly Val Ile Phe Thr Ser Glu
        1040              1045              1050

Asp Gly Val Ser Phe Thr Val Gly Asp Ala Lys Thr Arg Arg Arg
        1055              1060              1065

Ser Ser Ala Ser Gln Gly Glu Gly Asp Leu Ser Asp Glu Glu
        1070              1075              1080

Gln Glu Leu Leu Ala Glu Ala Asp Asp Ala Arg Glu Arg Ser Val
        1085              1090              1095

Val Leu Phe Arg Asp Pro Ser Gly Phe Val Asn Gly Gly Arg Trp
        1100              1105              1110

Thr Ala Gln Arg Ala Phe Trp Gly Met Val His Asn Arg Ile Glu
        1115              1120              1125

Thr Leu Leu Ala Glu Arg Phe Ser Val Ser Gly Ala Ala Glu Lys
        1130              1135              1140

Val Arg Gly
        1145

<210> SEQ ID NO 295
<211> LENGTH: 1108
<212> TYPE: PRT
<213> ORGANISM: Bacillus

<400> SEQUENCE: 295

Met Ala Ile Arg Ser Ile Lys Leu Lys Leu Lys Thr His Thr Gly Pro
1               5                   10                  15

Glu Ala Gln Asn Leu Arg Lys Gly Ile Trp Arg Thr His Arg Leu Leu
                20                  25                  30

Asn Glu Gly Val Ala Tyr Tyr Met Lys Met Leu Leu Leu Phe Arg Gln
            35                  40                  45

Glu Ser Thr Gly Glu Arg Pro Lys Glu Glu Leu Gln Glu Glu Leu Ile
        50                  55                  60

Cys His Ile Arg Glu Gln Gln Arg Asn Gln Ala Asp Lys Asn Thr
65                  70                  75                  80

Gln Ala Leu Pro Leu Asp Lys Ala Leu Glu Ala Leu Arg Gln Leu Tyr
                85                  90                  95

Glu Leu Leu Val Pro Ser Ser Val Gly Gln Ser Gly Asp Ala Gln Ile
            100                 105                 110

Ile Ser Arg Lys Phe Leu Ser Pro Leu Val Asp Pro Asn Ser Glu Gly
        115                 120                 125

Gly Lys Gly Thr Ser Lys Ala Gly Ala Lys Pro Thr Trp Gln Lys Lys
    130                 135                 140
```

```
Lys Glu Ala Asn Asp Pro Thr Trp Glu Gln Asp Tyr Glu Lys Trp Lys
145                 150                 155                 160

Lys Arg Arg Glu Glu Asp Pro Thr Ala Ser Val Ile Thr Thr Leu Glu
            165                 170                 175

Glu Tyr Gly Ile Arg Pro Ile Phe Pro Leu Tyr Thr Asn Thr Val Thr
            180                 185                 190

Asp Ile Ala Trp Leu Pro Leu Gln Ser Asn Gln Phe Val Arg Thr Trp
            195                 200                 205

Asp Arg Asp Met Leu Gln Gln Ala Ile Glu Arg Leu Leu Ser Trp Glu
            210                 215                 220

Ser Trp Asn Lys Arg Val Gln Glu Glu Tyr Ala Lys Leu Lys Glu Lys
225                 230                 235                 240

Met Ala Gln Leu Asn Glu Gln Leu Glu Gly Gln Glu Trp Ile Ser
                245                 250                 255

Leu Leu Glu Gln Tyr Glu Glu Asn Arg Glu Arg Glu Leu Arg Glu Asn
                260                 265                 270

Met Thr Ala Ala Asn Asp Lys Tyr Arg Ile Thr Lys Arg Gln Met Lys
            275                 280                 285

Gly Trp Asn Glu Leu Tyr Glu Leu Trp Ser Thr Phe Pro Ala Ser Ala
            290                 295                 300

Ser His Glu Gln Tyr Lys Glu Ala Leu Lys Arg Val Gln Gln Arg Leu
305                 310                 315                 320

Arg Gly Arg Phe Gly Asp Ala His Phe Phe Gln Tyr Leu Met Glu Glu
                325                 330                 335

Lys Asn Arg Leu Ile Trp Lys Gly Asn Pro Gln Arg Ile His Tyr Phe
                340                 345                 350

Val Ala Arg Asn Glu Leu Thr Lys Arg Leu Glu Glu Ala Lys Gln Ser
            355                 360                 365

Ala Thr Met Thr Leu Pro Asn Ala Arg Lys His Pro Leu Trp Val Arg
            370                 375                 380

Phe Asp Ala Arg Gly Gly Asn Leu Gln Asp Tyr Tyr Leu Thr Ala Glu
385                 390                 395                 400

Ala Asp Lys Pro Arg Ser Arg Arg Phe Val Thr Phe Ser Gln Leu Ile
                405                 410                 415

Trp Pro Ser Glu Ser Gly Trp Met Glu Lys Lys Asp Val Glu Val Glu
                420                 425                 430

Leu Ala Leu Ser Arg Gln Phe Tyr Gln Gln Val Lys Leu Leu Lys Asn
            435                 440                 445

Asp Lys Gly Lys Gln Lys Ile Glu Phe Lys Asp Lys Gly Ser Gly Ser
            450                 455                 460

Thr Phe Asn Gly His Leu Gly Gly Ala Lys Leu Gln Leu Glu Arg Gly
465                 470                 475                 480

Asp Leu Glu Lys Glu Glu Lys Asn Phe Glu Asp Gly Glu Ile Gly Ser
                485                 490                 495

Val Tyr Leu Asn Val Val Ile Asp Phe Glu Pro Leu Gln Glu Val Lys
            500                 505                 510

Asn Gly Arg Val Gln Ala Pro Tyr Gly Gln Val Leu Gln Leu Ile Arg
            515                 520                 525

Arg Pro Asn Glu Phe Pro Lys Val Thr Thr Tyr Lys Ser Glu Gln Leu
            530                 535                 540

Val Glu Trp Ile Lys Ala Ser Pro Gln His Ser Ala Gly Val Glu Ser
545                 550                 555                 560

Leu Ala Ser Gly Phe Arg Val Met Ser Ile Asp Leu Gly Leu Arg Ala
```

-continued

```
                565                 570                 575
Ala Ala Ala Thr Ser Ile Phe Ser Val Glu Glu Ser Ser Asp Lys Asn
            580                 585                 590

Ala Ala Asp Phe Ser Tyr Trp Ile Glu Gly Thr Pro Leu Val Ala Val
            595                 600                 605

His Gln Arg Ser Tyr Met Leu Arg Leu Pro Gly Glu Gln Val Glu Lys
            610                 615                 620

Gln Val Met Glu Lys Arg Asp Glu Arg Phe Gln Leu His Gln Arg Val
625                 630                 635                 640

Lys Phe Gln Ile Arg Val Leu Ala Gln Ile Met Arg Met Ala Asn Lys
            645                 650                 655

Gln Tyr Gly Asp Arg Trp Asp Glu Leu Asp Ser Leu Lys Gln Ala Val
            660                 665                 670

Glu Gln Lys Lys Ser Pro Leu Asp Gln Thr Asp Arg Thr Phe Trp Glu
            675                 680                 685

Gly Ile Val Cys Asp Leu Thr Lys Val Leu Pro Arg Asn Glu Ala Asp
            690                 695                 700

Trp Glu Gln Ala Val Val Gln Ile His Arg Lys Ala Glu Glu Tyr Val
705                 710                 715                 720

Gly Lys Ala Val Gln Ala Trp Arg Lys Arg Phe Ala Ala Asp Glu Arg
            725                 730                 735

Lys Gly Ile Ala Gly Leu Ser Met Trp Asn Ile Glu Glu Leu Glu Gly
            740                 745                 750

Leu Arg Lys Leu Leu Ile Ser Trp Ser Arg Arg Thr Arg Asn Pro Gln
            755                 760                 765

Glu Val Asn Arg Phe Glu Arg Gly His Thr Ser His Gln Arg Leu Leu
            770                 775                 780

Thr His Ile Gln Asn Val Lys Glu Asp Arg Leu Lys Gln Leu Ser His
785                 790                 795                 800

Ala Ile Val Met Thr Ala Leu Gly Tyr Val Tyr Asp Glu Arg Lys Gln
            805                 810                 815

Glu Trp Cys Ala Glu Tyr Pro Ala Cys Gln Val Ile Leu Phe Glu Asn
            820                 825                 830

Leu Ser Gln Tyr Arg Ser Asn Leu Asp Arg Ser Thr Lys Glu Asn Ser
            835                 840                 845

Thr Leu Met Lys Trp Ala His Arg Ser Ile Pro Lys Tyr Val His Met
850                 855                 860

Gln Ala Glu Pro Tyr Gly Ile Gln Ile Gly Asp Val Arg Ala Glu Tyr
865                 870                 875                 880

Ser Ser Arg Phe Tyr Ala Lys Thr Gly Thr Pro Gly Ile Arg Cys Lys
            885                 890                 895

Lys Val Arg Gly Gln Asp Leu Gln Gly Arg Arg Phe Glu Asn Leu Gln
            900                 905                 910

Lys Arg Leu Val Asn Glu Gln Phe Leu Thr Glu Glu Gln Val Lys Gln
            915                 920                 925

Leu Arg Pro Gly Asp Ile Val Pro Asp Asp Ser Gly Glu Leu Phe Met
            930                 935                 940

Thr Leu Thr Asp Gly Ser Gly Ser Lys Glu Val Val Phe Leu Gln Ala
945                 950                 955                 960

Asp Ile Asn Ala Ala His Asn Leu Gln Lys Arg Phe Trp Gln Arg Tyr
            965                 970                 975

Asn Glu Leu Phe Lys Val Ser Cys Arg Val Ile Val Arg Asp Glu Glu
            980                 985                 990
```

```
Glu Tyr Leu Val Pro Lys Thr Lys  Ser Val Gln Ala Lys  Leu Gly Lys
        995                 1000                1005

Gly Leu  Phe Val Lys Lys Ser  Asp Thr Ala Trp  Lys  Asp Val Tyr
    1010                 1015                1020

Val Trp  Asp Ser Gln Ala Lys  Leu Lys Gly Lys  Thr  Thr Phe Thr
    1025                 1030                1035

Glu Glu  Ser Glu Ser Pro Glu  Gln Leu Glu Asp  Phe  Gln Glu Ile
    1040                 1045                1050

Ile Glu  Glu Ala Glu Glu Ala  Lys Gly Thr Tyr  Arg  Thr Leu Phe
    1055                 1060                1065

Arg Asp  Pro Ser Gly Val Phe  Phe Pro Glu Ser  Val  Trp Tyr Pro
    1070                 1075                1080

Gln Lys  Asp Phe Trp Gly Glu  Val Lys Arg Lys  Leu  Tyr Gly Lys
    1085                 1090                1095

Leu Arg  Glu Arg Phe Leu Thr  Lys Ala Arg
    1100                 1105
```

```
<210> SEQ ID NO 296
<211> LENGTH: 5
<212> TYPE: PRT
<213> ORGANISM: artificial sequence
<220> FEATURE:
<223> OTHER INFORMATION: artificial sequence

<400> SEQUENCE: 296

Lys Lys Arg Lys Val
1               5

<210> SEQ ID NO 297
<211> LENGTH: 7
<212> TYPE: PRT
<213> ORGANISM: artificial sequence
<220> FEATURE:
<223> OTHER INFORMATION: artificial sequence

<400> SEQUENCE: 297

Pro Lys Lys Lys Arg Lys Val
1               5

<210> SEQ ID NO 298
<211> LENGTH: 11
<212> TYPE: PRT
<213> ORGANISM: artificial sequence
<220> FEATURE:
<223> OTHER INFORMATION: artificial sequence

<400> SEQUENCE: 298

Ser Gly Gly Ser Pro Lys Lys Lys Arg Lys Val
1               5                   10

<210> SEQ ID NO 299
<211> LENGTH: 4
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (4)..(4)
<223> OTHER INFORMATION: n is a, c, g, or t

<400> SEQUENCE: 299 tttn                                                              4
```

```
<210> SEQ ID NO 300
<211> LENGTH: 4
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (4)..(4)
<220> FEATURE:
<221> NAME/KEY: misc_feature
<222> LOCATION: (4)..(4)
<223> OTHER INFORMATION: n is a, c, g, or t

<400> SEQUENCE: 300 attn                                                                     4

<210> SEQ ID NO 301
<211> LENGTH: 4
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (4)..(4)
<223> OTHER INFORMATION: n is a, c, g, or t

<400> SEQUENCE: 301 gttn                                                                     4

<210> SEQ ID NO 302
<211> LENGTH: 4
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (4)..(4)
<223> OTHER INFORMATION: n is a, c, g, or t

<400> SEQUENCE: 302 cttn                                                                     4

<210> SEQ ID NO 303
<211> LENGTH: 3
<212> TYPE: DNA
<213> ORGANISM: artificial sequence
<220> FEATURE:
<223> OTHER INFORMATION: artificial sequence

<400> SEQUENCE: 303 ttc                                                                      3

<210> SEQ ID NO 304
<211> LENGTH: 3
<212> TYPE: DNA
<213> ORGANISM: artificial sequence
<220> FEATURE:
<223> OTHER INFORMATION: artificial sequence

<400> SEQUENCE: 304 ttg                                                                      3

<210> SEQ ID NO 305
<211> LENGTH: 3
```

```
<212> TYPE: DNA
<213> ORGANISM: artificial sequence
<220> FEATURE:
<223> OTHER INFORMATION: artificial sequence

<400> SEQUENCE: 305 tta                                                                    3

<210> SEQ ID NO 306
<211> LENGTH: 3
<212> TYPE: DNA
<213> ORGANISM: artificial sequence
<220> FEATURE:
<223> OTHER INFORMATION: artificial sequence

<400> SEQUENCE: 306 ttt                                                                    3

<210> SEQ ID NO 307
<211> LENGTH: 3
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (3)..(3)
<223> OTHER INFORMATION: n is a, c, g, or t

<400> SEQUENCE: 307 tan                                                                    3

<210> SEQ ID NO 308
<211> LENGTH: 3
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (3)..(3)
<223> OTHER INFORMATION: n is a, c, g, or t

<400> SEQUENCE: 308 tgn                                                                    3

<210> SEQ ID NO 309
<211> LENGTH: 3
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (3)..(3)
<223> OTHER INFORMATION: n is a, c, g, or t

<400> SEQUENCE: 309 tcn                                                                    3

<210> SEQ ID NO 310
<211> LENGTH: 3
<212> TYPE: DNA
<213> ORGANISM: artificial sequence
<220> FEATURE:
<223> OTHER INFORMATION: artificial sequence

<400> SEQUENCE: 310
```

```
atc                                                               3

<210> SEQ ID NO 311
<211> LENGTH: 28
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (8)..(28)
<223> OTHER INFORMATION: n is a, c, g, or t

<400> SEQUENCE: 311
nnnnnttnnn nnnnnnnnnn nnnnnnnn                                    28

<210> SEQ ID NO 312
<211> LENGTH: 28
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (24)..(28)
<223> OTHER INFORMATION: n is a, c, g, or t

<400> SEQUENCE: 312
nnnnnnnnnn nnnnnnnnnn naannnnn                                    28

<210> SEQ ID NO 313
<211> LENGTH: 43
<212> TYPE: DNA
<213> ORGANISM: artificial sequence
<220> FEATURE:
<223> OTHER INFORMATION: artificial sequence

<400> SEQUENCE: 313
ggaatcttaa ggaacaccat gaatagaatt gaaaaaaaat tga                   43

<210> SEQ ID NO 314
<211> LENGTH: 44
<212> TYPE: DNA
<213> ORGANISM: artificial sequence
<220> FEATURE:
<223> OTHER INFORMATION: artificial sequence

<400> SEQUENCE: 314
ggaatcttaa ggaacaccat gaatagaatt gaaaaaaaaa ttga                  44

<210> SEQ ID NO 315
<211> LENGTH: 45
<212> TYPE: DNA
<213> ORGANISM: artificial sequence
<220> FEATURE:
<223> OTHER INFORMATION: artificial sequence

<400> SEQUENCE: 315
ggaatcttaa ggaacaccat gaatagaatt gaaaaaaaaa attga                 45
```

```
<210> SEQ ID NO 316
<211> LENGTH: 122
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (88)..(105)
<223> OTHER INFORMATION: n is a, c, g, or t
<220> FEATURE:
<221> NAME/KEY: misc_feature
<222> LOCATION: (106)..(122)
<223> OTHER INFORMATION: n is optionally not present

<400> SEQUENCE: 316
gtctaaagga cagaattttt caacgggtgt gccaatggcc actttccagg tggcaaagcc      60
cgttgaactt ctaagcagaa gtggcacnnn nnnnnnnnnn nnnnnnnnnn nnnnnnnnnn     120 nn                                                                   122

<210> SEQ ID NO 317
<211> LENGTH: 120
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (86)..(103)
<223> OTHER INFORMATION: n is a, c, g, or t
<220> FEATURE:
<221> NAME/KEY: misc_feature
<222> LOCATION: (104)..(120)
<223> OTHER INFORMATION: n is optionally not present

<400> SEQUENCE: 317
gtctaaagga cagaattttt caacgggtgt gccaatggcc actttccagg tggcaaagcc      60
cgttgaactt caagcgaagt ggcacnnnnn nnnnnnnnnn nnnnnnnnnn nnnnnnnnnn     120
```

SYSTEM AND METHOD FOR GENOME EDITING

CROSS-REFERENCE TO RELATED APPLICATIONS

This is the U.S. National Stage of International Application No. PCT/CN2017/118948, filed Dec. 27, 2017, which is incorporated by reference herein.

TECHNICAL FIELD

The invention relates to the field of genetic engineering. In particular, the present invention relates to novel genome editing systems and methods. More specifically, the present invention relates to a novel CRISPR-C2c1 system capable of efficiently editing the genome of a cell and the uses thereof.

BACKGROUND

CRISPR (Clustered regular interspaced short palindromic repeats) system is an immune system that is generated during the evolution of bacteria to protect against foreign gene invasion. Among them, the type II CRISPR-Cas9 system is a system for DNA cleavage by a Cas9 protein mediated by two small RNAs (crRNA and tracrRNA) or an artificially synthetized small RNA (sgRNA), and is the simplest system in the first discovered (Type I, II, III) three CRISPR systems. Due to its simplicity and ease of operation, the system was successfully engineered and achieved eukaryotic genome editing in 2013. CRISPR/Cas9 system quickly became the most popular technology in life sciences.

In 2015, Zhang et al. discovered a new type V-A gene editing system through sequence alignment and systematic analysis, the CRISPR-Cpf1 system, which is different from the CRISPR-Cas9 system. The system requires only one small RNA (crRNA) to mediate genome editing.

In 2015, Shmakov et al. also identified new genome editing systems (Molecular Cell 60, 385-397, Nov. 5, 2015): C2c1 (V-B), C2c2 (VI) and C2c3 (V-C) systems. Among them, AacC2c1 from *Alicyclobacillus acidoterrestris* was confirmed to achieve DNA cleavage; however, its activity was limited by, for example, temperature. The AacC2c1 system was unable to cleave DNA below 40° C. And, there is no proof that the AacC2c1 system can achieve genome editing in eukaryotes.

To make gene editing easier, there is still a need in the art for a system that enables efficient genome editing.

BRIEFLY DESCRIPTION OF THE INVENTION

The inventors have identified a novel CRISPR-C2c1 system for genome editing in mammalian cells. The C2c1 nuclease identified by the present inventors shows high temperature resistance and acid and alkali resistance in in vitro experiments. Moreover, the present inventors optimize the sgRNA of the identified CRISPR-C2c1 system to greatly shorten its length without affecting its targeting efficiency. Finally, the inventors also engineered the C2c1 protein itself to convert it from an endonuclease to a dead C2c1 (dC2c1), expanding its use.

In one aspect, the present invention provides a genome editing system for site-directed modification of a target sequence in the genome of a cell, comprising at least one of the following i) to v):

i) a C2c1 protein or variant thereof, and a guide RNA;
ii) an expression construct comprising a nucleotide sequence encoding a C2c1 protein or variant thereof, and a guide RNA;
iii) a C2c1 protein or variant thereof, and an expression construct comprising a nucleotide sequence encoding a guide RNA;
iv) an expression construct comprising a nucleotide sequence encoding a C2c1 protein or variant thereof, and an expression construct comprising a nucleotide sequence encoding a guide RNA;
v) an expression construct comprising a nucleotide sequence encoding a C2c1 protein or variant thereof and a nucleotide sequence encoding a guide RNA;

wherein the guide RNA is capable of forming a complex with the C2c1 protein or variant thereof and targeting the C2c1 protein or the variant thereof to the target sequence in the genome of the cell, resulting in substitution, deletion and/or addition of one or more nucleotides in the target sequence. In some embodiments, the C2c1 protein is a C2c1 protein derived from *Alicyclobacillus acidiphilus* or *Alicyclobacillus kakegawensis*.

In another aspect, the present invention provides a method of site-directed modifying a target sequence in the genome of a cell, comprising introducing the genome editing system of the invention into the cell.

In another aspect, the invention provides a method of treating a disease in a subject in need thereof, comprising delivering to the subject an effective amount of the genome editing system of the invention to modify a gene related to the disease in the subject.

In another aspect, the invention provides a use of the genome editing system of the invention for the preparation of a pharmaceutical composition for treating a disease in a subject in need thereof, wherein the genome editing system is for modifying a gene related to the disease in the subject.

In another aspect, the invention provides a pharmaceutical composition for treating a disease in a subject in need thereof, comprising the genome editing system of the invention and a pharmaceutically acceptable carrier, wherein the genome editing system is for modifying a gene related to the disease in the subject.

DESCRIPTION OF THE DRAWINGS

FIGS. 1A-1C and FIGS. 2A-2E show the in vitro nuclease activity analysis results of AaC2c1.

FIGS. 3A-3E and FIGS. 4A-4H show the genome editing activity of AaC2c1 and AkC2c1 in mammalian cells.

FIGS. 5A-5E and FIGS. 6A-6M show the optimization of the single guide RNA (sgRNA) for mediating AaC2c1 genome editing.

FIGS. 7A-7E shows the effect of length of target sequence and number of mismatched on AaC2c1 editing activity.

FIGS. 9A-9D show the identification and mutational analysis of key catalytic residues of AaC2c1.

SEQUENCE LISTING

Figure 1A:
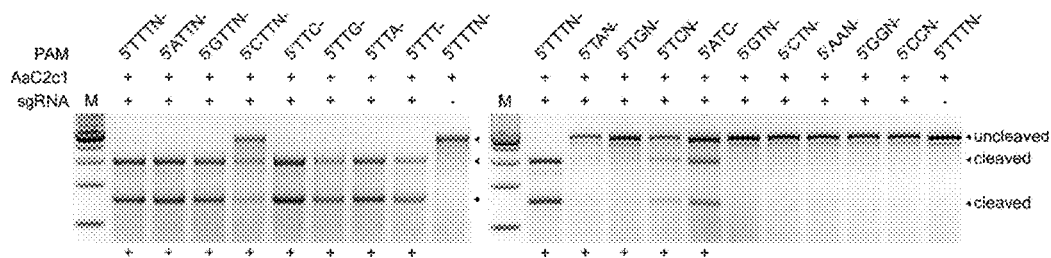

The Sequence Listing is submitted as an ASCII text file in the form of the filed named "9763-103651-01 Sequence- _Listing.txt", (155,005 bytes), which was created on Aug. 15, 2022, which is incorporated by reference herein.

DETAILED DESCRIPTION OF THE INVENTION

In the present invention, the scientific and technical terms used herein have the meaning as commonly understood by a person skilled in the art unless otherwise specified. Also, the protein and nucleic acid chemistry, molecular biology, cell and tissue culture, microbiology, immunology related terms, and laboratory procedures used herein are terms and routine steps that are widely used in the corresponding field. For example, standard recombinant DNA and molecular cloning techniques used in the present invention are well known to those skilled in the art and are more fully described in the following document: Sambrook, J., Fritsch, E. F. and Maniatis, T., *Molecular Cloning: A Laboratory Manual*; Cold Spring Harbor Laboratory Press: Cold Spring Harbor, 1989 (hereinafter referred to as "Sambrook").

In one aspect, the present invention provides a genome editing system for site-directed modification of a target sequence in the genome of a cell, comprising at least one of the following i) to v):
  i) a C2c1 protein or variant thereof, and a guide RNA;
  ii) an expression construct comprising a nucleotide sequence encoding a C2c1 protein or variant thereof, and a guide RNA;
  iii) a C2c1 protein or variant thereof, and an expression construct comprising a nucleotide sequence encoding a guide RNA;
  iv) an expression construct comprising a nucleotide sequence encoding a C2c1 protein or variant thereof, and an expression construct comprising a nucleotide sequence encoding a guide RNA;
  v) an expression construct comprising a nucleotide sequence encoding a C2c1 protein or the variant thereof and a nucleotide sequence encoding a guide RNA;
  wherein the guide RNA is capable of forming a complex with the C2c1 protein or variant thereof and targeting the C2c1 protein or variant thereof to a target sequence in the genome of the cell, resulting in substitution, deletion and/or addition of one or more nucleotides in the target sequence.

"Genome" as used herein encompasses not only chromosomal DNA present in the nucleus, but also organellar DNA present in the subcellular components (e.g., mitochondria, plastids) of the cell.

"C2c1 nuclease", "C2c1 protein" and "C2c1" are used interchangeably herein and refer to an RNA-directed nuclease comprising a C2c1 protein or a fragment thereof. C2c1 has a guide RNA-mediated DNA binding activity and DNA cleavage activity, and can target and cleave DNA target sequences to form DNA double-strand breaks (DSBs) under the guidance of a guide RNA. DSB can activate the intracellular intrinsic repair mechanism, non-homologous end joining (NHEJ) and homologous recombination (HR), to repair DNA damage in cells. During the repair process, the specific DNA sequence is subjected to site-directed editing.

In some embodiments, the C2c1 protein is a C2c1 protein derived from *Alicyclobacillus acidiphilus* (AaC2c1). For example, the C2c1 protein is AaC2c1 protein derived from *Alicyclobacillus acidiphilus* NBRC 100859. In some embodiments, AaC2c1 protein comprises an amino acid sequence set forth in SEQ ID NO:1.

The inventors have surprisingly found that the AaC2c1 protein has RNA-directed DNA cleavage activity over a wide temperature range of about 4° C. to about 100° C., with optimal activity at a temperature of about 30° C. to about 60° C. In addition, the AaC2c1 protein has RNA-directed DNA cleavage activity over a wide pH range of about pH 1.0 to about pH 12.0, with optimal activity at a pH of about 1.0 to about pH 8.0. Thus, the genome editing system of the present invention can work under a variety of temperature and pH conditions.

In some embodiments, the variant of the C2c1 protein comprises an amino acid sequence having at least 80%, at least 85%, at least 90%, at least 95%, at least 96%, at least 97%, at least 98%, at least 99% sequence identity with the wild-type AaC2c1 protein set forth in SEQ ID NO:1, and has the RNA-mediated DNA binding activity and/or DNA cleavage activity of the wild-type AaC2c1 protein.

In some embodiments, the variant of the C2c1 protein comprises an amino acid sequence having one or more amino acid residue substitution, deletion or addition as compared to SEQ ID NO: 1 and has the RNA-mediated DNA binding activity and/or DNA cleavage activity of the wild-type AaC2c1 protein. For example, the variant of the C2c1 protein comprises an amino acid sequence having 1, 2, 3, 4, 5, 6, 7, 8, 9, or 10 amino acid residue substitution, deletion or addition as compared to SEQ ID NO: 1. In some embodiments, the amino acid substitution is a conservative substitution.

In some other embodiments, the C2c1 protein is a C2c1 protein derived from *Alicyclobacillus kakegawensis* (AkC2c1). For example, the AkC2c1 protein is derived from *Alicyclobacillus kakegawensis* NBRC 103104. In some embodiments, the AkC2c1 protein comprises an amino acid sequence set forth in SEQ ID NO:5.

In some embodiments, the variant of the C2c1 protein comprises an amino acid sequence having at least 80%, at least 85%, at least 90%, at least 95%, at least 96%, at least 97%, at least 98%, at least 99% sequence identity with the wild-type AkC2c1 protein set forth in SEQ ID NO:5, and has the RNA-mediated DNA binding activity and/or DNA cleavage activity of the wild-type AkC2c1 protein.

In some embodiments, the variant of the C2c1 protein comprises an amino acid sequence having one or more amino acid residue substitution, deletion or addition as compared SEQ ID NO: 4 and has the RNA-mediated DNA binding activity and/or DNA cleavage activity of the wild-type AkC2c1 protein. For example, the variant of the C2c1 protein comprises an amino acid sequence having 1, 2, 3, 4, 5, 6, 7, 8, 9, or 10 amino acid residue substitution, deletion or addition as compared SEQ ID NO: 4. In some embodiments, the amino acid substitution is a conservative substitution.

"Polypeptide," "peptide," and "protein" are used interchangeably in the present invention to refer to a polymer of amino acid residues. The terms apply to an amino acid polymer in which one or more amino acid residues is artificial chemical analogue of corresponding naturally occurring amino acid(s), as well as to a naturally occurring amino acid polymer. The terms "polypeptide," "peptide," "amino acid sequence," and "protein" may also include modified forms including, but not limited to, glycosylation, lipid ligation, sulfation, 7 carboxylation of glutamic acid residues, and ADP-ribosylation.

Sequence "identity" has recognized meaning in the art, and the percentage of sequence identity between two nucleic acids or polypeptide molecules or regions can be calculated using disclosed techniques. Sequence identity can be measured along the entire length of a polynucleotide or polypeptide or along a region of the molecule. (See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Although there are many methods for measuring the identity between two polynucleotides or polypeptides, the term "identity" is well known to the skilled person (Carrillo, H. & Lipman, D., SIAM J Applied Math 48: 1073 (1988)).

Suitable conservative amino acid substitution in peptides or proteins are known to those skilled in the art and can generally be carried out without altering the biological activity of the resulting molecule. In general, one skilled in the art recognizes that a single amino acid substitution in a non-essential region of a polypeptide does not substantially alter biological activity (See, for example, Watson et al., Molecular Biology of the Gene, 4th Edition, 1987, The Benjamin/Cummings Pub. co., p. 224).

In some embodiments, the variant of the C2c1 protein comprises a nuclease-dead C2c1 protein (dC2c1). The nuclease-dead C2c1 protein refers to a C2c1 protein that retains the RNA-mediated DNA-binding activity but does not have DNA cleavage activity.

In some embodiments, in dC2c1, the amino acid corresponding to position 785 of the wild type AaC2c1 protein is substituted. In some specific embodiments, dC2c1 comprises an amino acid substitution R785A relative to the wild-type AaC2c1 protein. In some specific embodiments, dC2c1 comprises an amino acid sequence set forth in SEQ ID NO:4.

In some embodiments, the variant of the C2c1 protein is a fusion protein of dC2c1 and a deaminase. For example, dC2c1 and deaminase in the fusion protein can be linked by a linker such as a peptide linker.

As used herein, "deaminase" refers to an enzyme that catalyzes a deamination reaction. In some embodiments of the invention, the deaminase refers to a cytosine deaminase capable of accepting single-stranded DNA as a substrate and capable of catalyzing the deamination of cytidine or deoxycytidine to uracil or deoxyuracil, respectively. In some embodiments of the invention, the deaminase refers to adenine deaminase capable of accepting single-stranded DNA as a substrate and capable of catalyzing adenosine or deoxyadenosine (A) into inosine (I). Base editing in the target DNA sequence, such as C to T conversion or A to G conversion, can be achieved by using a fusion protein of a C2c1 variant and a deaminase. A variety of suitable cytosine deaminases or adenine deaminases that accept single-stranded DNA as a substrate are known in the art.

In some embodiments of the present invention, the C2c1 protein or variant thereof in the present invention may further comprise a nuclear localization sequence (NLS). In general, one or more NLSs in the C2c1 protein or variant thereof should be of sufficient strength to drive the C2c1 protein or variant thereof to accumulate in the cell nucleus to an amount enabling its base editing function. In general, the intensity of nuclear localization activity is determined by the number, location, one or more specific NLSs used of the NLS in the C2c1 protein or variant thereof, or a combination of these factors.

In some embodiments of the present invention, the NLS of the C2c1 protein or variant thereof in the present invention may be located at the N-terminus and/or C-terminus. In some embodiments, the C2c1 protein or variant thereof comprises about 1, 2, 3, 4, 5, 6, 7, 8, 9, 10 or more NLSs. In some embodiments, the C2c1 protein or variant thereof comprises about 1, 2, 3, 4, 5, 6, 7, 8, 9, 10 or more NLS at or near the N-terminus. In some embodiments, the C2c1 protein or variant thereof comprises about 1, 2, 3, 4, 5, 6, 7, 8, 9, 10 or more NLSs at or near the C-terminus. In some embodiments, the C2c1 protein or variant thereof comprises a combination of these, such as comprises one or more NLSs at the N-terminus and one or more NLSs at the C-terminus. When there is more than one NLS, each can be selected to be independent of other NLSs. In some preferred embodiments of the present invention, the C2c1 protein or variant thereof comprises two NLSs, for example, the two NLSs are located at the N-terminus and the C-terminus, respectively.

In general, NLS consists of one or more short sequences of positively charged lysine or arginine exposed on the surface of the protein, but other types of NLS are also known. Non-limiting examples of NLS include: KKRKV (SEQ ID NO: 296, PKKKRKV (SEQ ID NO: 297), or SGGSPKKKRKV (SEQ ID NO: 298).

Furthermore, depending on the location of the DNA to be edited, the C2c1 protein or variant thereof in the present invention may also include other localization sequences, such as cytoplasmic localization sequences, chloroplast localization sequences, mitochondrial localization sequences, and the like.

In some embodiments of the invention, the target sequence is 18-35 nucleotides in length, preferably 20 nucleotides in length. In some embodiments of the invention, the sequence flanking 5'-end of the target sequence is a protospacer adjacent motif (PAM) sequence selected from 5'TTTN-3' (SEQ ID NO: 299), 5'ATTN-3'(SEQ ID NO: 300), 5'GTTN-3'(SEQ ID NO: 301), 5'CTTN-3'(SEQ ID NO: 302), 5'TTC-3'(SEQ ID NO: 303), 5'TTG-3'(SEQ ID NO: 304), 5'TTA-3'(SEQ ID NO: 305), 5'TTT-3'(SEQ ID NO: 306), 5'TAN-3'(SEQ ID NO: 307), 5'TGN-3'(SEQ ID NO: 308), 5'TCN-3'(SEQ ID NO: 209), and 5'ATC-3'(SEQ ID NO: 310), preferably 5'TTTN-3'(SEQ ID NO: 299), wherein N is selected from A, G, C and T.

In the present invention, the target sequence to be modified may be located at any location in the genome, for example, in a functional gene such as a protein-encoding gene, or may be, for example, located in a gene expression regulatory region such as a promoter region or an enhancer region, thereby the gene functional modification or gene expression modification can be achieved. The substitution, deletion and/or addition in the target sequence of the genome can be detected by T7EI, PCR/RE or sequencing methods.

"guide RNA" and "gRNA" can be used interchangeably herein, typically composed of crRNA and tracrRNA molecules that are partially complementary to each other to form a complex, wherein the crRNA comprises a sequence that is sufficiently identical to the target sequence to hybridize to the complement of the target sequence and direct the CRISPR complex (C2c1+crRNA+tracrRNA) to sequence specifically bind to the target sequence.

However, a single guide RNA (sgRNA) containing both crRNA and tracrRNA characteristics can be designed and used.

In some embodiments of the invention, the guide RNA is a complex formed by partial complement of a crRNA and a tracrRNA. In some embodiments, the tracrRNA is encoded by the nucleotide sequence: 5'-GTCTAAAGGACAGAAT-TTTTCAACGGGTGTGCCAATGGC-CACTTTCCAGGTGGC AAAGCCCGTTGAACTTCT-CAAAAAGAACGCTCGCTCAGTGTTCTGAC-3' (SEQ ID NO: 15). In some embodiments, the crRNA is encoded by the nucleotide sequence of: 5'-GTCGGATCACT-GAGCGAGCGATCTGAGAAGTGGCAC-Nx-3'(SEQ ID NO: 16), wherein Nx represents nucleotide sequence that consists of x consecutive nucleotides, N is independently selected from A, G, C and T; x is an integer of 18≤x≤35. Preferably, x=20. In some embodiments, the sequence Nx (spacer sequence) is capable of specifically hybridizing to the complement of the target sequence.

In some embodiments of the invention, the guide RNA is a sgRNA. In some particular embodiments, the sgRNA is encoded by a nucleotide sequence selected from the group consisting of:

(SEQ ID NO: 17)
5'-GTCTAAAGGACAGAATTTTTCAACGGGTGTGCCAATGGCCACTTTCC

AGGTGGCAAAGCCCGTTGAACTTCTCAAAAAGAACGCTCGCTCAGTGTTC

TGACGTCGGATCACTGAGCGAGCGATCTGAGAAGTGGCAC-N$_x$-3';

(SEQ ID NO: 18)
5'-AACTGTCTAAAGGACAGAATTTTTCAACGGGTGTGCCAATGGCCACT

TTCCAGGTGGCAAAGCCCGTTGAACTTCTCAAAAAGAACGCTCGCTCAGT

GTTCTGACGTCGGATCACTGAGCGAGCGATCTGAGAAGTGGCAC-N$_x$-

3';

(SEQ ID NO: 19)
5'-CTGTCTAAAGGACAGAATTTTTCAACGGGTGTGCCAATGGCCACTTT

CCAGGTGGCAAAGCCCGTTGAACTTCTCAAAAAGAACGCTCGCTCAGTGT

TCTGACGTCGGATCACTGAGCGAGCGATCTGAGAAGTGGCAC-N$_x$-3';

(SEQ ID NO: 20)
5'-GTCTAAAGGACAGAATTTTTCAACGGGTGTGCCAATGGCCACTTTCC

AGGTGGCAAAGCCCGTTGAACTTCTCAAAAAGAACGCTCGCTCAGTGTTA

TCACTGAGCGAGCGATCTGAGAAGTGGCAC-N$_x$-3';

(SEQ ID NO: 21)
5'-GTCTAAAGGACAGAATTTTTCAACGGGTGTGCCAATGGCCACTTTCC

AGGTGGCAAAGCCCGTTGAACTTCTCAAAAAGAACGATCTGAGAAGTGGC

AC-N$_x$-3';

(SEQ ID NO: 22)
5'-GTCTAAAGGACAGAATTTTTCAACGGGTGTGCCAATGGCCACTTTCC

AGGTGGCAAAGCCCGTTGAACTTCTCAAAAAGCTGAGAAGTGGCAC-N$_x$-

3';

(SEQ ID NO: 23)
5'-GTCTAAAGGACAGAATTTTTCAACGGGTGTGCCAATGGCCACTTTCC

AGGTGGCAAAGCCCGTTGAACTTCTCAAAGCTGAGAAGTGGCAC-N$_x$-

3';

(SEQ ID NO: 24)
5'-GTCTAAAGGACAGAATTTTTCAACGGGTGTGCCAATGGCCACTTTCC

AGGTGGCAAAGCCCGTTGAACTTCTCAAAACTGAGAAGTGGCAC-N$_x$-

3';

(SEQ ID NO: 25)
5'-GTCTAAAGGACAGAATTTTTCAACGGGTGTGCCAATGGCCACTTTCC

AGGTGGCAAAGCCCGTTGAACTTCAAGCGAGAAGTGGCAC-N$_x$-3';

(SEQ ID NO: 316)
5'-GTCTAAAGGACAGAATTTTTCAACGGGTGTGCCAATGGCCACTTTCC

AGGTGGCAAAGCCCGTTGAACTTCTAAGCAGAAGTGGCAC-N$_x$-3';

and (SEQ ID NO: 316)
5'-GTCTAAAGGACAGAATTTTTCAACGGGTGTGCCAATGGCCACTTTCC

AGGTGGCAAAGCCCGTTGAACTTCAAGCGAAGTGGCAC-N$_x$-3';

wherein Nx represents nucleotide sequence that consists of x consecutive nucleotides (spacer sequence), N is independently selected from A, G, C and T; x is an integer of 18≤x≤35, preferably, x=20. In some embodiments, the sequence Nx (spacer sequence) is capable of specifically hybridizing to the complement of the target sequence. The sequence in sgRNA excluding Nx is the scaffold sequence of sgRNA.

"Polynucleotide", "nucleic acid sequence", "nucleotide sequence" or "nucleic acid fragment" are used interchangeably and are single-stranded or double-stranded RNA or DNA polymers, optionally containing synthetic, non-natural or altered nucleotide bases. Nucleotides are referred to by their single letter names as follows: "A" is adenosine or deoxyadenosine (corresponding to RNA or DNA, respectively), "C" means cytidine or deoxycytidine, "G" means guanosine or deoxyguanosine, "U" represents uridine, "T" means deoxythymidine, "R" means purine (A or G), "Y" means pyrimidine (C or T), "K" means G or T, "H" means A or C or T, "I" means inosine, and "N" means any nucleotide.

To obtain efficient expression in the target cells, in some embodiments of the present invention, the nucleotide sequence encoding the C2c1 protein or variant thereof is codon optimized for the organism from which the cell to be genome edited is derived.

Codon optimization refers to the replacement of at least one codon (e.g., about or more than about 1, 2, 3, 4, 5, 10, 15, 20, 25, 50 or more codons) of a native sequence by a codon that is used more frequently or most frequently in the gene of the host cell, modifying the nucleic acid sequence while maintaining the native amino acid sequence to enhance expression in the host cell of interest. Different species show specific preferences for certain codons of a particular amino acid. Codon preference (difference in codon usage between organisms) is often associated with the efficiency of translation of messenger RNA (mRNA), which is believed to depend on the nature of the translated codon and the availability of specific transfer RNA (tRNA) molecules. The advantages of selected tRNAs within cells generally reflect the most frequently used codons for peptide synthesis. Therefore, genes can be customized to be best gene expressed in a given organism based on codon optimization. The codon usage table can be easily obtained, for example, in the Codon Usage Database available at www.kazusa.orjp/codon/, and these tables can be adjusted in different ways. See, Nakamura Y. et. al. "Codon usage tabulated from the international DNA sequence databases: status for the year 2000 Nucl. Acids Res, 28: 292 (2000).

In some embodiments of the invention, the nucleotide sequence encoding a C2c1 protein and variant thereof is codon optimized for human. In some embodiments, the codon-optimized nucleotide sequence encoding a C2c1 protein is selected from SEQ ID NO: 3 or 7.

In some embodiments of the present invention, the nucleotide sequence encoding the C2c1 protein and variant thereof and/or the nucleotide sequence encoding the guide RNA is operably linked to an expression regulatory element such as a promoter.

As used in the present invention, "expression construct" refers to a vector such as a recombinant vector that is suitable for expression of a nucleotide sequence of interest in an organism. "Expression" refers to the production of a functional product. For example, expression of a nucleotide sequence may refer to the transcription of a nucleotide sequence (e.g., transcription to produce mRNA or functional RNA) and/or the translation of RNA into a precursor or mature protein. The "expression construct" of the present invention may be a linear nucleic acid fragment, a circular plasmid, a viral vector or, in some embodiments, an RNA that is capable of translation (such as mRNA).

The "expression construct" of the present invention may comprise regulatory sequences and nucleotide sequences of interest from different origins, or regulatory sequences and nucleotide sequences of interest from the same source but arranged in a manner different from that normally occurring in nature.

"Regulatory sequence" and "regulatory element" are used interchangeably to refer to a nucleotide sequence that is located upstream (5' non-coding sequence), middle or downstream (3' non-coding sequence) of a coding sequence and affects the transcription, RNA processing or stability or translation of the relevant coding sequence. Regulatory sequences may include, but are not limited to, promoters, translation leaders, introns and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell. The promoter may be a constitutive promoter or tissue-specific promoter or developmentally-regulated promoter or inducible promoter.

"Constitutive promoter" refers to a promoter that may in general cause the gene to be expressed in most cases in most cell types. "Tissue-specific promoter" and "tissue-preferred promoter" are used interchangeably and mean that they are expressed primarily but not necessarily exclusively in one tissue or organ, but also in a specific cell or cell type. "Developmentally-regulated promoter" refers to a promoter whose activity is dictated by developmental events. "Inducible promoter" selectively expresses operably-linked DNA sequences in response to an endogenous or exogenous stimulus (environment, hormones, chemical signals, etc.).

As used herein, the term "operably linked" refers to the linkage of a regulatory element (e.g., but not limited to, a promoter sequence, a transcription termination sequence, etc.) to a nucleic acid sequence (e.g., a coding sequence or an open reading frame) such that transcription of the nucleotide sequence is controlled and regulated by the transcriptional regulatory element. Techniques for operably linking regulatory element regions to nucleic acid molecules are known in the art.

Examples of promoters that can be used in the present invention include, but are not limited to, the polymerase (pol) I, pol II or pol III promoters. Examples of the pol I promoter include the gallus RNA pol I promoter. Examples of the pol II promoters include, but are not limited to, the immediate-early cytomegalovirus (CMV) promoter, the Rous sarcoma virus long terminal repeat (RSV-LTR) promoter, and the immediate-early simian virus 40 (SV40) promoter. Examples of pol III promoters include the U6 and H1 promoters. An inducible promoter such as a metallothionein promoter can be used. Other examples of promoters include the T7 phage promoter, the T3 phage promoter, the β-galactosidase promoter, and the Sp6 phage promoter, and the like. Promoters that can be used in plants include, but are not limited to, cauliflower mosaic virus 35S promoter, maize Ubi-1 promoter, wheat U6 promoter, rice U3 promoter, maize U3 promoter, rice actin promoter.

The cell that can be edited by the method of the present invention preferably is an eukaryotic cell, including but not limited to a mammalian cell such as a cell of human, mouse, rat, monkey, dog, pig, sheep, cattle, cat; a cell of poultry such as chicken, duck, goose; a cell of plants including monocots and dicots, such as rice, corn, wheat, sorghum, barley, soybean, peanut and *Arabidopsis thaliana* and so on. In some embodiments of the invention, the cell is a eukaryotic cell, preferably a mammalian cell, more preferably a human cell.

In another aspect, the present invention provides a method of modifying a target sequence in the genome of a cell, comprising introducing the genome editing system of the invention into the cell, whereby the guide RNA targets the C2c1 protein or variant thereof to the target sequence in the genome of the cell. In some embodiments, the targeting results in one or more nucleotides being substituted, deleted and/or added in the target sequence.

"Introduction" of a nucleic acid molecule (e.g., plasmid, linear nucleic acid fragment, RNA, etc.) or protein of the invention into a cell means that the nucleic acid or protein is used to transform a cell such that the nucleic acid or protein is capable of functioning in the cell. As used in the present invention, "transformation" includes both stable and transient transformations. "Stable transformation" refers to the introduction of exogenous nucleotide sequence into the genome, resulting in the stable inheritance of foreign sequence. Once stably transformed, the exogenous nucleic acid sequence is stably integrated into the genome of the organism and any of its successive generations. "Transient transformation" refers to the introduction of a nucleic acid molecule or protein into a cell, executing its function without the stable inheritance of an exogenous sequence. In transient transformation, the exogenous nucleic acid sequence is not integrated into the genome.

Methods that can be used to introduce the genome editing system of the present invention into a cell include, but are not limited to, calcium phosphate transfection, protoplast fusion, electroporation, lipofection, microinjection, viral infection (e.g., baculovirus, vaccinia virus, adenovirus, adeno-associated virus, lentivirus and other viruses), gene gun method, PEG-mediated protoplast transformation, *Agrobacterium*-mediated transformation.

In some embodiments, the method of the invention is performed in vitro. For example, the cell is an isolated cell. In some embodiments, the cell is a CAR-T cell. In some embodiments, the cell is an induced embryonic stem cell.

In other embodiments, the method of the invention may also be performed in vivo. For example, the cell is a cell within an organism, and the system of the present invention can be introduced into the cell in vivo by, for example, a virus-mediated method. For example, the cell can be a tumor cell within a patient.

In another aspect, the present invention provides a method of producing a genetically modified cell, comprising introducing the genome editing system of the present invention into a cell, whereby the guide RNA targets the C2c1 protein or variant thereof to a target sequence in the genome of cell, resulting in one or more nucleotides being substituted, deleted and/or added in the target sequence.

In another aspect, the invention also provides a genetically modified organism comprising a genetically modified cell produced by the method of the invention or a progeny cell thereof.

As used herein, "organism" includes any organism that is suitable for genome editing, eukaryotes are preferred. Examples of the organism include, but are not limited to, mammals such as human, mouse, rat, monkey, dog, pig, sheep, cattle, cat; poultry such as chicken, duck, goose; plants including monocots and dicots such as rice, corn, wheat, sorghum, barley, soybean, peanut, *Arabidopsis* and the like. In some embodiments of the invention, the organism is eukaryote, preferably a mammal, and more preferably a human.

A "genetically modified organism" or "genetically modified cell" includes the organism or the cell which comprises within its genome an exogenous polynucleotide or a modified gene or modified expression regulatory sequence. For example, the exogenous polynucleotide is stably integrated within the genome of the organism or the cell such that the polynucleotide is passed on to successive generations. The exogenous polynucleotide may be integrated into the genome alone or as part of a recombinant DNA construct. The modified gene or modified expression regulatory sequence means that, in the genome of the organism or the cell, said sequence comprises one or more nucleotide substitution, deletion, or addition. "Exogenous" in reference to a sequence means a sequence from a foreign species, or refers to a sequence in which significant changes in composition and/or locus occur from its native form through deliberate human intervention if from the same species.

In another aspect, the invention provides a gene expression regulatory system based on a nuclease-dead C2c1 protein of the invention. This system, although not changing the sequence of the target gene, is also defined as a genome editing system within the scope herein.

In some embodiments, the gene expression regulation system is a gene suppressing or silencing system, comprising one of the following:
  i) a nuclease-dead C2c1 protein or a fusion protein of the nuclease-dead C2c1 protein and a transcriptional repressor protein, and a guide RNA;
  ii) an expression construct comprising a nucleotide sequence encoding a nuclease-dead C2c1 protein or a fusion protein of the nuclease-dead C2c1 protein and a transcriptional repressor protein, and a guide RNA;
  iii) a nuclease-dead C2c1 protein or a fusion protein of the nuclease-dead C2c1 protein and a transcriptional repressor protein, and an expression construct comprising a nucleotide sequence encoding a guide RNA;
  iv) an expression construct comprising a nucleotide sequence encoding a nuclease-dead C2c1 protein or a fusion protein of the nuclease-dead C2c1 protein and a transcriptional repressor protein, and an expression construct comprising a nucleotide sequence encoding a guide RNA; or
  v) an expression construct comprising a nucleotide sequence encoding a nuclease-dead C2c1 protein or a fusion protein of the nuclease-dead C2c1 protein and a transcriptional repressor protein and a nucleotide sequence encoding a guide RNA.

The definition of the nuclease-dead C2c1 protein or the guide RNA is as described above. Selection of the transcriptional repressor protein is within the skill of those ordinary people in the art.

As used herein, gene suppression or silencing refers to the down-regulation or elimination of gene expression, preferably at the transcriptional level.

However, the gene expression regulatory system of the present invention can also use a fusion protein of a nuclease-dead C2c1 protein and a transcriptional activator protein. In this case, the gene expression regulatory system is a gene expression activation system. For example, the gene expression activation system of the present invention may comprise one of the following:
  i) a fusion protein of a nuclease-dead C2c1 protein and a transcriptional activator protein, and a guide RNA;
  ii) an expression construct comprising a nucleotide sequence encoding a fusion protein of a nuclease-dead C2c1 protein and a transcriptional activator protein, and a guide RNA;
  iii) a fusion protein of a nuclease-dead C2c1 protein and a transcriptional activator protein, and an expression construct comprising a nucleotide sequence encoding a guide RNA;
  iv) an expression construct comprising a nucleotide sequence encoding a fusion protein of a nuclease-dead C2c1 protein and a transcriptional activator protein, and an expression construct comprising a nucleotide sequence encoding a guide RNA; or
  v) an expression construct comprising a nucleotide sequence encoding a fusion protein of a nuclease-dead C2c1 protein and a transcriptional activator protein and a nucleotide sequence encoding a guide RNA.

The definition of the nuclease-dead C2c1 protein or the guide RNA is as described above. Selection of the transcriptional activator protein is within the skill of those ordinary people in the art.

As used herein, gene activation refers to up-regulation of gene expression levels, preferably at the transcriptional level.

In another aspect, the invention also encompasses the use of the genome editing system of the invention in the treatment of diseases.

By modifying a disease-related gene by the genome editing system of the present invention, it is possible to achieve up-regulation, down-regulation, inactivation, activation, or mutation correction of the disease-related gene, thereby achieving prevention and/or treatment of the disease. For example, in the present invention, the target sequence may be located in the protein coding region of the disease-related gene, or may be, for example, located in a gene expression regulatory region such as a promoter region or an enhancer region, thereby enabling functional modification of the disease-related gene or modification of the expression of the disease-related gene.

A "disease-related" gene refers to any gene that produces a transcriptional or translational product at an abnormal level or in an abnormal form in a cell derived from a disease-affected tissue as compared to a tissue or cell of non-disease control. When altered expression is related with the appearance and/or progression of a disease, it may be a gene that is expressed at an abnormally high level or it may be a gene that is expressed at an abnormally low level. A disease-related gene also refers to a gene having one or more mutations or a genetic variation that is directly responsible for or has genetic linkage with one or more genes responsible for the etiology of the disease. The transcribed or translated product may be known or unknown and may be at normal or abnormal levels.

Accordingly, in another aspect, the invention also provides a method of treating a disease in a subject in need thereof, comprising delivering to the subject an effective amount of a genome editing system of the invention to modify a gene related to the disease.

In another aspect, the invention also provides the use of a genome editing system of the invention for the preparation of a pharmaceutical composition for treating a disease in a subject in need thereof, wherein the genome editing system is for modifying a gene related to the disease.

In another aspect, the invention also provides a pharmaceutical composition for treating a disease in a subject in need thereof, comprising a genome editing system of the invention and a pharmaceutically acceptable carrier, wherein the genome editing system is for modifying a gene related to the disease.

In some embodiments, the subject is a mammal, such as a human.

Examples of such diseases include, but are not limited to, tumors, inflammation, Parkinson's disease, cardiovascular disease, Alzheimer's disease, autism, drug addiction, age-related macular degeneration, schizophrenia, hereditary diseases, and the like.

In another aspect, the invention also includes a kit for use in the methods of the invention, the kit comprising the genome editing system of the invention, and an instruction. The kits generally include a label indicating the intended use and/or method of use of the contents in the kit. The term label includes any written or recorded material provided on or with the kit or otherwise provided with the kit.

EXAMPLE

Materials and Methods
DNA Manipulations

DNA manipulations including DNA preparation, digestion, ligation, amplification, purification, agarose gel electrophoresis, etc. were conducted according to *Molecular Cloning: A Laboratory Manual* with some modifications.

Briefly, PAM sequence determination plasmids were constructed by ligating annealed oligonucleotides (oligos) (Table 1) between digested EcoRI and SphI sites in p11-LacY-wtx1, and corresponding dsDNA fragments carrying different PAM sequences were PCR generated.

Targeting sgRNAs for cell transfection assay were constructed by ligating annealed oligos into BasI-digested pUC19-U6-sgRNA vectors.

Templates for sgRNA in vitro transcription were PCR amplified using primers containing a T7 promoter sequence.
De Novo Gene Synthesis and Plasmid Construction.

New type V-B CRISPR-C2c1 protein coding sequences identified by PSI-BLAST program were humanized (codon optimized) and full-length synthesized. pCAG-2AeGFP vector and BPK2014-ccdB vector were applied for C2c1 mammalian cell expression and *E. coli* expression, respectively. Guide RNAs were constructed in a pUC19-U6 vector for mammalian cell expression.
Protein Purification The synthetic C2c1 coding sequences were constructed into a BPK2014-ccdB expression vector using ligation-dependent cloning. The resulting fusion construct containing a C-terminal fused $His_{10}$ tag. The proteins were expressed in *E. coli* strain BL21 (λ DE3) (Transgen Biotech), grown in $Cm^R$+LB medium at 37° C. to $OD_{600}$~0.4, following induction with 0.5 mM IPTG at 16° C. for 16 h. 300 mL induced cells were harvested for protein purification and all subsequent steps were conducted at 4° C. Cell pellets were lysed in 30 mL Lysis Buffer (NPI-10: 50 mM $NaH_2PO_4$, 300 mM NaCl, 10 mM imidazole, 5% glycerol, pH8.0) supplemented with 1× protease inhibitors (Roche complete, EDTA-free) before lysis by sonication. Lysates were clarified by centrifugation of 8,000 rpm at 4° C. for 10 min, and the supernatants incubated with His60 Ni Superflow Resin (Takara) in batches at 4° C. for 2 h. After the resin extremely washed with each 20 mL Wash Buffer 1 (NPI-20: 50 mM $NaH_2PO_4$, 300 mM NaCl, 20 mM imidazole, 5% glycerol, pH8.0), Wash Buffer 2 (NPI-40: 50 mM $NaH_2PO_4$, 300 mM NaCl, 40 mM imidazole, 5% glycerol, pH8.0) and Wash Buffer 3 (NPI-100: 50 mM $NaH_2PO_4$, 300 mM NaCl, 100 mM imidazole, 5% glycerol, pH8.0), expressed proteins were eluted with 5 mL Elution Buffer (NPI-300: 50 mM $NaH_2PO_4$, 300 mM NaCl, 300 mM imidazole, 5% glycerol, pH8.0). Purified C2c1 proteins were dialyzed using 100 kDa dialyzer overnight with Storage Buffer (Tris-HCl, pH8.0, 200 mM KCl, 0.1 mM EDTA pH8.0, 1 mM DTT, 20% glycerol). Fractions were pooled and concentrated with 100 kDa Centrifugal Filter Unit (Millipore). The purity of enriched proteins was analyzed by SDS-PAGE and Coomassie staining and the concentration quantitated using BCA Protein Assay Kit (Thermo Fisher).
In Vitro RNA Transcription RNAs were in vitro transcribed using HiSribe™ T7 Quick High Yield RNA Synthesis Kit (NEB) and PCR-amplified DNA templates carrying a T7 promoter sequence. Transcribed RNAs were purified using Oligo Clean & Concentrator™ (ZYMO Research) and quantitated on NanoDrop™ 2000 (Thermo Fisher).
In Vitro PAM Sequence Determination.

To determine the PAM sequence of AaC2c1, 100 nM AaC2c1 protein, 400 ng in vitro transcribed sgRNA and 200 ng PCR-generated double stranded DNA (dsDNA) bearing different PAM sequences (Table 1) were incubated at 37° C. for 1 h in cleavage buffer (50 mM Tris-HCl, 100 mM NaCl, 10 mM $MgCl_2$, pH8.0). The reactions were stopped by adding RNase A to digest sgRNA at 37° C. for 20 min and following inactivation of RNase A at 75° C. for 5 min, and resolved by ~3% agarose gel electrophoresis and ethidium bromide staining.
dsDNA Cleavage Assay For dsDNA cleavage assay, 100 nM C2c1 protein, 400 ng in vitro transcribed sgRNA and 200 ng PCR-generated double stranded DNA (dsDNA) containing a 5'TTTN-PAM sequence were incubated at 37° C. for 1 h in cleavage buffer (50 mM Tris-HCl, 100 mM NaCl, 10 mM $MgCl_2$, pH8.0) if not specified.

To determine the thermal stability of AaC2c1, the cleavage reactions were performed at a large range of temperatures (4° C.-100° C.) for 1 h in cleavage buffer (50 mM Tris-HCl, 100 mM NaCl, 10 mM $MgCl_2$, pH8.0).

For pH tolerance assay, the cleavage reactions were performed at 37° C. for 1 h in cleavage buffer (50 mM Tris-HCl, 100 mM NaCl, 10 mM $MgCl_2$) with pH ranging from 1.0 to 13.0.

In $Mg^{2+}$-dependent assay, cleavage buffer (50 mM Tris-HCl, 100 mM NaCl, pH8.0) was supplemented with EDTA (0 mM, 1 mM, 5 mM, 10 mM, 20 mN and 40 mM) or $Mg^{2+}$ (0 mM, 1 mM, 5 mM, 10 mM, 20 mN and 40 mM) and the mixtures were incubated at 37° C. for 1 h.

Further metal-dependent cleavage reactions were conducted at 37° C. for 1 h in cleavage buffers (50 mM Tris-HCl, 100 mM NaCl, 10 mM $MgCl_2$, 1 mM EDTA, pH8.0) supplemented with 1 or 5 mM of $CaCl_2$), $MnCl_2$, $SrCl_2$, $NiCl_2$, $FeCl_2$, $CoCl_2$, $ZnCl_2$ or $CuCl_2$. The reactions were stopped by adding RNase A to digest sgRNA at 37° C. for 20 min and following inactivation of RNase A at 75° C.

for 5 min, and resolved by ~3% agarose gel electrophoresis and ethidium bromide staining.

Cell culture, transfection and fluorescence-activated cell sorting (FACS) Human embryonic kidney (HEK) cell line HK293T was maintained in Dulbecco's modified Eagle's Medium (DMEM) supplemented with 10% fetal bovine serum and 1% Antibiotic-Antimycotic (Gibco) at 37° C. with 5% C02 incubation. Mouse epiblast stem cell (EpiSC) line was maintained on fibronectin in N2B27 medium with activin A (20 ng/ml, R&D) and FGF2 (12.5 ng/ml, R&D). HK293T or EpiSC cells were seeded into 24-well plates (Corning) one day prior to transfection. Cells were transfected using Lipofectamine LTX (Invitrogen) following the manufacturer's recommended protocol. For each well of a 24-well plate, a total of 750 ng plasmids were used. Then 48 h following transfection, GFP-positive cells were sorted using the MoFlo XDP (Beckman Coulter).

T7 Endonuclease I (T7EI) Assay and Sequencing Analysis for Genome Modification

Harvested or FACS-sorted GFP-positive HK293T or EpiSC cells post transfection with plasmid DNA for 48 h were subjected to genomic DNA extraction. Briefly, cells were direct lysed with Buffer L (Bimake) and incubated at 55° C. for 3 h and 95° C. for 10 min. Genomic region surrounding the CRISPR-C2c1 target site for each gene was PCR amplified. 200-400 ng PCR products were mixed with ddH$_2$O to a final volume of 10 μL, and subjected to re-annealing process to enable heteroduplex formation according to previous methods. After re-annealing, products were treated with 1/10 volume of NEBuffer™ 2.1 and 0.2 μL T7EI (NEB) at 37° C. for 30 min, and analyzed on 3% agarose gels. Indel was quantitated based on relative band intensities.

T7EI assay identified mutated products were cloned into TA-cloning vector pEASY®-T1 (Transgen Biotech) and transformed to competent *E. coli* strain Transl-T1 (Transgen Biotech). After overnight culture, colonies were randomly picked out and sequenced.

Off-Target Prediction and Detection

Since type V-B CRISPR-C2c1 system has not been harnessed to edit mammalian genomes, there is no guideline to predict off-targets. Primary data in FIG. 7 provide some reference that the seed region might be the first 17 nucleotide (nt) on the 5' end of the spacer sequence, because minimal off-target cleavage activity was detected when the spacer was truncated to 18 nt. Since the 7$^{th}$ mismatch on the 5' end of the spacer sequence can tolerate off-target, the human genome was searched with the 14 nt seed sequence on the 5' end containing a 5'TTN-PAM sequence. One mismatch or two discontinuous mismatches of the 14 nt seed sequence were still included. T7EI assay was applied to confirm whether the off-targets existed.

Site-Directed C2c1 Gene Mutagenesis

Two pairs of primers containing the desired site-directed mutation and 5' end overlaps were used for gene amplification. The two agarose gel-purified gene fragments were assembled into XmaI and NheI double-digested mammalian expression vector using NEBuilder™ HiFi DNA Assembly Master Mix (NEB) following the manufacture's recommended protocol. And *E. coli* expression vectors were reconstructed using digestion- and ligation-dependent methods.

Example 1. In Vitro Analysis of AaC2c1 Nuclease Activity

Firstly, the PAM sequence of C2c1 from *A. acidiphilus* of the present invention was identified by in vitro nucleic acid cleavage. FIG. 1A shows cleavage using AaC2c1 and sgRNA targeting locus bearing various PAMs. Symbol "+" below the figure indicates robust cleavage activity in vitro. The result show that the PAM of AaC2c1 can be 5'TTTN-, 5'ATTN-, 5'GTTN-, 5'CTTN-, 5'TTC-, 5'TTG-, 5'TTA-, 5'TTT-, 5'TAN-, 5'TGN-, 5'TCN-, 5'ATC-.

Figure 1B:
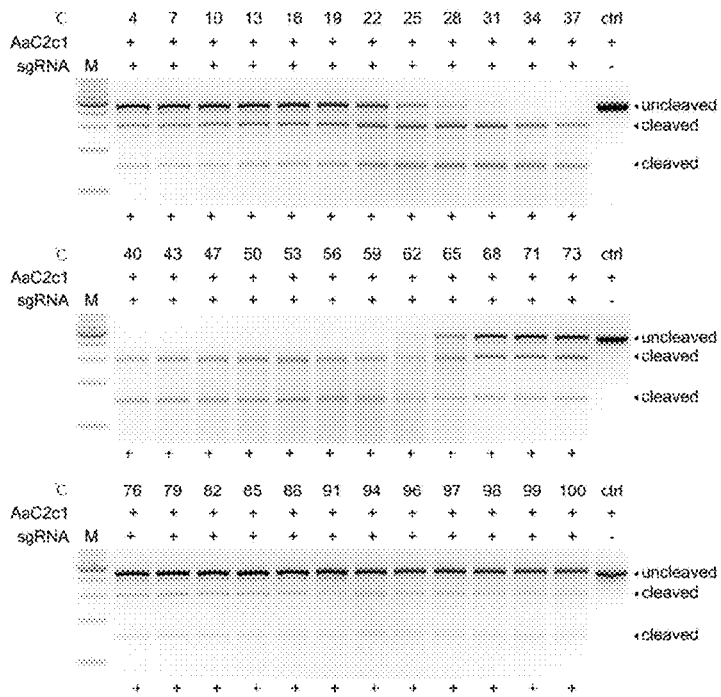
Figure 1C:
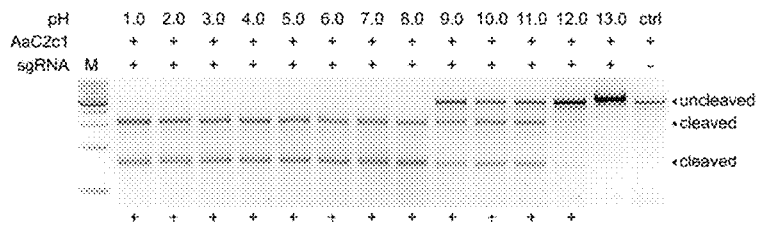

Secondly, the temperature and acid-base tolerance of AaC2c1 were tested. FIG. 1B shows cleavage activity of AaC2c1 at a broad temperature window (4° C.-100° C.). FIG. 1C shows analysis of AaC2c1 cleavage activity at a wide-range pH values (pH1.0-pH13.0). The results show that AaC2c1 can work at 4° C.-100° C., and the cutting efficiency is higher at about 30° C.-60° C. AaC2c1 works at pH 1.0-pH 12.0 and has a higher cutting efficiency at pH 1.0-pH 8.0.

FIG. 2A shows a map of bacterial genomic locus of C2c1 from *A. acidiphilus* identified in the present application. Since the genomic locus of *A. acidiphilus* containing C2c1 gene has no direct repeat (DR) array sequenced, this study adopts a hypothetical crRNA from reported *A. acidoterrestris*.

FIG. 2B shows stepwise purification of *E. coli* expressed AaC2c1-His$_{10}$ used in this Example.

FIG. 2C shows cleavage sites of the cleavage products from FIG. 1A as determined by Sanger sequencing.

FIG. 2D shows in vitro AaC2c1 cleavage assay in the presence of different concentrations of EDTA and Mg$^{2+}$, indicating that AaC2c1 is a Mg$^{2+}$-dependent endonuclease.

FIG. 2E shows DNA cleavage assay conducted by AaC2c1 in the presence of selected metals, Ca$^{2+}$, Mn$^{2+}$, Sr$^{2+}$, Ni$^{2+}$, Fe$^{2+}$, Co$^{2+}$, Zn$^{2+}$, Cu$^{2+}$. Symbol "+" below the figure indicates robust cleavage activity in vitro.

TABLE 1

Target sequences bearing various 5'PAM sequences used for in vitro DNA cleavage assay. Target sequences used for in vitro DNA cleavage analysis of PAM sequences were commercial synthesized (BGI) with EcoRI 5' and SphI 3' overhangs highlighted with underlines and boxes, respectively. Annealed oligos were constructed into EcoRI and SphI double-digested p11-LacY-wtx1 vector.

| ID | Target sequence (5'-3') | 5' PAM |
|---|---|---|
| p11-Nr1-1 | aattagTTTCCCTCCCAGTCCCTTGGCTAT catg ATAGCCAAGGGACTGGGAGGGAAAct (SEQ ID NO: 28) | TTTC (SEQ ID NO: 29) |
| p11-Nr1-2 | aattaaTTCCCTCCCAGTCCCTTGGCTAT catg ATAGCCAAGGGACTGGGAGGGAAtt (SEQ ID NO: 30) | ATTC (SEQ ID NO: 31) |

TABLE 1-continued

Target sequences bearing various 5'PAM sequences used for in vitro DNA cleavage assay. Target sequences used for in vitro DNA cleavage analysis of PAM sequences were commercial synthesized (BGI) with EcoRI 5' and SphI 3' overhangs highlighted with underlines and boxes, respectively. Annealed oligos were constructed into EcoRI and SphI double-digested p11-LacY-wtx1 vector.

| ID | Target sequence (5'-3') | 5' PAM |
|---|---|---|
| p11-Nr1-3 | aattagTTCCCTCCCAGTCCCTTGGCTAT catg<br>ATAGCCAAGGGACTGGGAGGGAAct (SEQ ID NO: 302) | GTTC<br>(SEQ ID NO: 33) |
| p11-Nr1-4 | aattacTTCCCTCCCAGTCCCTTGGCTAT catg<br>ATAGCCAAGGGACTGGGAGGGAAgt (SEQ ID NO: 34) | CTTC<br>(SEQ ID NO: 35) |
| p11-Nr1-5 | aattgTTCCCTCCCAGTCCCTTGGCTAT catg<br>ATAGCCAAGGGACTGGGAGGGAAc (SEQ ID NO: 36) | TTC<br>(SEQ ID NO: 37) |
| p11-Nr1-6 | aattaTaCCCTCCCAGTCCCTTGGCTAT catg<br>ATAGCCAAGGGACTGGGAGGGtAt (SEQ ID NO: 38) | TAC<br>(SEQ ID NO: 39) |
| p11-Nr1-7 | aattaTgCCCTCCCAGTCCCTTGGCTAT catg<br>ATAGCCAAGGGACTGGGAGGGcAt (SEQ ID NO: 40) | TGC<br>(SEQ ID NO: 41) |
| p11-Nr1-8 | aattaTcCCCTCCCAGTCCCTTGGCTAT catg<br>ATAGCCAAGGGACTGGGAGGGgAt (SEQ ID NO: 42) | TCC<br>(SEQ ID NO: 43) |
| p11-Nr1-9 | aattaaTCCCTCCCAGTCCCTTGGCTAT catg<br>ATAGCCAAGGGACTGGGAGGGAtt (SEQ ID NO: 44) | ATC<br>(SEQ ID NO: 45) |
| p11-Nr1-10 | aattagTCCCTCCCAGTCCCTTGGCTAT catg<br>ATAGCCAAGGGACTGGGAGGGAct (SEQ ID NO: 46) | GTC<br>(SEQ ID NO: 47) |
| p11-Nr1-11 | aattacTCCCTCCCAGTCCCTTGGCTAT catg<br>ATAGCCAAGGGACTGGGAGGGAgt (SEQ ID NO: 48) | CTC<br>(SEQ ID NO: 49) |
| p11-Nr1-12 | aattaaaCCCTCCCAGTCCCTTGGCTAT catg<br>ATAGCCAAGGGACTGGGAGGGttt (SEQ ID NO: 50) | AAC<br>(SEQ ID NO: 51) |
| p11-Nr1-13 | aattaggCCCTCCCAGTCCCTTGGCTATcatg<br>ATAGCCAAGGGACTGGGAGGGcct (SEQ ID NO: 52) | GGC<br>(SEQ ID NO: 53) |
| p11-Nr1-14 | aattaccCCCTCCCAGTCCCTTGGCTAT catg<br>ATAGCCAAGGGACTGGGAGGGggt (SEQ ID NO: 54) | CCC<br>(SEQ ID NO: 55) |
| p11-Nr1-15 | aattaTTgCCTCCCAGTCCCTTGGCTAT catg<br>ATAGCCAAGGGACTGGGAGGcAAt (SEQ ID NO: 56) | TTG<br>(SEQ ID NO: 57) |
| p11-Nr1-16 | aattaTTaCCTCCCAGTCCCTTGGCTAT catg<br>ATAGCCAAGGGACTGGGAGGtAAt (SEQ ID NO: 58) | TTA<br>(SEQ ID NO: 59) |
| p11-Nr1-17 | aattaTTtCCTCCCAGTCCCTTGGCTAT catg<br>ATAGCCAAGGGACTGGGAGGaAAt (SEQ ID NO: 60) | TTT<br>(SEQ ID NO: 61) |

Example 2. Genome Editing Activity of AaC2c1 in Mammalian Cells

This example detects genome editing activity of AaC2c1 in mammalian cells. The target sequences used are shown in Table 3 below.

FIG. 3A is schematic of the AaC2c1 sgRNA-DNA-targeting complex.

FIG. 3B shows T7EI analysis of indels produced at the human RNF2 targeting sites. Numbers as shown under the lanes with mutation indicate the indel rate. Triangles indicate cleavage fragments.

FIG. 3C shows Sanger sequencing of cleavage products from FIG. 3B. Red letters highlights the PAM sequence.

T7EI assay shows that AaC2c1 induces indels at the mouse Nrl locus (FIG. 3D). FIG. 3E shows the sequences of targeted alleles caused by cleavage at the Nrl gene targeting site 1 from FIG. 3D.

Therefore, AaC2c1 can mediate robust genome editing in mammalian cells. Data in FIG. 4 further prove this conclusion. FIG. 4A shows that in T7EI analysis, AaC2c1 induced indels at mouse Apob gene locus. Triangles indicate cleavage fragments. FIG. 4B shows corresponding Sanger sequencing results. FIG. 4C shows genome targeting on human CD34 gene by AaC2c1 using T7EI assay. FIG. 4D shows corresponding Sanger sequencing results. FIG. 4E shows additional targets of human endogenous RNF2 gene targeted by AaC2c1. FIG. 4F shows corresponding Sanger sequencing results. FIG. 4G shows additional targets of human endogenous RNF2 gene targeted by AaC2c1. FIG. 4H shows corresponding Sanger sequencing results.

TABLE 2

Primers sequences for target gene amplification and T7EI assay.

| Primer Name | Primer sequences (5' - 3') | Product length (bp) |
|---|---|---|
| RNF2-F<br>RNF2-R | GGAGCTGTAGGCGATTATAGTTGAA<br>(SEQ ID NO: 62)<br>TTCTCAAACCCTGGAAAGCACTTT<br>(SEQ ID NO: 63) | 403 |
| CD34-F<br>CD34-R | TTGAAATGAGTTTGGTCAGGGATGG<br>(SEQ ID NO: 64)<br>AACTGTGTATTTCCGTGCTGATTCC<br>(SEQ ID NO: 65) | 550 |
| Nrl-F<br>Nrl-R | GCCTCTCAGTGTTCTACACCTTCC<br>(SEQ ID NO: 66)<br>CCATAGAGACAGGACCCTGGTTCT<br>(SEQ ID NO: 67) | 386 |
| Apob-F<br>Apob-R | CGTGCCCTTTGGACCTTTGG<br>(SEQ ID NO: 68)<br>GGAGCCCTCACAACCTAAATTATCT<br>(SEQ ID NO: 69) | 575 |

TABLE 3

Protospacer sequences of mammalian genomic targets.

| Target species | Gene | Protospacer ID | Protospacer sequence 5' (5'-3')  PAM | Strand | Cell line tested |
|---|---|---|---|---|---|
| Homo sapiens | RNF2 | 1 | TGGAAACACAAACTCTTCTGTTTA<br>(SEQ ID NO: 70)   (SEQ ID NO: 71) | + | HK293T |
| | | 2 | AGACCTTTCAACCACTAGCATTTC<br>(SEQ ID NO: 72)   (SEQ ID NO: 73) | + | HK293T |
| | | 3 | AACTCCAGAGACAACCTTGATTTC<br>(SEQ ID NO: 74)   (SEQ ID NO: 75) | + | HK293T |
| | | 4 | AACCACTAGCACTAGCCTTGTTTC<br>(SEQ ID NO: 76)   (SEQ ID NO: 77) | + | HK293T |
| | | 5 | CATAAACTGAGGTTATCACATTTC<br>(SEQ ID NO: 78)   (SEQ ID NO: 79) | − | HK293T |
| | | 6 | TGTTTCCATAAACTGAGGTTTTTG<br>(SEQ ID NO: 80)   (SEQ ID NO: 81) | − | HK293T |
| | | 7 | CAGGTGACAGGCTAGGCTTCTTTC<br>(SEQ ID NO: 82)   (SEQ ID NO: 83) | − | HK293T |
| | | 8 | GTGGGAGATGTTGCAAGGCTTTTA<br>(SEQ ID NO: 84)   (SEQ ID NO: 85) | − | HK293T |
| | | 9 | ACATCTACCTCTGTGATAACTTC<br>(SEQ ID NO: 86)   (SEQ ID NO: 87) | + | HK293T |
| | | 10 | ATGGAAACACAAACTCTTCTTTT<br>(SEQ ID NO: 88)   (SEQ ID NO: 89) | + | HK293T |
| | | 11 | TGTCCAGTCACAGACCTCTGTTTC<br>(SEQ ID NO: 90)   (SEQ ID NO: 91) | + | HK293T |
| | | 12 | ACCACCCCAGCCAACGTTTCTTC<br>(SEQ ID NO: 92)   (SEQ ID NO: 93) | + | HK293T |
| | | 13 | AAGCCTAGCCTGTCACCTGGTTG<br>(SEQ ID NO: 94)   (SEQ ID NO: 95) | + | HK293T |
| | | 14 | CAGACCTTTCAACCACTAGCTTT<br>(SEQ ID NO: 96)   (SEQ ID NO: 97) | + | HK293T |
| | | 15 | CAACATCTCCCACTAAACCCTTG<br>(SEQ ID NO: 98)   (SEQ ID NO: 99) | + | HK293T |
| | | 16 | TCCTATCCTAAGTGACATCATTC<br>(SEQ ID NO: 100)   (SEQ ID NO: 101) | + | HK293T |
| Homo sapiens | CD34 | 1 | ACCTCGAAGTCTACACAGTGTTTC<br>(SEQ ID NO: 102)   (SEQ ID NO: 103) | + | HK293T |
| | | 2 | TTTGGATATGTTGAAGAACATTTG<br>(SEQ ID NO: 104)   (SEQ ID NO: 105) | + | HK293T |
| | | 3 | GATATGTTGAAGAACACCATTTTG<br>(SEQ ID NO: 106)   (SEQ ID NO: 107) | + | HK293T |
| | | 4 | CATCGTTTTTGTGCAGACTGTTTA<br>(SEQ ID NO: 108)   (SEQ ID NO: 109) | + | HK293T |
| | | 5 | GTGCAGACTGCATCATCACATTTT<br>(SEQ ID NO: 110)   (SEQ ID NO: 111) | + | HK293T |
| | | 6 | TGCAGACTGCATCATCACAGTTTG<br>(SEQ ID NO: 112)   (SEQ ID NO: 113) | + | HK293T |
| | | 7 | AGGCAATAACAGATGGCTTATTTC<br>(SEQ ID NO: 114)   (SEQ ID NO: 115) | − | HK293T |
| | | 8 | GTTGAAGAACACCATGACTATTTG<br>(SEQ ID NO: 116)   (SEQ ID NO: 117) | − | HK293T |

TABLE 3-continued

Protospacer sequences of mammalian genomic targets.

| Target species | Gene | Protospacer ID | Protospacer sequence 5' (5'-3') PAM | Strand | Cell line tested |
|---|---|---|---|---|---|
| | | 9 | GAAATTGTGGTTTCACCTCGTTA (SEQ ID NO: 118) (SEQ ID NO: 119) | + | HK293T |
| | | 10 | TGGTTTCACCTCGAAGTCTATTG (SEQ ID NO: 120) (SEQ ID NO: 121) | + | HK293T |
| | | 11 | CACCTCGAAGTCTACACAGTTTT (SEQ ID NO: 122) (SEQ ID NO: 123) | + | HK293T |
| | | 12 | ATGTGCCCAATTTGTTTGGATTA (SEQ ID NO: 124) (SEQ ID NO: 125) | + | HK293T |
| | | 13 | GGATATGTTGAAGAACACCATTT (SEQ ID NO: 126) (SEQ ID NO: 127) | + | HK293T |
| | | 14 | TTGTGCAGACTGCATCATCATTT (SEQ ID NO: 128) (SEQ ID NO: 129) | + | HK293T |
| | | 15 | AAGAACACCATGACTACAAATTG (SEQ ID NO: 130) (SEQ ID NO: 131) | + | HK293T |
| | | 16 | GAAGTGGGTATGTTGAAAAGTTA (SEQ ID NO: 132) (SEQ ID NO: 133) | + | HK293T |
| Mus musculus | Nrl | 1 | CCTCCCAGTCCCTTGGCTATTTTC (SEQ ID NO: 134) (SEQ ID NO: 135) | + | EpiSC |
| | | 2 | ATTTGATGAAGTTCGAAATATTTG (SEQ ID NO: 136) (SEQ ID NO: 137) | + | EpiSC |
| | | 3 | ATGAAGTTCGAAATAAAGCGTTTG (SEQ ID NO: 138) (SEQ ID NO: 139) | + | EpiSC |
| | | 4 | GAACTTCATCAAATCAAAGTTTTC (SEQ ID NO: 140) (SEQ ID NO: 141) | − | EpiSC |
| | | 5 | TTTCGAACTTCATCAAATCATTTA (SEQ ID NO: 142) (SEQ ID NO: 143) | − | EpiSC |
| | | 6 | TGAGGGCCGATCTGGAGTCCTTC (SEQ ID NO: 144) (SEQ ID NO: 145) | + | EpiSC |
| | | 7 | GGCTCCACACCATACAGCTCTTG (SEQ ID NO: 146) (SEQ ID NO: 147) | + | EpiSC |
| | | 8 | ATCAAATCAAAGTCATTAACTTC (SEQ ID NO: 148) (SEQ ID NO: 149) | − | EpiSC |
| Mus musculus | Apob | 1 | TAGGAGGAGCTGGCTTAAGGTTTA (SEQ ID NO: 150) (SEQ ID NO: 151) | + | EpiSC |
| | | 2 | AAAAGTGCTCCATTTATAGGTTTG (SEQ ID NO: 152) (SEQ ID NO: 153) | + | EpiSC |
| | | 3 | CTGGCTGTGGCCTGGCCACGTTC (SEQ ID NO: 154) (SEQ ID NO: 155) | + | EpiSC |
| | | 4 | GTGGGCCCATGGCGGATGATTTC (SEQ ID NO: 156) (SEQ ID NO: 157) | + | EpiSC |
| | | 5 | CACCCTAACTCACGAGCCCATTC (SEQ ID NO: 158) (SEQ ID NO: 159) | + | EpiSC |
| | | 6 | TCCCAGGCTTCCACCCTAACTTTC (SEQ ID NO: 160) (SEQ ID NO: 161) | + | EpiSC |
| | | 7 | TACCCCAGGATGTAACTGGTTTTC (SEQ ID NO: 162) (SEQ ID NO: 163) | + | EpiSC |
| | | 8 | ATCACCCCCGCCCCTCCCTTTC (SEQ ID NO: 164) (SEQ ID NO: 165) | + | EpiSC |

Example 3. Optimization of sgRNA

This example optimizes the single guide RNA (sgRNA) that directs the AaC2c1 for genome editing. The original sgRNA is sgRNA1 constructed based on the tracrRNA in the AaC2c1 locus and the putative crRNA of *A. acidoterrestris*.

Figure 5A:
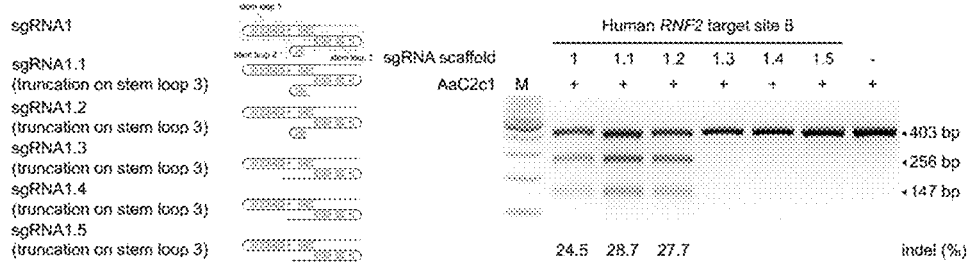
Figures 6A, 6B, 6C:
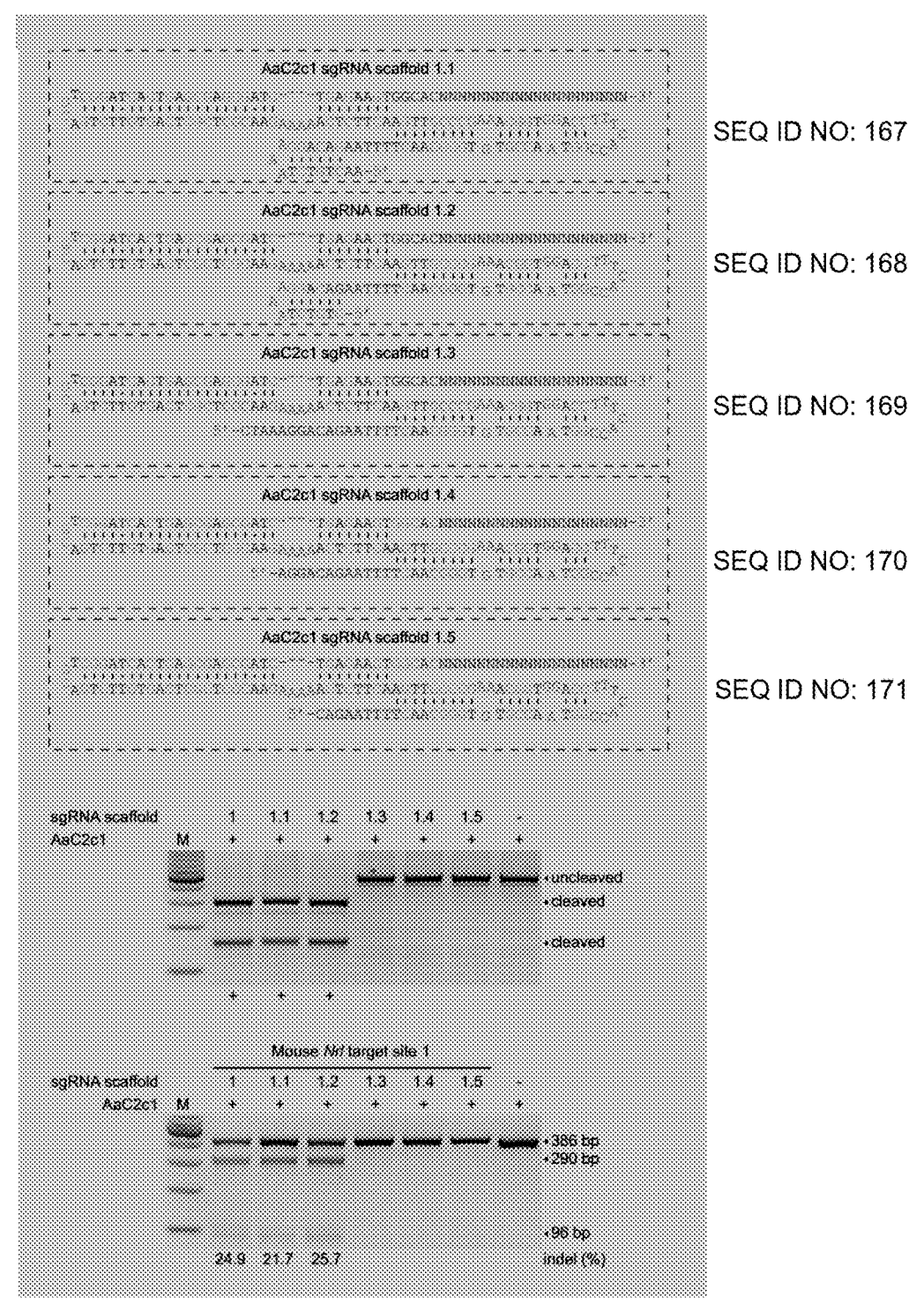

FIG. 6A shows the different versions of the sgRNA scaffold sequence structure with 5' truncation at stem loop 3 of sgRNA1. FIG. 5A shows truncation and disruption of stem loop 3 of sgRNA abolishes AaC2c1 targeting activity to human endogenous gene RNF2 targeting site 8. FIG. 6B shows truncation and disruption of stem loop 3 of sgRNA abolishes AaC2c1 targeting activity in vivo. FIG. 6C shows truncation and disruption of stem loop 3 of sgRNA abolishes AaC2c1 targeting activity to mouse endogenous gene Nrl targeting site 1.

Figure 5B:
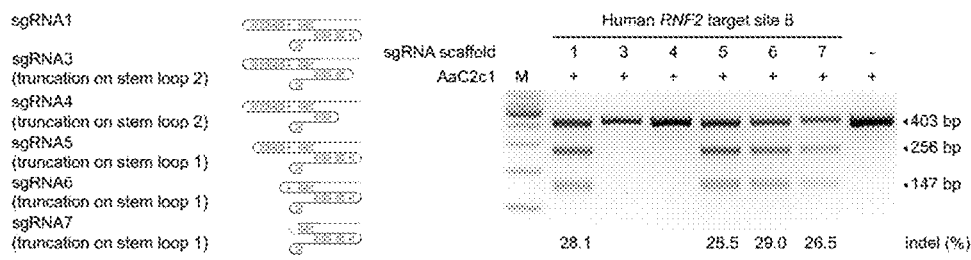
Figure 5C:
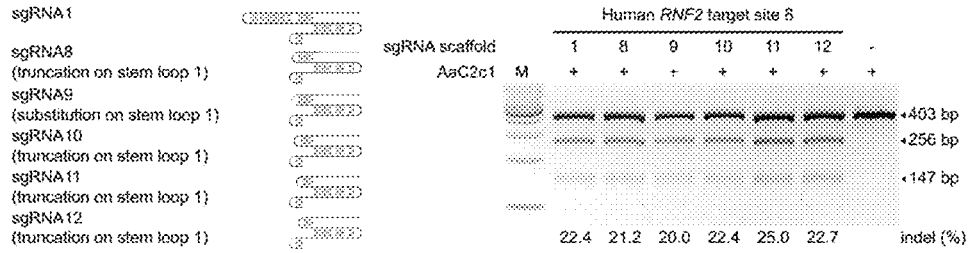

FIG. 6D shows the different versions of the sgRNA scaffold sequence structure truncated and optimized for stem loops 2 and 1 of sgRNA1. FIG. 5B shows truncation of stem loop 2 of sgRNA disrupts AaC2c1 activity in vivo, while truncation of stem loop 1 reserves AaC2c1 endonuclease activity. FIG. 5C shows further optimization of AaC2c1 sgRNA on stem loop 1 and function validation in vivo. FIGS. 6E and F show similar results obtained from the corresponding in vitro and mouse experiments.

Figure 5D:
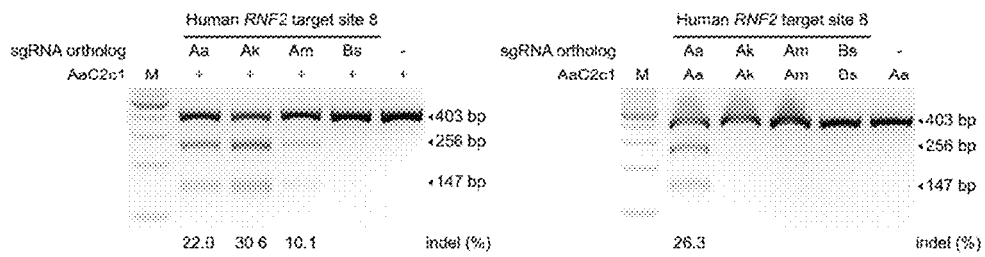
Figure 5E:
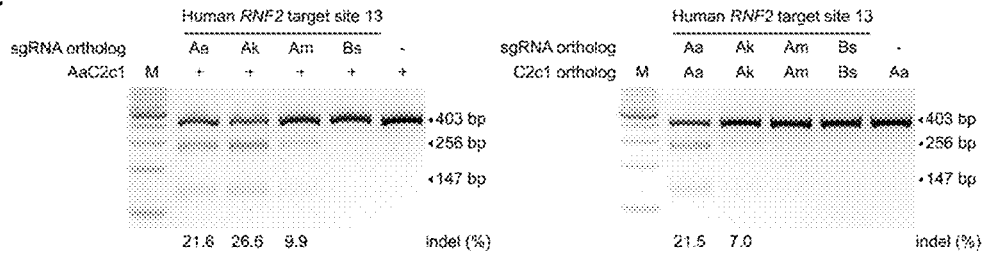

FIGS. 5D and E show AaC2c1 with different orthologous sgRNAs (FIG. 6G) targets endogenous human RNF2 gene. T7EI assay indicates AaC2c1 can perform function in vivo with sgRNA derived from *A. acidiphilus, A. kakegawensis* and *A. macrosporangiidus*. The right panel of FIG. 5E shows the AkC2c1 protein derived from *A. kakegawensis* also enables genome editing in mammalian cells. FIGS. 6J-M show the results obtained from the corresponding in vitro and mouse experiments.

FIG. 6H and 6I show evolutionary relationship of the four bacterial stains, *Alicyclobacillus acidiphilus* (NBRC 100859), *Alicyclobacillus kakegawensis* (NBRC 103104), *Alicyclobacillus macrosporangiidus* (strain DSM 17980), *Bacillus* sp. (NSP2.1), based on their sgRNA sequences and C2c1 proteins sequences.

TABLE 4

Sequences for AaC2c1 single guide RNA (sgRNA) optimization. Single chimeric guide RNA (sgRNA) from *Alicyclobacillus acidiphilus* type V-B CRISPR locus were engineered. The italics and bold font highlighted the tracrRNA and the crRNA sequences, respectively. The continuous N at 3'-end represented 20 nt protospacer sequence (target sequence). Since no direct repeat (DR) array contained in *A. acidiphilus* CRISPR locus, we adopted the crRNA sequence from orthologous *Alicyclobacillus acidoterrestris* type V-B CRISPR locus and engineered with tracrRNA from *A. acidiphilus* type V-B CRISPR locus. Sequences of optimized sgRNAs from original sgRNA1 were listed. N is independently selected from A, T, G, C.

| sgRNA name | sgRNA sequences (5'- 3') |
|---|---|
| sgRNA1 | *GTCTAAAGGACAGAATTTTTCAACGGGTGTGCCAATGGCCACTTTCCAGGTGGCAAAGCC CGTTGAACTTCTCAAAAAGAACGCTCGCTCAGTGTTCTGAC*GTCGGATCACTGAGCGAGC GATCTGAGAAGTGGCACNNNNNNNNNNNNNNNNNNNN (SEQ ID NO: 166) |
| sgRNA1.1 | *AACTGTCTAAAGGACAGAATTTTTCAACGGGTGTGCCAATGGCCACTTTCCAGGTGGCAA AGCCCGTTGAACTTCTCAAAAAGAACGCTCGCTCAGTGTTCTGAC*GTCGGATCACTGAGC GAGCGATCTGAGAAGTGGCACNNNNNNNNNNNNNNNNNNNN (SEQ ID NO: 167) |
| sgRNA1.2 | *CTGTCTAAAGGACAGAATTTTTCAACGGGTGTGCCAATGGCCACTTTCCAGGTGGCAAAG CCCGTTGAACTTCTCAAAAAGAACGCTCGCTCAGTGTTCTGAC*GTCGGATCACTGAGCGA GCGATCTGAGAAGTGGCACNNNNNNNNNNNNNNNNNNNN (SEQ ID NO: 168) |
| sgRNA1.3 | *CTAAAGGACAGAATTTTTCAACGGGTGTGCCAATGGCCACTTTCCAGGTGGCAAAGCCCG TTGAACTTCTCAAAAAGAACGCTCGCTCAGTGTTCTGAC*GTCGGATCACTGAGCGAGCGA TCTGAGAAGTGGCACNNNNNNNNNNNNNNNNNNNN (SEQ ID NO: 169) |
| sgRNA1.4 | *AGGACAGAATTTTTCAACGGGTGTGCCAATGGCCACTTTCCAGGTGGCAAAGCCCGTTGA ACTTCTCAAAAAGAACGCTCGCTCAGTGTTCTGAC*GTCGGATCACTGAGCGAGCGATCTG AGAAGTGGCACNNNNNNNNNNNNNNNNNNNN (SEQ ID NO: 170) |
| sgRNA1.5 | *CAGAATTTTTCAACGGGTGTGCCAATGGCCACTTTCCAGGTGGCAAAGCCCGTTGAACTT CTCAAAAAGAACGCTCGCTCAGTGTTCTGAC*GTCGGATCACTGAGCGAGCGATCTGAGAA GTGGCACNNNNNNNNNNNNNNNNNNNN (SEQ ID NO: 171) |
| sgRNA3 | *GTCTAAAGGACAGAATTTTTCAACGGGTGTGCCAATAGGTGGCAAAGCCCGTTGAACTTC TCAAAAAGAACGCTCGCTCAGTGTTCTGAC*GTCGGATCACTGAGCGAGCGATCTGAGAAG TGGCACNNNNNNNNNNNNNNNNNNNN (SEQ ID NO: 172) |
| sgRNA4 | *GTCTAAAGGACAGAATTTTTCAACGGGTGTAAAGCCCGTTGAACTTCTCAAAAAGAACGC TCGCTCAGTGTTCTGAC*GTCGGATCACTGAGCGAGCGATCTGAGAAGTGGCACNNNNNNNN NNNNNNNNNNNN (SEQ ID NO: 173) |
| sgRNA5 | *GTCTAAAGGACAGAATTTTTCAACGGGTGTGCCAATGGCCACTTTCCAGGTGGCAAAGCC CGTTGAACTTCTCAAAAAGAACGCTCGCTCAGTGTT*ATCACTGAGCGAGCGATCTGAGAA GTGGCACNNNNNNNNNNNNNNNNNNNN (SEQ ID NO: 174) |
| sgRNA6 | *GTCTAAAGGACAGAATTTTTCAACGGGTGTGCCAATGGCCACTTTCCAGGTGGCAAAGCC CGTTGAACTTCTCAAAAAGAAC*GATCTGAGAAGTGGCACNNNNNNNNNNNNNNNNNNNN (SEQ ID NO: 175) |
| sgRNA7 | *GTCTAAAGGACAGAATTTTTCAACGGGTGTGCCAATGGCCACTTTCCAGGTGGCAAAGCC CGTTGAACTTCTCAAAA*AGCTGAGAAGTGGCACNNNNNNNNNNNNNNNNNNNN (SEQ ID NO: 176) |
| sgRNA8 | *GTCTAAAGGACAGAATTTTTCAACGGGTGTGCCAATGGCCACTTTCCAGGTGGCAAAGCC CGTTGAACTTCTCAAA*GCTGAGAAGTGGCACNNNNNNNNNNNNNNNNNNNN (SEQ ID NO: 177) |
| sgRNA9 | *GTCTAAAGGACAGAATTTTTCAACGGGTGTGCCAATGGCCACTTTCCAGGTGGCAAAGCC CGTTGAACTTCTCAAA*ACTGAGAAGTGGCACNNNNNNNNNNNNNNNNNNNN (SEQ ID NO: 178) |
| sgRNA10 | *GTCTAAAGGACAGAATTTTTCAACGGGTGTGCCAATGGCCACTTTCCAGGTGGCAAAGCC CGTTGAACTTCTCAAG*CGAGAAGTGGCACNNNNNNNNNNNNNNNNNNNN (SEQ ID NO: 179) |
| sgRNA11 | *GTCTAAAGGACAGAATTTTTCAACGGGTGTGCCAATGGCCACTTTCCAGGTGGCAAAGCC CGTTGAACTTCTAA*GCAGAAGTGGCACNNNNNNNNNNNNNNNNNNNN (SEQ ID NO: 180) |

TABLE 4-continued

Sequences for AaC2c1 single guide RNA (sgRNA) optimization. Single chimeric guide RNA (sgRNA) from *Alicyclobacillus acidiphilus* type V-B CRISPR locus were engineered. The italics and bold font highlighted the tracrRNA and the crRNA sequences, respectively. The continuous N at 3'-end represented 20 nt protospacer sequence (target sequence). Since no direct repeat (DR) array contained in *A. acidiphilus* CRISPR locus, we adopted the crRNA sequence from orthologous *Alicyclobacillus acidoterrestris* type V-B CRISPR locus and engineered with tracrRNA from *A. acidiphilus* type V-B CRISPR locus. Sequences of optimized sgRNAs from original sgRNA1 were listed. N is independently selected from A, T, G, C.

| sgRNA name | sgRNA sequences (5'- 3') |
|---|---|
| sgRNA12 | *GTCTAAAGGACAGAATTTTTCAACGGGTGTGCCAATGGCCACTTTCCAGGTGGCAAAGCCCGTTGAACTTCAA*__GCGAAGTGGCAC__NNNNNNNNNNNNNNNNNNNN (SEQ ID NO: 181) |

Example 4. Off-Target Analysis and Prediction

The experiment results of FIG. 7A show the effect of proto-spacer length on AaC2c1 targeting activity in vivo. The results show that the proto-spacer sequence of less than 18 nucleotides could achieve efficient cleavage.

FIG. 7B shows the effect of sgRNA-target DNA single mismatch on AaC2c1 targeting activity in vivo. The results show tolerance to mismatch at position 7 from the 5' end of the target sequence.

FIG. 7C shows the effect of sgRNA-target DNA consecutive mismatches on AaC2c1 targeting activity in vivo. The results show that AaC2c1 is intolerant to sgRNA-target DNA continuous mismatches in vivo.

FIG. 7D shows efficiencies of endogenous human RNF2 gene disruption mediated by AaC2c1 and sgRNA bearing variable proto-spacer length. Error bars indicate standard errors of the mean (s.e.m), n=3.

Figures 8A, 8B:
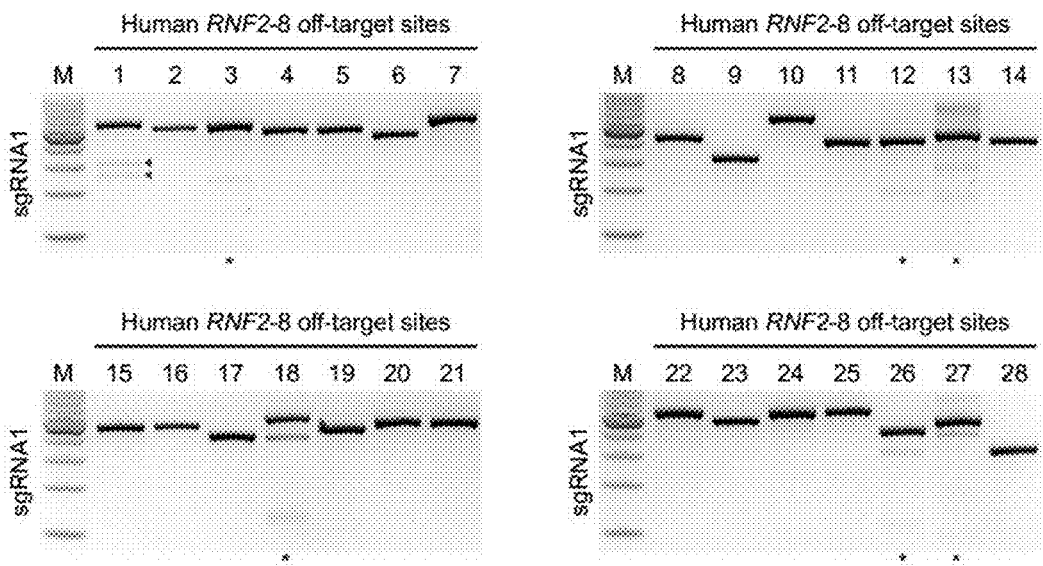
FIGS. 8A-8B show the off-target effect analysis of AaC2c1.

Based on the experiment results in FIG. 7, endogenous off-target sites prediction and analysis are performed. FIG. 8A shows T7EI analysis of human endogenous RNF2 gene off-target sites induced by target site 8. Triangles mark the predicted cleavage bands. Note that off-target site 1 is on RNF2 pseudogene locus and has the exactly same spacer and PAM sequences. Symbol "*" under the lanes indicated off-target sites with inconsistent cleavage bands. FIG. 8B shows representative sequences of off-target site 1, 18, 26, 27. It appears that the cleavage band indicated by "*" is due to PCR amplification.

TABLE 5

Off-target site analysis. Predicted genomic off-target sites of human endogenous RNF2 gene target site 8 were listed. PAM sequences of off-target sites were underlined and mismatches highlighted in italic font.

| Off-target sites | Off-target sequences (5' - 3') |
|---|---|
| Off-target 1 | __TTG__TAGTCATGGTGTTCTTCAAC (SEQ ID NO: 182) |
| Off-Target 2 | __TTG__*T*TGTCATGGTGTTC*CT*AGGG (SEQ ID NO: 183) |
| Off-Target 3 | __TTTT__AGTCAT*T*GTATTCTTCAGC (SEQ ID NO: 184) |
| Off-Target 4 | __TTTT__AGTCATGG*T*TTTCTTAT*T*C (SEQ ID NO: 185) |
| Off-Target 5 | __TTTT__AGTC*T*TGGTGT*T*TTTCACA (SEQ ID NO: 186) |
| Off-Target 6 | __TTTT__AGTCATGATGTTCT*GT*AAA (SEQ ID NO: 187) |
| Off-Target 7 | __TTTT__A*T*TCATTGTGTTCTTCAGC (SEQ ID NO: 188) |
| Off-Target 8 | __TTTT__AGTCA*A*GGTGTTCAGC*CCC* (SEQ ID NO: 189) |
| Off-Target 9 | __TTTT__A*T*TCATTGTGTTCTTCAGC (SEQ ID NO: 190) |
| Off-Target 10 | __TTA__TAGTCATGGTC*T*TCTATGTG (SEQ ID NO: 191) |
| Off-Target 11 | __TTA__TAGTCATG*C*TGTTCA*GT*GTC (SEQ ID NO: 192) |
| Off-Target 12 | __TTA__TAGTCAT*T*TGTGTTCC*TT*CCT (SEQ ID NO: 193) |
| Off-Target 13 | __TTA__TAGTA*A*TGGTGTTCTTATTA (SEQ ID NO: 194) |
| Off-Target 14 | __TTA__TA*A*TCATGGTG*C*TCTTCACA (SEQ ID NO: 195) |
| Off-Target 15 | __TTA__TAGTA*A*TGGTGTTCTCAAAA (SEQ ID NO: 196) |
| Off-Target 16 | __TTA__TAGTCA*T*TGTATTCTTCAAT (SEQ ID NO: 197) |
| Off-Target 17 | __TTA__TAGTCATGGTA*T*TCTTACAT (SEQ ID NO: 198) |
| Off-Target 18 | __TTA__TAGTCA*T*TGTGTTCA*AAAAA* (SEQ ID NO: 199) |
| Off-Target 19 | __TTA__TAGTCATGGTC*T*TCTATGTG (SEQ ID NO: 200) |
| Off-Target 20 | __TTC__TAGTCA*T*TGTGTTCAG*A*GGA (SEQ ID NO: 201) |
| Off-Target 21 | __TTC__TAGT*CC*TGGTGTTCTCTCTA (SEQ ID NO: 202) |

TABLE 5-continued

Off-target site analysis. Predicted genomic off-target sites of human endogenous RNF2 gene target site 8 were listed. PAM sequences of off-target sites were underlined and mismatches highlighted in italic font.

| Off-target sites | Off-target sequences (5' - 3') |
|---|---|
| Off-Target 22 | TTCTAGTCATGGAGCTCTTCACA (SEQ ID NO: 203) |
| Off-Target 23 | TTCTAATCATGGTGTTCTAGAAT (SEQ ID NO: 204) |
| Off-Target 24 | TTCTAGTCAAGGTGTTCTATGGC (SEQ ID NO: 205) |
| Off-Target 25 | TTCTAGTCATGGAGTTCTAACTA (SEQ ID NO: 206) |
| Off-Target 26 | TTCTATTCATGGTGTTCCTTAAG (SEQ ID NO: 207) |
| Off-Target 27 | TTCTAGACATGGTGTTCCATTTG (SEQ ID NO: 208) |
| Off-Target 28 | TTCTAGTCATTGTGTTTTCAGT (SEQ ID NO: 209) |

Example 5. Catalytic Residues of AaC2c1 Required for DNA Cleavage

FIG. 9A is a schematic representation of AaC2c1 domain structure with catalytic residue mutations. The catalytic residues were identified based on sequence homology with *A. acidoterrestris* C2c1 (AacC2c1) (PDB: 5WQE).

FIG. 9B shows in vitro DNA cleavage analysis of AaC2c1 variants with catalytic residue mutations. FIG. 9C shows the effect of catalytic residue mutations og AaC2c1 on DNA targeting in vivo by T7EI analysis. The results showed that R785A mutation eliminated DNA cutting activity both in vivo and in vitro.

FIG. 9D (Upper) is a schematic of in vitro cleavage of Nb.BtsI-nicked dsDNA fragment using site-directed mutated AaC2c1. FIG. 9D (Lower) The nicked dsDNA could not be cleaved in vitro by the AaC2c1 variant (R785A). It can be seen that the AaC2c1 variant comprising R785A is the variant without endonuclease activity. Such dC2c1 variants can significantly extend the use of AaC2c1.

Figure 10:
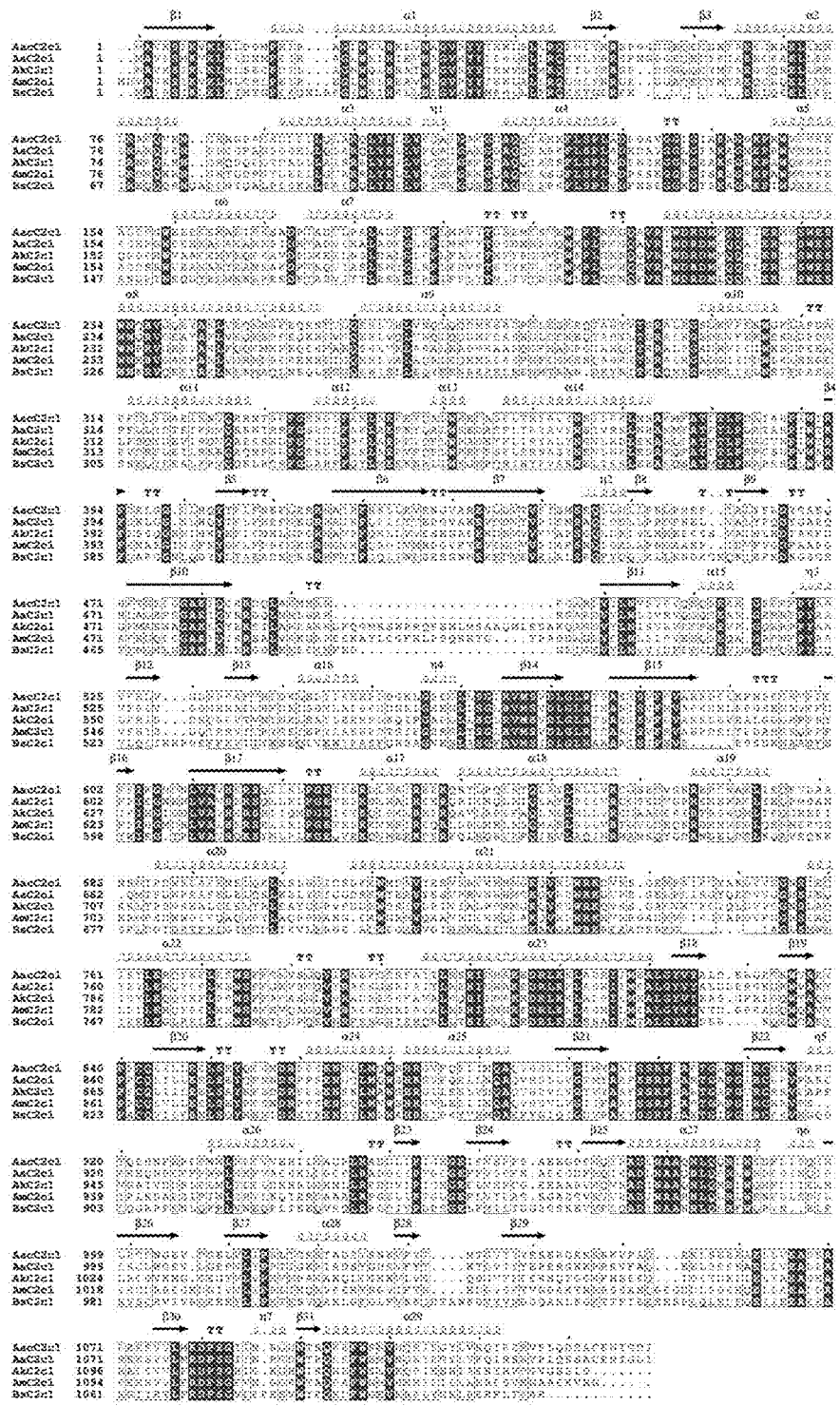
FIG. 10 shows sequence alignment and structural analysis of C2c1 proteins derived from different species. Sequences of AacC2c1 (SEQ ID NO: 1), AaC2c1 (SEQ ID NO: 292), AkC2c1 (SEQ ID NO: 293), AmC2c1 (SEQ ID NO: 294), and BsC2c1 (SEQ ID NO: 295) are shown.

FIG. 10 shows the protein alignment of AacC2c1, AaC2c1, AkC2c1, AmC2c1 and BsC2c1. Multiple sequence alignment of amino acid sequences of AacC2c1, AaC2c1, AkC2c1, AmC2c1 and BsC2c1 shows highly conserved residues. Strict identical residues are highlighted with a red background and conserved mutations are highlighted with an outline and red font. Second structure prediction is highlighted above the alignment. Alpha-helices are shown as a curly symbol and beta-strands shown as arrows. Strict alpha-turns are rendered as TTT and strict beta-turns as TT.

SEQ IN NO: 1
AaC2c1 protein sequence
MAVKSMKVKLRLDNMPEIRAGLWKLHTEVNAGVRYYTEWLSLLRQENLYRRSPNGDGEQECYKTAEEC

KAELLERLRARQVENGHCGPAGSDDELLQLARQLYELLVPQAIGAKGDAQQIARKFLSPLADKDAVGG

LGIAKAGNKPRWVRMREAGEPGWEEEKAKAEARKSTDRTADVLRALADFGLKPLMRVYTDSDMSSVQW

KPLRKGQAVRTWDRDMFQQAIERMMSWESWNQRVGEAYAKLVEQKSRFEQKNFVGQEHLVQLVNQLQQ

DMKEASHGLESKEQTAHYLTGRALRGSDKVFEKWEKLDPDAPFDLYDTEIKNVQRRNTRRFGSHDLFA

KLAEPKYQALWREDASFLTRYAVYNSIVRKLNHAKMFATFTLPDATAHPIWTRFDKLGGNLHQYTFLF

NEFGEGRHAIRFQKLLTVEDGVAKEVDDVTVPISMSAQLDDLLPRDPHELVALYFQDYGAEQHLAGEF

GGAKIQYRRDQLNHLHARRGARDVYLNLSVRVQSQSEARGERRPPYAAVFRLVGDNHRAFVHFDKLSD

YLAEHPDDGKLGSEGLLSGLRVMSVDLGLRTSASISVFRVARKDELKPNSEGRVPFCFPIEGNENLVA

VHERSQLLKLPGETESKDLRAIREERQRTLRQLRTQLAYLRLLVRCGSEDVGRRERSWAKLIEQPMDA

NQMTPDWREAFEDELQKLKSLYGICGDREWTEAVYESVRRVWRHMGKQVRDWRKDVRSGERPKIRGYQ

KDVVGGNSIEQIEYLERQYKFLKSWSFFGKVSGQVIRAEKGSRFAITLREHIDHAKEDRLKKLADRII

MEALGYVYALDDERGKGKWVAKYPPCQLILLEELSEYQFNNDRPPSENNQLMQWSHRGVFQELLNQAQ

VHDLLVGTMYAAFSSRFDARTGAPGIRCRRVPARCAREQNPEPFPWWLNKFVAEHKLDGCPLRADDLI

PTGEGEFFVSPFSAEEGDFHQIHADLNAAQNLQRRLWSDFDISQIRLRCDWGEVDGEPVLIPRTTGKR

TADSYGNKVFYTKTGVTYYERERGKKRRKVFAQEELSEEEAELLVEADEAREKSVVLMRDPSGIINRG

DWTRQKEFWSMVNQRIEGYLVKQIRSRVRLQESACENTGDI

SEQ IN NO: 2
C2c1 coding sequence from *Alicyclobacillus acidiphilus* NBRC 100859 (GeneBank ID: NZ_BCQI01000053.1)
ATGGCCGTTAAATCCATGAAAGTGAAACTTCGCCTCGATAATATGCCGGAGATTCGGGCTGGTTTATG

GAAACTCCATACGGAGGTCAACGCGGGGGTTCGATATTACACGGAATGGCTGAGTCTTCTGCGTCAAG

AGAATTTGTATCGAAGAAGTCCGAATGGGGACGGAGAGCAAGAATGTTATAAGACTGCAGAAGAATGC

-continued

```
AAAGCCGAATTGTTGGAGCGGCTGCGCGCGCGTCAAGTGGAGAATGGACACTGTGGTCCGGCGGGATC
GGACGATGAATTGCTGCAGTTGGCTCGTCAACTTTATGAACTGTTGGTTCCGCAGGCGATAGGTGCGA
AAGGCGATGCGCAGCAAATTGCGCGCAAGTTTTTGAGCCCCTTAGCCGACAAGGATGCAGTGGGTGGG
CTTGGAATCGCGAAGGCGGGGAACAAACCGCGGTGGGTTCGCATGCGCGAAGCGGGAGAACCTGGCTG
GGAAGAGGAGAAGGCGAAGGCTGAGGCGAGGAAATCTACGGATCGAACTGCGGATGTTTTGCGCGCGC
TCGCGGATTTTGGGTTAAAGCCACTGATGCGCGTGTACACCGATTCTGACATGTCATCTGTTCAGTGG
AAACCGCTTCGGAAGGGCCAAGCGGTTCGGACGTGGGACAGGGATATGTTCCAACAGGCCATCGAGCG
GATGATGTCGTGGGAGTCGTGGAATCAGCGCGTTGGCGAAGCGTACGCGAAACTGGTAGAGCAAAAAA
GTCGATTTGAGCAGAAGAACTTCGTCGGCCAGGAACATTTGGTTCAACTCGTCAATCAGTTGCAACAA
GATATGAAAGAAGCATCGCACGGGCTCGAATCGAAAGAGCAAACCGCACATTATCTGACGGGACGGGC
ATTGCGCGGATCGGACAAAGTGTTTGAGAAGTGGGAGAAACTCGACCCTGATGCGCCATTCGATTTGT
ACGACACCGAAATCAAGAACGTGCAGAGACGTAACACGAGGCGATTCGGCTCACACGACTTGTTCGCG
AAATTGGCGGAACCGAAGTATCAGGCCCTGTGGCGCGAAGATGCTTCGTTTCTCACGCGTTACGCGGT
GTACAACAGCATCGTTCGCAAACTGAATCACGCCAAAATGTTCGCGACGTTTACTTTACCGGATGCAA
CTGCGCATCCGATTTGGACTCGCTTTGATAAATTGGGCGGGAATTTGCACCAGTACACCTTTTTGTTC
AACGAATTCGGAGAAGGCAGGCACGCGATTCGTTTTCAAAAGCTGTTGACCGTCGAAGATGGTGTCGC
AAAAGAAGTTGATGATGTAACGGTGCCCATTTCCATGTCAGCGCAATTGGATGATCTGCTGCCAAGAG
ATCCCCATGAACTGGTTGCACTATATTTTCAAGATTATGGAGCCGAACAGCATTTGGCGGGTGAATTC
GGTGGCGCGAAGATTCAGTACCGTCGGGATCAACTAAATCATTTGCACGCACGCAGAGGGGCGAGGGA
TGTTTATCTCAATCTCAGCGTACGTGTGCAGAGCCAGTCTGAGGCACGGGGAGAACGCCGCCCGCCGT
ATGCCGCAGTATTCCGCCTGGTCGGGACAACCATCGTGCGTTTGTCCATTTTGATAAATTATCGGAT
TATCTTGCGGAACATCCGGATGATGGGAAGCTTGGATCGGAGGGGCTGCTTTCCGGGCTACGGGTGAT
GAGTGTCGATCTCGGCCTTCGCACATCGGCATCGATTTCCGTTTTTCGCGTTGCCCGGAAGGACGAGT
TGAAGCCGAACTCGGAAGGGCGTGTCCCATTCTGTTTTCCGATTGAAGGGAATGAAAATCTCGTCGCG
GTTCATGAACGATCTCAACTTTTGAAGCTGCCTGGCGAAACAGAGTCAAAGGACCTGCGGGCTATCCG
AGAAGAGCGCCAACGGACCCTGCGGCAGCTGCGGACGCAACTGGCGTATTTGCGGCTGCTCGTGCGGT
GTGGGTCGGAAGATGTGGGACGGCGTGAACGGAGTTGGGCAAAGCTTATTGAGCAGCCCATGGATGCC
AATCAGATGACACCGGATTGGCGCGAAGCCTTTGAAGACGAACTTCAGAAGCTTAAGTCACTCTATGG
TATCTGTGGCGACAGGGAATGGACGGAGGCTGTCTACGAGAGCGTTCGCCGCGTGTGGCGCCATATGG
GCAAACAGGTTCGCGATTGGCGAAAGGACGTACGGAGTGGAGAGCGGCCGAAGATTCGCGGCTATCAA
AAAGATGTGGTCGGCGGAAATTCGATTGAGCAAATTGAGTATCTTGAACGGCAGTACAAGTTTCTCAA
GAGTTGGAGCTTTTTTGGCAAGGTATCGGGACAAGTGATTCGTGCGGAGAAGGGATCCCGATTTGCGA
TCACGCTGCGTGAACACATTGATCACGCGAAGGAAGACCGGCTGAAGAAATTGGCGGATCGCATCATT
ATGGAGGCGCTCGGTTATGTGTACGCGTTGGATGATGAGCGCGGCAAGGAAAGTGGGTTGCGAAGTA
TCCGCCGTGCCAGCTCATCCTGCTGGAGGAATTGAGCGAGTACCAGTTCAATAACGACAGGCCTCCGA
GTGAAAACAATCAGTTGATGCAATGGAGCCATCGCGGCGTGTTCCAGGAGTTGTTGAATCAGGCCCAA
GTCCACGATTTACTCGTTGGGACGATGTATGCAGCGTTCTCGTCGCGATTCGACGCGCGAACCGGGC
ACCGGGTATCCGCTGTCGCAGGGTACCGGCGCGTTGCGCTCGGGAGCAGAATCCAGAACCATTTCCTT
GGTGGCTGAACAAGTTTGTGGCGGAACACAAGTTGGATGGTTGTCCCTTACGGGCAGACGACCTCATC
CCCACGGGTGAAGGAGAGTTTTTTGTCTCGCCGTTCAGTGCGGAGGAAGGGGACTTTCATCAGATTCA
```

-continued
TGCCGACCTGAATGCGGCGCAAAACCTGCAGCGGCGACTCTGGTCTGATTTTGATATCAGTCAAATTC

GGTTGCGGTGTGATTGGGGTGAAGTGGACGGTGAACCCGTTCTGATCCCAAGGACCACAGGAAAGCGA

ACGGCGGATTCATATGGCAACAAGGTGTTTTATACCAAAACAGGTGTCACCTATTATGAGCGAGAGCG

GGGGAAGAAGCGGAGAAAGGTTTTCGCGCAAGAGGAATTGTCGGAGGAAGAGGCGGAGTTGCTTGTGG

AAGCAGACGAGGCAAGGGAGAAATCGGTCGTTTTGATGCGTGATCCGTCCGGCATTATCAATCGTGGC

GACTGGACCAGGCAAAAGGAGTTTTGGTCGATGGTGAACCAGCGGATTGAAGGATACTTGGTCAAGCA

GATTCGCTCGCGCGTTCGCTTACAAGAAAGTGCGTGTGAAAACACGGGGGATATT

SEQ IN NO: 3

Humanized AaC2c1 coding sequence
ATGGCCGTGAAGAGCATGAAGGTGAAGCTGCCCTGGACAACATGCCCGAGATCCGCGCCGGCCTGTG

GAAGCTGCACACCGAGGTGAACGCCGGCGTGCGCTACTACACCGAGTGGCTGAGCCTGCTGCGCCAGG

AGAACCTGTACCGCCGCAGCCCCAACGGCGACGGCGAGCAGGAGTGCTACAAGACCGCCGAGGAGTGC

AAGGCCGAGCTGCTGGAGCGCCTGCGCGCCCGCCAGGTGGAGAACGGCCACTGCGGCCCCGCCGGCAG

CGACGACGAGCTGCTGCAGCTGGCCCGCCAGCTGTACGAGCTGCTGGTGCCCCAGGCCATCGGCGCCA

AGGGCGACGCCCAGCAGATCGCCCGCAAGTTCCTGAGCCCCCTGGCCGACAAGGACGCCGTGGGCGGC

CTGGGCATCGCCAAGGCCGGCAACAAGCCCCGCTGGGTGCGCATGCGCGAGGCCGGCGAGCCCGGCTG

GGAGGAGGAGAAGGCCAAGGCCGAGGCCCGCAAGAGCACCGACCGCACCGCCGACGTGCTGCGCGCCC

TGGCCGACTTCGGCCTGAAGCCCCTGATGCGCGTGTACACCGACAGCGACATGAGCAGCGTGCAGTGG

AAGCCCCTGCGCAAGGGCCAGGCCGTGCGCACCTGGGACCGCGACATGTTCCAGCAGGCCATCGAGCG

CATGATGAGCTGGGAGAGCTGGAACCAGCGCGTGGGCGAGGCCTACGCCAAGCTGGTGGAGCAGAAGA

GCCGCTTCGAGCAGAAGAACTTCGTGGGCCAGGAGCACCTGGTGCAGCTGGTGAACCAGCTGCAGCAG

GACATGAAGGAGGCCAGCCACGGCCTGGAGAGCAAGGAGCAGACCGCCCACTACCTGACCGGCCGCGC

CCTGCGCGGCAGCGACAAGGTGTTCGAGAAGTGGGAGAAGCTGGACCCCGACGCCCCCTTCGACCTGT

ACGACACCGAGATCAAGAACGTGCAGCGCCGCAACACCCGCCGCTTCGGCAGCCACGACCTGTTCGCC

AAGCTGGCCGAGCCCAAGTACCAGGCCCTGTGGCGCGAGGACGCCAGCTTCCTGACCCGCTACGCCGT

GTACAACAGCATCGTGCGCAAGCTGAACCACGCCAAGATGTTCGCCACCTTCACCCTGCCCGACGCCA

CCGCCCACCCCATCTGGACCCGCTTCGACAAGCTGGGCGGCAACCTGCACCAGTACACCTTCCTGTTC

AACGAGTTCGGCGAGGGCCGCCACGCCATCCGCTTCCAGAAGCTGCTGACCGTGGAGGACGGCGTGGC

CAAGGAGGTGGACGACGTGACCGTGCCCATCAGCATGAGCGCCCAGCTGGACGACCTGCTGCCCCGCG

ACCCCCACGAGCTGGTGGCCCTGTACTTCCAGGACTACGGCGCCGAGCAGCACCTGGCCGGCGAGTTC

GGCGGCGCCAAGATCCAGTACCGCCGCGACCAGCTGAACCACCTGCACGCCCGCCGCGGCGCCCGCGA

CGTGTACCTGAACCTGAGCGTGCGCGTGCAGAGCCAGAGCGAGGCCCGCGGCGAGCGCCGCCCCCCCT

ACGCCGCCGTGTTCCGCCTGGTGGGCGACAACCACCGCGCCTTCGTGCACTTCGACAAGCTGAGCGAC

TACCTGGCCGAGCACCCCGACGACGGCAAGCTGGGCAGCGAGGGCCTGCTGAGCGGCCTGCGCGTGAT

GAGCGTGGACCTGGGCCTGCGCACCAGCGCCAGCATCAGCGTGTTCCGCGTGGCCCGCAAGGACGAGC

TGAAGCCCAACAGCGAGGGCCGCGTGCCCTTCTGCTTCCCCATCGAGGGCAACGAGAACCTGGTGGCC

GTGCACGAGCGCAGCCAGCTGCTGAAGCTGCCCGGCGAGACCGAGAGCAAGGACCTGCGCGCCATCCG

CGAGGAGCGCCAGCGCACCCTGCGCCAGCTGCGCACCCAGCTGGCCTACCTGCGCCTGCTGGTGCGCT

GCGGCAGCGAGGACGTGGGCCGCCGCGAGCGCAGCTGGGCCAAGCTGATCGAGCAGCCCATGGACGCC

AACCAGATGACCCCCGACTGGCGCGAGGCCTTCGAGGACGAGCTGCAGAAGCTGAAGAGCCTGTACGG

CATCTGCGGCGACCGCGAGTGGACCGAGGCCGTGTACGAGAGCGTGCGCCGCGTGTGGCGCCACATGG

GCAAGCAGGTGCGCGACTGGCGCAAGGACGTGCGCAGCGGCGAGCGCCCCAAGATCCGCGGCTACCAG

```
AAGGACGTGGTGGGCGGCAACAGCATCGAGCAGATCGAGTACCTGGAGCGCCAGTACAAGTTCCTGAA

GAGCTGGAGCTTCTTCGGCAAGGTGAGCGGCCAGGTGATCCGCGCCGAGAAGGGCAGCCGCTTCGCCA

TCACCCTGCGCGAGCACATCGACCACGCCAAGGAGGACCGCCTGAAGAAGCTGGCCGACCGCATCATC

ATGGAGGCCCTGGGCTACGTGTACGCCCTGGACGACGAGCGCGGCAAGGGCAAGTGGGTGGCCAAGTA

CCCCCCCTGCCAGCTGATCCTGCTGGAGGAGCTGAGCGAGTACCAGTTCAACAACGACCGCCCCCCA

GCGAGAACAACCAGCTGATGCAGTGGAGCCACCGCGGCGTGTTCCAGGAGCTGCTGAACCAGGCCCAG

GTGCACGACCTGCTGGTGGGCACCATGTACGCCGCCTTCAGCAGCCGCTTCGACGCCCGCACCGGCGC

CCCCGGCATCCGCTGCCGCCGCGTGCCCGCCCGCTGCGCCCGCGAGCAGAACCCCGAGCCCTTCCCCT

GGTGGCTGAACAAGTTCGTGGCCGAGCACAAGCTGGACGGCTGCCCCCTGCGCGCCGACGACCTGATC

CCCACCGGCGAGGGCGAGTTCTTCGTGAGCCCCTTCAGCGCCGAGGAGGGCGACTTCCACCAGATCCA

CGCCGACCTGAACGCCGCCCAGAACCTGCAGCGCCGCCTGTGGAGCGACTTCGACATCAGCCAGATCC

GCCTGCGCTGCGACTGGGGCGAGGTGGACGGCGAGCCCGTGCTGATCCCCCGCACCACCGGCAAGCGC

ACCGCCGACAGCTACGGCAACAAGGTGTTCTACACCAAGACCGGCGTGACCTACTACGAGCGCGAGCG

CGGCAAGAAGCGCCGCAAGGTGTTCGCCCAGGAGGAGCTGAGCGAGGAGGAGGCCGAGCTGCTGGTGG

AGGCCGACGAGGCCCGCGAGAAGAGCGTGGTGCTGATGCGCGACCCCAGCGGCATCATCAACCGCGGC

GACTGGACCCGCCAGAAGGAGTTCTGGAGCATGGTGAACCAGCGCATCGAGGGCTACCTGGTGAAGCA

GATCCGCAGCCGCGTGCGCCTGCAGGAGAGCGCCTGCGAGAACACCGGCGACATC
```
SEQ IN NO: 4 dAaC2c1 protein sequence
```
MAVKSMKVKLRLDNMPEIRAGLWKLHTEVNAGVRYYTEWLSLLRQENLYRRSPNGDGEQECYKTAEEC

KAELLERLRARQVENGHCGPAGSDDELLQLARQLYELLVPQAIGAKGDAQQIARKFLSPLADKDAVGG

LGIAKAGNKPRWVRMREAGEPGWEEEKAKAEARKSTDRTADVLRALADFGLKPLMRVYTDSDMSSVQW

KPLRKGQAVRTWDRDMFQQAIERMMSWESWNQRVGEAYAKLVEQKSRFEQKNFVGQEHLVQLVNQLQQ

DMKEASHGLESKEQTAHYLTGRALRGSDKVFEKWEKLDPDAPFDLYDTEIKNVQRRNTRRFGSHDLFA

KLAEPKYQALWREDASFLTRYAVYNSIVRKLNHAKMFATFTLPDATAHPIWTRFDKLGGNLHQYTFLF

NEFGEGRHAIRFQKLLTVEDGVAKEVDDVTVPISMSAQLDDLLPRDPHELVALYFQDYGAEQHLAGEF

GGAKIQYRRDQLNHLHARRGARDVYLNLSVRVQSQSEARGERRPPYAAVERLVGDNHRAFVHFDKLSD

YLAEHPDDGKLGSEGLLSGLRVMSVDLGLRTSASISVERVARKDELKPNSEGRVPFCFPIEGNENLVA

VHERSQLLKLPGETESKDLRAIREERQRTLRQLRTQLAYLRLLVRCGSEDVGRRERSWAKLIEQPMDA

NQMTPDWREAFEDELQKLKSLYGICGDREWTEAVYESVRRVWRHMGKQVRDWRKDVRSGERPKIRGYQ

KDVVGGNSIEQIEYLERQYKFLKSWSFFGKVSGQVÄ AEKGSRFAITLREHIDHAKEDRLKKLADRII

MEALGYVYALDDERGKGKWVAKYPPCQLILLEELSEYQFNNDRPPSENNQLMQWSHRGVFQELLNQAQ

VHDLLVGTMYAAFSSRFDARTGAPGIRCRRVPARCAREQNPEPFPWWLNKFVAEHKLDGCPLRADDLI

PTGEGEFFVSPFSAEEGDFHQIHADLNAAQNLQRRLWSDFDISQIRLRCDWGEVDGEPVLIPRTTGKR

TADSYGNKVFYTKTGVTYYERERGKKRRKVFAQEELSEEEAELLVEADEAREKSVVLMRDPSGIINRG

DWTRQKEFWSMVNQRIEGYLVKQIRSRVRLQESACENTGDI
```
SEQ IN NO: 5

AkC2c1 protein sequence
```
MAVKSIKVKLRLSECPDILAGMWQLHRATNAGVRYYTEWVSLMRQEILYSRGPDGGQQCYMTAEDCQR

ELLRRLRNRQLHNGRQDQPGTDADLLAISRRLYEILVLQSIGKRGDAQQIASSFLSPLVDPNSKGGRG

EAKSGRKPAWQKMRDQGDPRWVAAREKYEQRKAVDPSKEILNSLDALGLRPLFAVFTETYRSGVDWKP

LGKSQGVRTWDRDMFQQALERLMSWESWNRRVGEEYARLFQQKMKFEQEHFAEQSHLVKLARALEADM
```

-continued

RAASQGFEAKRGTAHQITRRALRGADRVFEIWKSIPEEALFSQYDEVIRQVQAEKRRDFGSHDLFAKL

AEPKYQPLWRADETFLTRYALYNGVLRDLEKARQFATFTLPDACVNPIWTRFESSQGSNLHKYEFLFD

HLGPGRHAVRFQRLLVVESEGAKERDSVVVPVAPSGQLDKLVLREEEKSSVALHLHDTARPDGFMAEW

AGAKLQYERSTLARKARRDKQGMRSWRRQPSMLMSAAQMLEDAKQAGDVYLNISVRVKSPSEVRGQRR

PPYAALFRIDDKQRRVTVNYNKLSAYLEEHPDKQIPGAPGLLSGLRVMSVDLGLRTSASISVERVAKK

EEVEALGDGRPPHYYPIHGTDDLVAVHERSHLIQMPGETETKQLRKLREERQAVLRPLFAQLALLRLL

VRCGAADERIRTRSWQRLTKQGREFTKRLTPSWREALELELTRLEAYCGRVPDDEWSRIVDRTVIALW

RRMGKQVRDWRKQVKSGAKVKVKGYQLDVVGGNSLAQIDYLEQQYKFLRRWSFFARASGLVVRADRES

HFAVALRQHIENAKRDRLKKLADRILMEALGYVYEASGPREGQWTAQHPPCQLIILEELSAYRFSDDR

PPSENSKLMAWGHRGILEELVNQAQVHDVLVGTVYAAFSSRFDARTGAPGVRCRRVPARFVGATVDDS

LPLWLTEFLDKHRLDKNLLRPDDVIPTGEGEFLVSPCGEEAARVRQVHADINAAQNLQRRLWQNFDIT

ELRLRCDVKMGGEGTVLVPRVNNARAKQLFGKKVLVSQDGVTFFERSQTGGKPHSEKQTDLTDKELEL

IAEADEARAKSVVLFRDPSGHIGKGHWIRQREFWSLVKQRIESHTAERIRVRGVGSSLD

SEQ IN NO: 6
C2c1 coding sequence from *Alicyclobacillus kakegawensis*
NBRC 103104 (GeneBank ID: NZ_BCRP01000027.1)
ATGGCTGTAAAATCTATTAAGGTCAAGTTGCGGTTGTCAGAGTGCCCAGACATCCTGGCTGGCATGTG

GCAGCTCCACCGGGCGACAAACGCGGGGGTTCGATACTACACAGAATGGGTGAGCTTGATGCGCCAGG

AGATCCTCTACTCGCGCGGGCCGGACGGCGGTCAGCAGTGCTACATGACCGCGGAGGATTGCCAACGC

GAGCTGCTGCGGCGGCTGCGCAATCGCCAGCTCCATAATGGCCGCCAGGACCAGCCCGGTACAGATGC

AGACCTACTGGCAATCAGTAGGAGACTCTATGAAATTCTGGTCCTGCAATCCATCGGCAAGAGGGGGG

ACGCCCAGCAGATAGCGAGCAGCTTCCTCAGCCCTCTGGTCGATCCGAACTCCAAAGGTGGGCGGGGT

GAAGCCAAGTCCGGTCGAAAGCCTGCGTGGCAGAAGATGCGCGATCAAGGTGATCCTCGTTGGGTTGC

GGCAAGGGAAAAGTACGAGCAACGCAAGGCGGTTGATCCATCTAAAGAAATCCTGAATTCATTGGACG

CCCTGGGTCTCAGGCCGCTATTTGCGGTCTTCACGGAGACCTACAGGTCGGGAGTCGATTGGAAGCCG

CTCGGCAAAAGCCAAGGTGTGCGCACATGGGACCGTGACATGTTCCAGCAGGCCCTCGAGCGCCTGAT

GTCCTGGGAGTCTTGGAACCGCCGCGTGGGCGAGGAGTACGCCCGTCTTTTCCAACAGAAGATGAAGT

TCGAGCAGGAACACTTCGCGGAACAGTCTCATCTGGTTAAACTGGCGCGCGCGTTGGAGGCGGACATG

CGCGCCGCTTCACAGGGCTTCGAAGCCAAACGCGGCACTGCGCACCAGATCACAAGACGGGCGCTGCG

CGGGGCGGATCGGGTATTTGAGATATGGAAGAGTATTCCAGAGGAAGCTTTGTTCTCCCAATATGATG

AAGTGATTCGACAGGTCCAGGCGGAGAAAAGACGGGACTTTGGGTCCCATGATCTGTTCGCCAAGTTG

GCGGAACCGAAGTATCAGCCCCTGTGGCGCGCCGACGAGACCTTTTTGACGCGCTACGCCCTGTACAA

TGGAGTCTTGCGGGATTAGAGAAAGCGAGACAGTTCGCCACGTTCACGCTGCCGGATGCCTGCGTCA

ATCCAATTTGGACGCGTTTTGAAAGCAGCCAGGGGAGCAATCTGCATAAATATGAATTTCTCTTTGAC

CACCTGGGACCCGGACGGCACGCGGTGCGTTTTCAGAGGCTGCTGGTGGTAGAGAGCGAAGGTGCGAA

GGAGAGGGACTCGGTGGTGGTGCCAGTCGCGCCATCCGGGCAACTGGACAAGCTTGTCCTGCGTGAAG

AAGAGAAATCAAGCGTTGCCTTACACCTTCATGACACAGCCCGGCCGGACGGTTTCATGGCAGAATGG

GCGGGGGCGAAGCTGCAATATGAACGCAGTACCTTGGCACGCAAGGCGCGCCGTGATAAGCAAGGGAT

GCGGTCGTGGCGTAGGCAGCCGTCTATGCTGATGTCTGCGGCACAGATGTTGGAAGACGCAAAGCAAG

CCGGAGACGTGTATCTGAACATCAGTGTGCGTGTGAAGAGCCCCAGTGAAGTCCGCGGCCAGAGGCGG

CCTCCTTACGCGGCCCTGTTTCGGATAGACGATAAACAGCGGCGTGTGACCGTAAATTACAACAAACT

GTCGGCTTACCTAGAGGAACATCCGGATAAACAGATTCCAGGCGCACCTGGGCTCCTTTCCGGTCTTC

-continued

```
GGGTAATGAGCGTCGACCTTGGGTTGCGCACCTCCGCTTCCATCAGTGTGTTCCGTGTGGCAAAGAAG
GAAGAGGTGGAAGCGCTGGGCGACGGTCGTCCCCCTCATTATTATCCCATCCATGGCACTGACGACCT
GGTGGCGGTGCACGAGCGCTCACATTTGATTCAAATGCCAGGCGAAACCGAAACGAAACAGCTGCGCA
AGTTGCGTGAGGAACGGCAGGCTGTCTTGCGTCCACTGTTCGCTCAACTGGCCCTGCTACGGTTGCTG
GTCCGGTGTGGTGCAGCCGACGAGCGGATTCGTACACGCAGTTGGCAGCGCTTGACGAAGCAGGGGCG
TGAGTTTACGAAGCGATTGACGCCGTCCTGGCGGGAGGCGTTGGAATTGGAGTTAACTCGCTTGGAGG
CGTATTGCGGTAGGGTTCCAGACGACGAATGGAGCCGCATCGTTGATAGAACGGTAATCGCTTTGTGG
CGTCGCATGGGAAAACAGGTGCGCGATTGGCGTAAACAGGTGAAATCCGGTGCGAAAGTCAAGGTCAA
GGGGTACCAGCTGGATGTAGTCGGCGGCAACTCGCTGGCGCAAATCGATTATCTCGAACAGCAGTACA
AGTTTCTGCGGCGCTGGAGCTTCTTTGCGCGGGCCAGCGGTCTGGTTGTGCGGGCGGATCGCGAATCG
CATTTCGCAGTCGCTTTACGCCAGCACATTGAAAATGCCAAGCGGGATCGGCTGAAAAGTTGGCGGA
CCGCATCCTGATGGAGGCGCTGGGCTACGTGTATGAAGCTTCCGGGCCGCGCGAAGGACAGTGGACGG
CGCAGCATCCGCCGTGCCAGTTGATTATCTTGGAGGAATTAAGCGCGTACCGGTTCAGTGACGACCGT
CCGCCGAGCGAGAACAGTAAATTGATGGCTTGGGGGCATCGGGGAATTTTGGAGGAGTTGGTCAACCA
AGCACAGGTTCACGACGTGTTAGTGGGGACGGTGTACGCCGCTTTTTCGTCCCGCTTCGATGCCCGCA
CAGGCGCCCCTGGAGTGCGCTGCCGCCGGGTACCCGCACGTTTTGTCGGCGCGACGGTGGATGATTCA
CTGCCGCTTTGGCTCACAGAGTTTCTGGACAAGCACAGGCTGGATAAAAACCTCCTGCGGCCTGACGA
TGTGATTCCGACCGGAGAGGGTGAGTTTTTGGTTTCTCCGTGTGGCGAGGAAGCGGCTCGGGTTCGGC
AGGTGCACGCCGACATCAACGCGGCGCAAAACCTGCAGCGGAGGCTGTGGCAGAATTTTGACATTACA
GAGCTGCGTCTGCGCTGCGATGTGAAGATGGGTGGCGAAGGAACGGTGCTGGTACCAAGGGTCAACAA
CGCCCGCGCCAAACAACTGTTTGGAAAGAAGGTGTTGGTTTCGCAAGATGGCGTGACGTTCTTTGAAC
GCAGTCAAACAGGTGGGAAACCGCACAGCGAGAAGCAGACGGATTTGACCGACAAGGAACTAGAACTA
ATTGCGGAGGCGGACGAGGCGCGCGCCAAGTCGGTCGTCCTCTTTCGCGATCCGTCCGGGCACATCGG
CAAGGGCCACTGGATTCGCCAAAGGGAGTTTTGGTCGTTGGTGAAGCAAAGGATTGAATCGCACACGG
CGGAAAGGATACGGGTTCGCGGCGTCGGTAGCTCGCTGGAT
```

SEQ IN NO: 7
Humanized AkC2c1 coding sequence
```
ATGGCCGTGAAGAGCATCAAGGTGAAGCTGCGCCTGAGCGAGTGCCCCGACATCCTGGCCGGCATGTG
GCAGCTGCACCGCGCCACCAACGCCGGCGTGCGCTACTACACCGAGTGGGTGAGCCTGATGCGCCAGG
AGATCCTGTACAGCCGCGGCCCCGACGGCGGCCAGCAGTGCTACATGACCGCCGAGGACTGCCAGCGC
GAGCTGCTGCGCCGCCTGCGCAACCGCCAGCTGCACAACGGCCGCCAGGACCAGCCCGGCACCGACGC
CGACCTGCTGGCCATCAGCCGCCGCCTGTACGAGATCCTGGTGCTGCAGAGCATCGGCAAGCGCGGCG
ACGCCCAGCAGATCGCCAGCAGCTTCCTGAGCCCCCTGGTGGACCCCAACAGCAAGGGCGGCCGCGGC
GAGGCCAAGAGCGGCCGCAAGCCCGCCTGGCAGAAGATGCGCGACCAGGGCGACCCCCGCTGGGTGGC
CGCCCGCGAGAAGTACGAGCAGCGCAAGGCCGTGGACCCCAGCAAGGAGATCCTGAACAGCCTGGACG
CCCTGGGCCTGCGCCCCCTGTTCGCCGTGTTCACCGAGACCTACCGCAGCGGCGTGGACTGGAAGCCC
CTGGGCAAGAGCCAGGGCGTGCGCACCTGGGACCGCGACATGTTCCAGCAGGCCCTGGAGCGCCTGAT
GAGCTGGGAGAGCTGGAACCGCCGCGTGGGCGAGGAGTACGCCCGCCTGTTCCAGCAGAAGATGAAGT
TCGAGCAGGAGCACTTCGCCGAGCAGAGCCACCTGGTGAAGCTGGCCCGCGCCCTGGAGGCCGACATG
CGCGCCGCCAGCCAGGGCTTCGAGGCCAAGCGCGGCACCGCCCACCAGATCACCCGCCGCGCCCTGCG
CGGCGCCGACCGCGTGTTCGAGATCTGGAAGAGCATCCCCGAGGAGGCCCTGTTCAGCCAGTACGACG
AGGTGATCGCCAGGTGCAGGCCGAGAAGCGCCGCGACTTCGGCAGCCACGACCTGTTCGCCAAGCTG
```

-continued

```
GCCGAGCCCAAGTACCAGCCCCTGTggcgcgccGACGAGACCTTCCTGACCCGCTACGCCCTGTACAA
CGGCGTGCTGCGCGACCTGGAGAAGGCCCGCCAGTTCGCCACCTTCACCCTGCCCGACGCCTGCGTGA
ACCCCATCTGGACCCGCTTCGAGAGCAGCCAGGGCAGCAACCTGCACAAGTACGAGTTCCTGTTCGAC
CACCTGGGCCCCGGCCGCCACGCCGTGCGCTTCCAGCGCCTGCTGGTGGTGGAGAGCGAGGGCGCCAA
GGAGCGCGACAGCGTGGTGGTGCCCGTGGCCCCCAGCGGCCAGCTGGACAAGCTGGTGCTGCGCGAGG
AGGAGAAGAGCAGCGTGGCCCTGCACCTGCACGACACCGCCCGCCCCGACGGCTTCATGGCCGAGTGG
GCCGGCGCCAAGCTGCAGTACGAGCGCAGCACCCTGGCCCGCAAGGCCCGCCGCGACAAGCAGGGCAT
GCGCAGCTGGCGCCGCCAGCCCAGCATGCTGATGAGCGCCGCCCAGATGCTGGAGGACGCCAAGCAGG
CCGGCGACGTGTACCTGAACATCAGCGTGCGCGTGAAGAGCCCCAGCGAGGTGCGCGGCCAGCGCCGC
CCCCCCTACGCCGCCCTGTTCCGCATCGACGACAAGCAGCGCCGCGTGACCGTGAACTACAACAAGCT
GAGCGCCTACCTGGAGGAGCACCCCGACAAGCAGATCCCCGGCGCCCCCGGCCTGCTGAGCGGCCTGC
GCGTGATGAGCGTGGACCTGGGCCTGCGCACCAGCGCCAGCATCAGCGTGTTCCGCGTGGCCAAGAAG
GAGGAGGTGGAGGCCCTGGGCGACGGCCGCCCCCCCCACTACTACCCCATCCACGGCACCGACGACCT
GGTGGCCGTGCACGAGCGCAGCCACCTGATCCAGATGCCCGGCGAGACCGAGACCAAGCAGCTGCGCA
AGCTGCGCGAGGAGCGCCAGGCCGTGCTGCGCCCCCTGTTCGCCCAGCTGGCCCTGCTGCGCCTGCTG
GTGCGCTGCGGCGCCGCCGACGAGCGCATCCGCACCCGCAGCTGGCAGCGCCTGACCAAGCAGGGCCG
CGAGTTCACCAAGCGCCTGACCCCCAGCTGGCGCGAGGCCCTGGAGCTGGAGCTGACCCGCCTGGagg
cctACTGCGGCCGCGTGCCCGACGACGAGTGGAGCCGCATCGTGGACCGCACCGTGATCGCCCTGTGG
CGCCGCATGGGCAAGCAGGTGCGCGACTGGCGCAAGCAGGTGAAGAGCGGCGCCAAGGTGAAGGTGAA
GGGCTACCAGCTGGACGTGGTGGGCGGCAACAGCCTGGCCCAGATCGACTACCTGGAGCAGCAGTACA
AGTTCCTGCGCCGCTGGAGCTTCTTCGCCCGCGCCAGCGGCCTGGTGGTGCGCGCCGACCGCGAGAGC
CACTTCGCCGTGGCCCTGCGCCAGCACATCGAGAACGCCAAGCGCGACCGCCTGAAGAAGCTGGCCGA
CCGCATCCTGATGGAGGCCCTGGGCTACGTGTACGAGGCCAGCGGCCCCGCGAGGGCCAGTGGACCG
CCCAGCACCCCCCCCTGCCAGCTGATCATCCTGGAGGAGCTGAGCGCCTACCGCTTCAGCGACGACCGC
CCCCCCAGCGAGAACAGCAAGCTGATGGCCTGGGGCCACCGCGGCATCCTGGAGGAGCTGGTGAACCA
GGCCCAGGTGCACGACGTGCTGGTGGGCACCGTGTACGCCGCCTTCAGCAGCCGCTTCGACGCCCGCA
CCGGCGCCCCCGGCGTGCGCTGCCGCCGCGTGCCCGCCCGCTTCGTGGGCGCCACCGTGGACGACAGC
CTGCCCCTGTGGCTGACCGAGTTCCTGGACAAGCACCGCCTGGACAAGAACCTGCTGCGCCCCGACGA
CGTGATCCCCACCGGCGAGGGCGAGTTCCTGGTGAGCCCTGCGGCGAGGAGGCCGCCCGCGTGCGCC
AGGTGCACGCCGACATCAACGCCGCCCAGAACCTGCAGCGCCGCCTGTGGCAGAACTTCGACATCACC
GAGCTGCGCCTGCGCTGCGACGTGAAGATGGGCGGCGAGGGCACCGTGCTGGTGCCCCGCGTGAACAA
CGCCCGCGCCAAGCAGCTGTTCGGCAAGAAGGTGCTGGTGAGCCAGGACGGCGTGACCTTCTTCGAGC
GCAGCCAGACCGGCGGCAAGCCCCACAGCGAGAAGCAGACCGACCTGACCGACAAGGAGCTGGAGCTG
ATCGCCGAGGCCGACGAGGCCCGCGCCAAGAGCGTGGTGCTGTTCCGCGACCCCAGCGGCCACATCGG
CAAGGGCCACTGGATCCGCCAGCGCGAGTTCTGGAGCCTGGTGAAGCAGCGCATCGAGAGCCACACCG
CCCGAGCGCATCCGCGTGCGCGGCGTGGGCAGCAGCCTGGAC
```
                                                            SEQ IN NO: 8
pCAG-2AeGFP partial sequence (CAG-NLS-XmaI-NheI-NLS-T2A-eGFP-SV40)
```
gacattgattattgactagttattaatagtaatcaattacggggtcattagttcatagcccatatatg gagttccGCGTTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTCAATGGGTGG
```

-continued

```
ACTATTTACGGTAAACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTATGGGACTTTCCTAC
TTGGCAGTACATCTACGTATTAGTCATCGCTATTACCATGGGTCGAGGTGAGCCCCACGTTCTGCTTC
ACTCTCCCCATCTCCCCCCCCTCCCCACCCCCAATTTTGTATTTATTTATTTTTTAATTATTTTGTGC
AGCGATGGGGGCGGGGGGGGGGGGGCGCGCGCCAGGCGGGGCGGGGCGGGGCGAGGGGCGGGCGGG
GCGAGGCGGAGAGGTGCGGCGGCAGCCAATCAGAGCGGCGCGCTCCGAAAGTTTCCTTTTATGGCGAG
GCGGCGGCGGCGGCGGCCCTATAAAAAGCGAAGCGCGCGGCGGGCGGGAGTCGCTGCGTTGCCTTCGC
CCCGTGCCCCGCTCCGCGCCGCCTCGCGCCGCCCGCCCCGGCTCTGACTGACCGCGTTACTCCCACAG
GTGAGCGGGCGGGACGGCCCTTCTCCTCCGGGCTGTAATTAGCGCTTGGTTTAATGACGGCTCGTTTC
TTTTCTGTGGCTGCGTGAAAGCCTTAAAGGGCTCCGGGAGGGCCCTTTGTGCGGGGGGGAGCGGCTCG
GGGGGTGCGTGCGTGTGTGTGCGTGGGGAGCGCCGCGTGCGGCCCGCGCTGCCCGGCGGCTGTGAG
CGCTGCGGGCGCGCGCGGGCTTTGTGCGCTCCGCGTGTGCGCGAGGGGAGCGCGCCGGGGCGGT
GCCCCGCGGTGCGGGGGGGCTGCGAGGGGAACAAAGGCTGCGTGCGGGGTGTGTGCGTGGGGGGTGA
GCAGGGGGTGTGGGCGCGGCGGTCGGGCTGTAACCCCCCCCTGCACCCCCCTCCCCGAGTTGCTGAGC
ACGGCCCGGCTTCGGGTGCGGGGCTCCGTACGGGGCGTGGCGCGGGGCTCGCCGTGCCGGGCGGGGG
TGGCGGCAGGTGGGGGTGCCGGGCGGGGCGGGGCCGCCTCGGGCCGGGGAGGGCTCGGGGGAGGGGCG
CGGCGGCCCCGGAGCGCCGGCGGCTGTCGAGGCGCGGCGAGCCGCAGCCATTGCCTTTTATGGTAAT
CGTGCGAGAGGGCGCAGGGACTTCCTTTGTCCCAAATCTGTGCGGAGCCGAAATCTGGGAGGCGCCGC
CGCACCCCCTCTAGCGGGCGCGGGGCGAAGCGGTGCGGCGCCGGCAGGAAGGAAATGGGCGGGGAGGG
CCTTCGTGCGTCGCCGCGCCGCCGTCCCCTTCTCCATCTCCAGCCTCGGGGCTGTCCGCAGGGGACG
GCTGCCTTCGGGGGGACGGGGCAGGGCGGGGTTCGGCTTCTGGCGTGTGACCGGCGGCTCTAGcGCC
TCTGCTAACCATGTTCATGCCTTCTTCTTTTTCCTACAGctcctgggcaacgtgctggttattgtgct
gtctcatcattttggcaaaGCTAGTGAATTCTAATACGACTCACTATAGGCCGCCACCATGCCCAAGA
AGAAGAGGAAGGTTcccggggctagcCCAAAGAAGAAGAGGAAAGTCtctagaTACCCTTATGATGTT
CCAGATTATGCCGGATACCCATACGATGTCCCTGACTATGCAGGCTCCTACCCTTATGACGTCCCAGA
CTACGCCggatccAGGTCCGGCGGCGGAGAGGGCAGAGGAAGTCTTCTAACATGCGGTGACGTGGAGG
AGAATCCCGGCCCAATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGCGATGCCACCTACGG
CAAGCTGACCCTGAAGTTCATCTGCACCACCGGCAAGCTGCCCGTGCCCTGGCCCACCCTCGTGACCA
CCCTGACCTACGGCGTGCAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCTATATCATG
GCCGACAAGCAGAAGAACGGCATCAAGGTGAACTTCAAGATCCGCCACAACATCGAGGACGGCAGCGT
GCAGCTCGCCGACCACTACCAGCAGAACACCCCCATCGGCGACGGCCCCGTGCTGCTGCCCGACAACC
ACTACCTGAGCACCCAGTCCGCCCTGAGCAAAGACCCCAACGAGAAGCGCGATCACATGGTCCTGCTG
GAGTTCGTGACCGCCGCCGGGATCACTCTCGGCATGGACGAGCTGTACAAGtaactgcagcgcgggga
tctcatgctggagttcttcgcccacccccaacttgtttattgcagcttataatggttacaaataaagca
atagcatcacaaatttcacaaataaagcattttttttcactgcattctagttgtggtttgtccaaactc
atcaatgtatctta
```

SEQ IN NO: 9
BPK2104-ccdB partial sequence (lacI-T7-lacO-NLS-XmaI-SpeI-His$_{10}$-terminator)
TCACTGCCCGCTTTCCAGTCGGGAAACCTGTCGTGCCAGCTGCATTAATGAATCGGCCAACGCGCGGG

GAGAGGCGGTTTGCGTATTGGGCGCCAGGGTGGTTTTTCTTTTCACCAGTGAGACGGGCAACAGCTGA

TTGCCCTTCACCGCCTGGCCCTGAGAGAGTTGCAGCAAGCGGTCCACGCTGGTTTGCCCCAGCAGGCG

AAAATCCTGTTTGATGGTGGTTAACGGCGGGATATAACATGAGCTGTCTTCGGTATCGTCGTATCCCA

CTACCGAGATGTCCGCACCAACGCGCAGCCCGGACTCGGTAATGGCGCGCATTGCGCCCAGCGCCATC

TGATCGTTGGCAACCAGCATCGCAGTGGGAACGATGCCCTCATTCAGCATTTGCATGGTTTGTTGAAA

ACCGGACATGGCACTCCAGTCGCCTTCCCGTTCCGCTATCGGCTGAATTTGATTGCGAGTGAGATATT

TATGCCAGCCAGCCAGACGCAGACGCGCCGAGACAGAACTTAATGGGCCCGCTAACAGCGCGATTTGC

TGGTGACCCAATGCGACCAGATGCTCCACGCCCAGTCGCGTACCGTCTTCATGGGAGAAAATAATACT

GTTGATGGGTGTCTGGTCAGAGACATCAAGAAATAACGCCGGAACATTAGTGCAGGCAGCTTCCACAG

CAATGGCATCCTGGTCATCCAGCGGATAGTTAATGATCAGCCCACTGACGCGTTGCGCGAGAAGATTG

TGCACCGCCGCTTTACAGGCTTCGACGCCGCTTCGTTCTACCATCGACACCACCACGCTGGCACCCAG

TTGATCGGCGCGAGATTTAATCGCCGCGACAATTTGCGACGGCGCGTGCAGGGCCAGACTGGAGGTGG

CAACGCCAATCAGCAACGACTGTTTGCCCGCCAGTTGTTGTGCCACGCGGTTGGGAATGTAATTCAGC

TCCGCCATCGCCGCTTCCACTTTTTCCCGCGTTTTCGCAGAAACGTGGCTGGCCTGGTTCACCACGCG

GGAAACGGTCTGATAAGAGACACCGGCATACTCTGCGACATCGTATAACGTTACTGGTTTCACATTCA

CCACCCTGAATTGACTCTCTTCCGGGCGCTATCATGCCATACCGCGAAAGGTTTTGCGCCATTCGATG

GTGTCCGGGATCTCGACGCTCTCCCTTATGCGACTCCTGCATTAGGAAATTAATACGACTCACTATAG

GGGAATTGTGAGCGGATAACAATTCCCCTGTAGAAATAATTTTGTTTAACTTTAATAAGGAGATATCA

TATGCCCAAGAAGAAGAGGAAGGTT*cccggggctagt*CATCACCATCACCACCATCATCACCATCACT

AGGCGGCCGCATAATGCTTAAGTCGAACAGAAAGTAATCGTATTGTACACGGCCGCATAATCGAAATT

AAT*acgactcactatagg*GAATTCGGTACC*tgagaataactagca*TAACCCCTTGGGGCCTCTAAACG

GGTCTTGAGGGGTTTTTTGCTGAAACCTCAGGCATTT

SEQ IN NO: 10
pUC19-U6 partial sequence (U6-BasI-HindIII)
TGTAAAACGACGGCCAGTGAATTCGAGGGCCTATTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CGGA*GAGACC*NNNNNNN*GGTCTC*ANNNNNNNNNNNNNNNNNNNNNNNNNNNNNNNNNNNNNNN

NNNNNNNNNNNNNNNNNNNNNNNNNNNNNNNNNNA*AGCTT*GGCGTAATCATGGTCATAGCTGTTTCC

TG

SEQ IN NO: 11
pUC19-U6-AasgRNA1 partial sequence (U6-AasgRNA1_scaffold-BasI-BasI-terminator)
TGTAAAACGACGGCCAGTGAATTCGAGGGCCTATTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CGGGTCTAAAGGACAGAATTTTTCAACGGGTGTGCCAATGGCCACTTTCCAGGTGGCAAAGCCCGTTG

-continued

AACTTCTCAAAAAGAACGCTCGCTCAGTGTTCTGACGTCGGATCACTGAGCGAGCGATCTGAGAAGTG

GCACAGAGACCGAGAGAGGGTCTCAttttttttAAGCTTGGCGTAATCATGGTCATAGCTGTTTCCTG

SEQ IN NO: 12
pUC19-U6-AksgRNA partial sequence (U6-AksgRNA1_scaffold-BasI-BasI-terminator)
TGTAAAACGACGGCCAGTGAATTCGAGGGCCTATTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CGGtcgtctataGGACGGCGAGGACAACGGGAAGTGCCAATGTGCTCTTTCCAAGAGCAAACACCCCG

TTGGCTTCAAGATGACCGCTCGCTCAGCGATCTGACAACGGATCGCTGAGCGAGCGGTCTGAGAAGTG

GCACAGAGACCGAGAGAGGGTCTCAttttttttAAGCTTGGCGTAATCATGGTCATAGCTGTTTCCTG

SEQ IN NO: 13
pUC19-U6-AmsgRNA partial sequence (U6-AmsgRNA1_scaffold-BasI-BasI-terminator)
TGTAAAACGACGGCCAGTGAATTCGAGGGCCTATTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CGGggaattgccgatctaTAGGACGGCAGATTCAACGGGATGTGCCAATGCACTCTTTCCAGGAGTGA

ACACCCCGTTGGCTTCAACATGATCGCCCGCTCAACGGTCCGATGTCGGATCGTGAGCGGGCGATCT

GAGAAGTGGCACAGAGACCGAGAGAGGGTCTCAttttttttAAGCTTGGCGTAATCATGGTCATAGCT

GTTTCCTG

SEQ IN NO: 14
pUC19-U6-BssgRNA partial sequence (U6-BssgRNA1_scaffold-BasI-BasI-terminator)
TGTAAAACGACGGCCAGTGAATTCGAGGGCCTATTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CGGCCATAAGTCGACTTACATATCCGTGCGTGTGCATTATGGGCCCATCCACAGGTCTATTCCCACGG

ATAATCACGACTTTCCACTAAGCTTTCGAATGTTCGAAAGCTTAGTGGAAAGCTTCGTGGTTAGCACA

GAGACCGAGAGAGGGTCTCAttttttttAAGCTTGGCGTAATCATGGTCATAGCTGTTTCCTG

---

What we claimed is:

1. A genome editing system for site-directed modification of a target sequence in the genome of a cell, comprising at least one of the following i) to v):

i) a C2c1 protein or variant thereof, and a guide RNA;

ii) an expression construct comprising a nucleotide sequence encoding a C2c1 protein or variant thereof, and a guide RNA;

iii) a C2c1 protein or variant thereof, and an expression construct comprising a nucleotide sequence encoding a guide RNA;

iv) an expression construct comprising a nucleotide sequence encoding a C2c1 protein or variant thereof, and an expression construct comprising a nucleotide sequence encoding a guide RNA;

v) an expression construct comprising a nucleotide sequence encoding a C2c1 protein or variant thereof and a nucleotide sequence encoding a guide RNA;

wherein the guide RNA is capable of forming a complex with the C2c1 protein or variant thereof and targeting the C2c1 protein or variant thereof to the target sequence in the genome of the cell, resulting in substitution, deletion and/or addition of one or more nucleotides in the target sequence, wherein the C2c1 protein is a AaC2c1 protein derived from *Alicyclobacillus acidiphilus*, wherein 1) the AaC2c1 protein comprises an amino acid sequence set forth in SEQ ID NO:1, and the guide RNA is a sgRNA; or 2) the variant of the AaC2c1 protein comprises an amino acid sequence having at least 95% but less than 100% sequence identity to SEQ ID NO: 1, and has the RNA-mediated DNA binding activity and/or DNA cleavage activity of the AaC2c1 protein comprising an amino acid sequence set forth in SEQ ID NO:1.

2. The system of claim 1, wherein the variant of the AaC2c1 protein is a fusion protein of nuclease-dead AaC2c1 and a deaminase, wherein the deaminase is a cytosine deaminase capable of accepting single-stranded DNA as a substrate or an adenine deaminase capable of accepting single-stranded DNA as a substrate.

3. The system of claim 2, wherein the amino acid corresponding to position 785 of SEQ ID NO: 1 in the nuclease-dead AaC2c1 is substituted.

4. The system of claim 3, wherein the nuclease-dead AaC2c1 comprises an amino acid substitution R785A relative to SEQ ID NO: 1.

5. The system of any one of claim 4, wherein the guide RNA is a sgRNA.

6. The system of claim 5, wherein the sgRNA is encoded by a nucleotide sequence selected from the group consisting of:

(SEQ ID NO: 17)
5'-GTCTAAAGGACAGAATTTTTCAACGGGTGTGCCAATGGCCACTTTCC
AGGTGGCAAAGCCCGTTGAACTTCTCAAAAAGAACGCTCGCTCAGTGTTC
TGACGTCGGATCACTGAGCGAGCGATCTGAGAAGTGGCAC-N$_x$-3';

(SEQ ID NO: 18)
5'-AACTGTCTAAAGGACAGAATTTTTCAACGGGTGTGCCAATGGCCACT
TTCCAGGTGGCAAAGCCCGTTGAACTTCTCAAAAAGAACGCTCGCTCAGT
GTTCTGACGTCGGATCACTGAGCGAGCGATCTGAGAAGTGGCAC-N$_x$-3';

(SEQ ID NO: 19)
5'-CTGTCTAAAGGACAGAATTTTTCAACGGGTGTGCCAATGGCCACTTT
CCAGGTGGCAAAGCCCGTTGAACTTCTCAAAAAGAACGCTCGCTCAGTGT
TCTGACGTCGGATCACTGAGCGAGCGATCTGAGAAGTGGCAC-N$_x$-3';

(SEQ ID NO: 20)
5'-GTCTAAAGGACAGAATTTTTCAACGGGTGTGCCAATGGCCACTTTCC
AGGTGGCAAAGCCCGTTGAACTTCTCAAAAAGAACGCTCGCTCAGTGTTA
TCACTGAGCGAGCGATCTGAGAAGTGGCAC-N$_x$-3';

(SEQ ID NO: 21)
5'-GTCTAAAGGACAGAATTTTTCAACGGGTGTGCCAATGGCCACTTTCC
AGGTGGCAAAGCCCGTTGAACTTCTCAAAAAGAACGATCTGAGAAGTGGC
AC-N$_x$-3';

(SEQ ID NO: 22)
5'-GTCTAAAGGACAGAATTTTTCAACGGGTGTGCCAATGGCCACTTTCC
AGGTGGCAAAGCCCGTTGAACTTCTCAAAAAGCTGAGAAGTGGCAC-N$_x$-3';

(SEQ ID NO: 23)
5'-GTCTAAAGGACAGAATTTTTCAACGGGTGTGCCAATGGCCACTTTCC
AGGTGGCAAAGCCCGTTGAACTTCTCAAAGCTGAGAAGTGGCAC-N$_x$-3';

(SEQ ID NO: 24)
5'-GTCTAAAGGACAGAATTTTTCAACGGGTGTGCCAATGGCCACTTTCC
AGGTGGCAAAGCCCGTTGAACTTCTCAAAACTGAGAAGTGGCAC-N$_x$-3';

(SEQ ID NO: 25)
5'-GTCTAAAGGACAGAATTTTTCAACGGGTGTGCCAATGGCCACTTTCC
AGGTGGCAAAGCCCGTTGAACTTCTCAAGCGAGAAGTGGCAC-N$_x$-3';

(SEQ ID NO: 316)
5'-GTCTAAAGGACAGAATTTTTCAACGGGTGTGCCAATGGCCACTTTCC
AGGTGGCAAAGCCCGTTGAACTTCTAAGCAGAAGTGGCAC-N$_x$-3';
and (SEQ ID NO: 317)
5'-GTCTAAAGGACAGAATTTTTCAACGGGTGTGCCAATGGCCACTTTCC
AGGTGGCAAAGCCCGTTGAACTTCAAGCGAAGTGGCAC-N$_x$-3';

wherein Nx represents nucleotide sequence that consists of x consecutive nucleotides, capable of specifically hybridizing to the complement of the target sequence, N is independently selected from A, G, C and T; x is an integer of 18≤x≤35.

7. The system of claim 6, wherein x is 20.

8. A pharmaceutical composition for treating a disease in a subject in need thereof, comprising the genome editing system of any one of claims 1 and 2-6 and a pharmaceutically acceptable carrier, wherein the genome editing system is for modifying a gene related to a disease in a subject.

9. A method of site-directed modifying a target sequence in the genome of a cell, comprising introducing the system of any one of claims 1 and 2-6 into the cell.

10. The method of claim 9, wherein the cell is derived from mammals: human, mouse, rat, monkey, dog, pig, sheep, cattle, cat; poultry; chicken, duck, goose; plants; monocots and dicots, rice, corn, wheat, sorghum, barley, soybean, peanut and *Arabidopsis*.

11. The method of claim 9 or 10, wherein the system is introduced into the cell by a method selected from calcium phosphate transfection, protoplast fusion, electroporation, lipofection, microinjection, viral infection, gene gun method, PEG-mediated protoplast transformation, *Agrobacterium*-mediated transformation.

12. A method of treating a disease in a subject in need thereof, comprising delivering to the subject an effective amount of the genome editing system of any one of claims 1 and 2-6 to modify a gene related to the disease in the subject.

13. The method of claim 12, wherein the subject is a mammal or a human.

14. The method of claim 13, wherein the disease is selected from tumors, inflammation, Parkinson's disease, cardiovascular disease, Alzheimer's disease, autism, drug addiction, age-related macular degeneration, schizophrenia, and hereditary diseases.

\* \* \* \* \*